United States Patent
Wang et al.

(10) Patent No.: US 11,391,725 B2
(45) Date of Patent: Jul. 19, 2022

(54) METHODS FOR IMPROVING CELL VIABILITY IN A PRODUCTION BIOREACTOR

(71) Applicant: Genzyme Corporation, Cambridge, MA (US)

(72) Inventors: Jonathan Wang, Bridgewater, NJ (US); Neha Shah, Bridgewater, NJ (US); Jason Walther, Bridgewater, NJ (US); Jiuyi Lu, Bridgewater, NJ (US); Timothy Johnson, Bridgewater, NJ (US); Yukun Ren, Bridgewater, NJ (US); Jean McLarty, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 572 days.

(21) Appl. No.: 16/355,387

(22) Filed: Mar. 15, 2019

(65) Prior Publication Data

US 2019/0285617 A1     Sep. 19, 2019

Related U.S. Application Data

(60) Provisional application No. 62/645,755, filed on Mar. 20, 2018, provisional application No. 62/644,339, filed on Mar. 16, 2018.

(51) Int. Cl.
| | | |
|---|---|---|
| *G01N 33/50* | (2006.01) | |
| *C12Q 1/32* | (2006.01) | |
| *C12Q 1/02* | (2006.01) | |
| *C12M 1/34* | (2006.01) | |

(52) U.S. Cl.
CPC ......... *G01N 33/5014* (2013.01); *C12M 41/46* (2013.01); *C12Q 1/025* (2013.01); *C12Q 1/32* (2013.01)

(58) Field of Classification Search
CPC ...... C12M 41/46; C12M 27/20; C12M 41/32; C12M 41/42; C12M 47/12; G01N 33/5014; C12Q 1/025; C12Q 1/32
See application file for complete search history.

(56) References Cited

U.S. PATENT DOCUMENTS

| | | | | |
|---|---|---|---|---|
| 5,563,068 A * | 10/1996 | Zhang | .................... | C12M 23/34 435/295.2 |
| 2012/0164066 A1 | 6/2012 | Greene et al. | | |
| 2013/0071906 A1* | 3/2013 | Grillberger | .......... | C12N 5/0686 435/226 |
| 2015/0125905 A1* | 5/2015 | Pla | ....................... | C12N 5/0603 435/69.6 |
| 2015/0353883 A1* | 12/2015 | Gilbert | ................. | C07K 14/755 435/70.21 |
| 2016/0039911 A1* | 2/2016 | Lesnicki | .................. | C12N 1/16 435/69.6 |
| 2016/0131634 A1 | 5/2016 | Hu et al. | | |
| 2016/0177361 A1 | 6/2016 | Hwang et al. | | |
| 2016/0186226 A1* | 6/2016 | Han | ....................... | C12P 21/00 435/71.2 |

OTHER PUBLICATIONS

Laluce et al. Biotechnol. Prod. Process Engineer. (2009) 83: 627-637 (Year: 2009).*
Xu et al. Biotechnol. Progress (published online May 17, 2017) 3394): 1146-1159 (Year: 2017).*
Zhang et al. J. Biotechnol. (1992) 25: 289-306 (Year: 1992).*
Velugula-Yellela et al. Biotech. Progress (2018; published online Nov. 16, 2017) 34(1): 262-270 (Year: 2017).*
Luders et al. Appl. Microbiol. Biotechnol. (2011) 91: 81-90 (Year: 2011).*
PCT International Preliminary Report on Patentability in International Appln. No. PCT/US2019/022530, dated Sep. 22, 2020, 10 pages.
Ahmadi et al., "Application of the central composite design and response surface methodology to the advanced treatment of olive oil processing wastewater using Fenton's peroxidation," Journal of Hazardous Materials 123(1-3):187-195, Aug. 2005.
Bergeron et al., "Polydimethylsiloxane (PDMS)-based antifoams," Colloids and Surfaces: A: Physicochemical and Engineering Aspects 1(3):103-120, Apr. 1997.
Brečević et al., "Mechanism of antifoaming action of simethicone," Journal of Applied Technology 14(3):207-211, May 1994.
Gebauer et al., "Engineered protein scaffolds as next-generation antibody therapeutics," Current Opinion in Chemical Biology 13(2):245-255, Jun. 2009.
Vicente et al. "Application of the factorial design of experiments and response surface methodology to optimize biodiesel production," Industrial crops and products 8.1 (1998): 29-35.
Hesse et al., "Comparison of a production process in a membrane-aerated stirred tank and up to 1000-L airlift bioreactors using BHK-21 cells and chemically defined protein-free medium," Biotechnology Progress, American Chemical Society 19(3):833-843, May 1, 2003.
International Search Report and Written Opinion in Application No. PCT/US2019/022530, dated Jul. 18, 2019, 14 pages.
Ma et al., "Quantitative studies of cell-bubble interactions and cell damage at different Pluronic F-68 and cell concentrations," Biotechnology progress, 20(4):1183-1191, Aug. 6, 2004.
Marinova et al., "Foam destruction by mixed solid-liquid antifoams in solutions of alkyl glucoside: Electrostatic interactions and dynamic effects," Langmuir 17(8):2426-2436, Apr. 2001.
Moghimi et al., "Poloxamers and poloxamines in nanoparticle engineering and experimental medicine," Trends in Biotechnology 18(10):412-420, Oct. 2000.
Murhammer et al., "Pluronic polyols—cell protection," Encyclopedia of Industrial Biotechnology: Bioprocess, Bioseparation, and Cell Technology, pp. 1-5, Oct. 2009.

(Continued)

*Primary Examiner* — Susan M Hanley
(74) *Attorney, Agent, or Firm* — Fish & Richardson P.C.

(57) ABSTRACT

Provided herein are methods of predicting the effect of a concentration of a sensitizer on cell viability in a production bioreactor, methods of improving cell viability in a production bioreactor, methods of predicting cell viability in a production bioreactor, and methods for culturing a cell in a production bioreactor.

10 Claims, 12 Drawing Sheets

(56) References Cited

OTHER PUBLICATIONS

Murhammer et al., "Structural features of nonionic polyglycol polymer molecules responsible for the protective effect in sparged animal cell bioreactors," Biotechnology Progress 6(2):142-148, Mar. 1990.
Velugula-Yellela et al., "Impact of media and antifoam selection on monoclonal antibody production and quality using a high throughput micro-bioreactor system," Biotechnology Progress 34(1):262-270, 2018.
Schroeder et al., "Differentiation and lineage selection of mouse embryonic stem cells in a stirred bench scale bioreactor with automated process control," Biotechnology and Bioengineering 92(7):920-933, Dec. 30, 2005.
Vandervoort et al., "Biocompatible stabilizers in the preparation of PLGA nanoparticles: a factorial design study," International journal of pharmaceutics 238(1-2):77-92, May 2002.
European Office Action in Patent Application No. 19714056.9, dated Oct. 30, 2020, 3 pages.
Nielsen, "Chapter Twelve—Protein Expression-Yeast," Methods in Enzymology, 2014, 536:133-147.
Rashmika et al., "Impact of media and antifoam selection on monoclonal antibody production and quality using a high throughput micro-bioreactor system," Biotechnol. Prog., 2018, 34(1):262-270.
Office Action in Russian Application No. 2020133815, dated Jan. 31, 2022, 9 pages (with English translation).

\* cited by examiner

RPM set to the 3rd power sLDH Predicted P<.0001 RSq=0.84 RMSE=12.219

| 10L Benchtop | | Shakeflask Model | |
|---|---|---|---|
| Observed LDH | | Predicted LDH | |
| Avg | Std | Avg | Std |
| 39.00 | 8.49 | 37.00 | 4.24 |
| 43.00 | 7.07 | 54.00 | 4.24 |
| 80.50 | 3.54 | 80.00 | 4.24 |
| Min | Max | Min | Max |
| 30.51 | 47.49 | 32.76 | 41.24 |
| 35.93 | 50.07 | 49.76 | 58.24 |
| 76.96 | 84.04 | 75.76 | 84.24 |

| LDH | | Predicted | |
|---|---|---|---|
| 50L | | Model | std |
| S16 | 39.72 | 37.00 | 4.24 |
| S18 | 51.05 | 37.00 | 4.24 |
| S19 | 39.6 | 37.00 | 4.24 |
| 100L | | 37.00 | 4.24 |
| S27 | 37.61 | 37.00 | 4.24 |
| S28 | 42.55 | 37.00 | 4.24 |

METHODS FOR IMPROVING CELL VIABILITY IN A PRODUCTION BIOREACTOR

CROSS-REFERENCE TO RELATED APPLICATIONS

This application claims priority to U.S. Provisional Patent Application Ser. No. 62/644,339 filed Mar. 16, 2018, and U.S. Provisional Patent Application Ser. No. 62/645,755 filed Mar. 20, 2018; entire contents of each of these applications are herein incorporated by reference.

TECHNICAL FIELD

This disclosure is related to methods of improving cell viability in a production bioreactor and the fields of biotechnology and cell biology.

BACKGROUND

Process intensification provides many advantages for the production of recombinant therapeutic proteins. One of the strategies for process intensification is to maintain high cell densities to improve recombinant protein production, which further requires high oxygen demand. Oxygen sparge in a production bioreactor leads to foaming in the production bioreactor. Foaming often occurs in both intensified fed batch and perfusion processes. Thus, antifoaming agents are usually added in these processes. However, the addition and accumulation of antifoam agents can make cells become sensitive to shear, leading to increased cell death.

Thus, there is a need to develop a model to characterize acceptable cell culture conditions in a production bioreactor among various cell culture parameters, e.g., shear, media components and additives, and antifoam concentration.

SUMMARY

The present invention is based, e.g., on the discovery that the presently claimed methods that utilize data obtained in a test culture vessel (e.g., a baffled shake flask) can be used to accurately predict the effect of a concentration of a sensitizer on cell viability in a production bioreactor, accurately select a condition that is optimal for cell viability in a production bioreactor, predict cell viability in a production bioreactor, and accurately identify a set of conditions that can be used to culture a cell in a production bioreactor.

In one aspect, the disclosure is related to methods of predicting the effect of a concentration of a sensitizer on cell viability in a production bioreactor. The methods involve (a) determining cell viability under a plurality of test conditions in a test culture vessel, wherein the plurality of test conditions are defined by a set of parameters; and (b) based on the cell viability in the test culture vessel under the plurality of conditions, predicting the effect of a concentration of a sensitizer on cell viability in a production bioreactor.

In some embodiments, the set of parameters comprises shear stress, concentration of the sensitizer, and concentration of a protectant.

In some embodiments, the plurality of testing conditions are selected based on full factorial screening and/or inscribed center composite design.

In some embodiments, the sensitizer is an antifoam agent.

In some embodiments, the antifoam is a polydimethylsiloxane-based antifoam, or simethicone.

In some embodiments, the test culture vessel has a volume of about 5 mL to about 5 L, or has a volume of about 10 mL to about 500 mL. In some embodiments, the test culture vessel is a baffled shake flask.

In some embodiments, the production bioreactor has a volume of about 5 L to about 20,000 L, or has a volume of about 50 L to about 10,000 L. In some embodiments, the production bioreactor is a perfusion bioreactor or a fed batch bioreactor.

In some embodiments, the methods further comprise culturing a cell in the production bioreactor using a concentration of the sensitizer predicted to have a specific cell death rate of less 40% per day during the culturing of the cell in the production bioreactor.

In some embodiments, the methods further comprise culturing a cell in the production bioreactor using a concentration of the sensitizer predicted to have a specific cell death rate of less than 20% per day during the culturing of the cell in the production bioreactor.

In some embodiments, the methods further comprise culturing a cell in the production bioreactor using a concentration of the sensitizer predicted to result in a cell specific LDH production of less than 150 nU/cell/day during the culturing of the cell in the production bioreactor.

In some embodiments, the methods further comprise culturing a cell in the production bioreactor using a concentration of the sensitizer predicted to result in a cell specific LDH production of less than 100 nU/cell/day during the culturing of the cell in the production bioreactor.

In some embodiments, the methods further comprise culturing a cell in the production bioreactor using a concentration of the sensitizer predicted to result in an apparent growth rate of greater than 1% per day during the culturing of the cell in the production bioreactor.

In some embodiments, the methods further comprise culturing a cell in the production bioreactor using a concentration of the sensitizer predicted to result in an apparent growth rate of greater than 5% per day during the culturing of the cell in the production bioreactor.

In some embodiments, the cell contains a nucleic acid encoding a recombinant therapeutic protein.

In some embodiments, the methods further comprise collecting the recombinant therapeutic protein. In some embodiments, the methods further comprise purifying the recombinant therapeutic protein. In some embodiments, the methods further comprise formulating the purified recombinant therapeutic protein.

In some embodiments, the cell is a bacterium, a yeast, or a mammalian cell.

In some embodiments, the cell viability is determined by measuring a concentration of lactic acid dehydrogenase (LDH) in the test culture vessel.

In some embodiments, the test culture vessel is a baffled shake flask and the plurality of test conditions comprise one or more of:

(a) a rotary agitation of about 125 RPM to about 400 RPM;

(b) a concentration of the sensitizer of about 0 ppm to about 5000 ppm; and (c) a concentration of a protectant that is about 1 g/L to about 10 g/L.

In some embodiments, the protectant is a poloxamer, a poloxamine, or a non-ionic surfactant Pluronic®.

In some embodiments, the poloxamer is poloxamer-188, poloxamer-401, poloxamer-402, or poloxamer-407.

In some embodiments, the poloxamine is poloxamine-904 or poloxamine-908.

In another aspect, the disclosure is related to methods of improving cell viability in a production bioreactor. The methods involve (a) determining cell viability under a plurality of test conditions in a test culture vessel, wherein the plurality of conditions are defined by a set of parameters;

(b) based on the cell viability in the test culture vessel under the plurality of conditions, selecting a condition that is optimal for cell viability in a production bioreactor; and (c) culturing a cell in the production bioreactor under the selected condition.

In some embodiments, the set of parameters comprises shear stress, concentration of a sensitizer, and concentration of a protectant.

In some embodiments, the plurality of testing conditions are selected based on full factorial screening and/or inscribed center composite design.

In some embodiments, the sensitizer is an antifoam agent. In some embodiments, the antifoam is a polydimethylsiloxane-based antifoam or simethicone.

In some embodiments, the test culture vessel has a volume of about 5 mL to about 5 L.

In some embodiments, the test culture vessel has a volume of about 10 mL to about 500 mL. In some embodiments, the test culture vessel is a baffled shake flask.

In some embodiments, the production bioreactor has a volume of about 5 L to about 20,000 L. In some embodiments, the production bioreactor has a volume of about 50 L to about 10,000 L. In some embodiments, the production bioreactor is a perfusion bioreactor or a fed batch bioreactor.

In some embodiments, step (c) results in a specific cell death rate of less than 40% per day during the culturing of the cell in the production bioreactor. In some embodiments, step (c) results in a specific cell death rate of less than 20% per day during the culturing of the cell in the production bioreactor. In some embodiments, step (c) results in a cell specific LDH production of less than 150 nU/cell/day during the culturing of the cell in the production bioreactor. In some embodiments, step (c) results in a cell specific LDH production of less than 100 nU/cell/day during the culturing of the cell in the production bioreactor. In some embodiments, step (c) results in an apparent growth rate of greater than 1% per day during the culturing of the cell in the production bioreactor. In some embodiments, step (c) results in an apparent growth rate of greater than 5% per day during the culturing of the cell in the production bioreactor.

In some embodiments, the cell contains a nucleic acid encoding a recombinant therapeutic protein.

In some embodiments, the methods further comprise collecting the recombinant therapeutic protein. In some embodiments, the methods further comprise purifying the recombinant therapeutic protein. In some embodiments, the methods further comprise formulating the purified recombinant therapeutic protein.

In some embodiments, the cell is a bacterium, a yeast, or a mammalian cell. In some embodiments, the cell viability is determined by measuring a concentration of lactic acid dehydrogenase (LDH) in the test culture vessel.

In some embodiments, the test culture vessel is a baffled shake flask and the plurality of test conditions comprise one or more of:

(a) a rotary agitation of about 125 RPM to about 400 RPM;

(b) a concentration of a sensitizer of about 0 ppm to about 5000 ppm; and (c) a concentration of a protectant that is about 1 g/L to about 10 g/L.

In some embodiments, the protectant is a poloxamer, a poloxamine, or a non-ionic surfactant Pluronic®. In some embodiments, the poloxamer is poloxamer-188, poloxamer-401, poloxamer-402, or poloxamer-407. In some embodiments, the poloxamine is poloxamine-904 or poloxamine-908.

In another aspect, the disclosure is related to methods for predicting cell viability in a production bioreactor. The methods involve (a) selecting a set of parameters comprising at least two parameters;

(b) determining cell viability under a plurality of test conditions as defined by the set of parameters in a test culture vessel; and (c) based on the cell viability in the test culture vessel under the plurality of conditions, predicting cell viability in the production bioreactor.

In some embodiments, the set of parameters comprises shear stress, concentration of a sensitizer, and concentration of a protectant.

In some embodiments, the plurality of test conditions are selected based on full factorial screening and/or inscribed center composite design.

In some embodiments, the sensitizer is an antifoam agent.

In some embodiments, the antifoam is a polydimethylsiloxane-based antifoam. In some embodiments, the antifoam is simethicone.

In some embodiments, the test culture vessel has a volume of about 5 mL to about 5 L.

In some embodiments, the test culture vessel has a volume of about 10 mL to about 500 mL.

In some embodiments, the test culture vessel is a baffled shake flask.

In some embodiments, the production bioreactor has a volume of about 5 L to about 20,000 L, or has a volume of about 50 L to about 10,000 L.

In some embodiments, the production bioreactor is a perfusion bioreactor or a fed batch bioreactor.

In some embodiments, the methods further comprise culturing a cell in the production bioreactor using a condition predicted to result in a specific cell death rate of less 40% per day during the culturing of the cell in the production bioreactor.

In some embodiments, the methods further comprise culturing a cell in the production bioreactor using a condition predicted to result in a specific cell death rate of less than 20% per day during the culturing of the cell in the production bioreactor.

In some embodiments, the methods further comprise culturing a cell in the production bioreactor using a condition predicted to result in a cell specific LDH production of less than 150 nU/cell/day during the culturing of the cell in the production bioreactor.

In some embodiments, the methods further comprise culturing a cell in the production bioreactor using a condition predicted to result in a cell specific LDH production of less than 100 nU/cell/day during the culturing of the cell in the production bioreactor.

In some embodiments, the methods further comprise culturing a cell in the production bioreactor using a condition predicted to result in an apparent growth rate of greater than 1% per day during the culturing of the cell in the production bioreactor.

In some embodiments, the methods further comprise culturing a cell in the production bioreactor using a condition predicted to result in an apparent growth rate of greater than 5% per day during the culturing of the cell in the production bioreactor.

In some embodiments, the cell contains a nucleic acid encoding a recombinant therapeutic protein.

In some embodiments, the methods further comprise collecting the recombinant therapeutic protein. In some embodiments, the methods further comprise purifying the recombinant therapeutic protein. In some embodiments, the methods further comprise formulating the purified recombinant therapeutic protein.

In some embodiments, the cell is a bacterium, a yeast, or a mammalian cell.

In some embodiments, the cell viability is determined by measuring a concentration of lactic acid dehydrogenase (LDH) in the test culture vessel.

In some embodiments, the test culture vessel is a baffled shake flask and the plurality of test conditions comprise one or more of:
  (a) a rotary agitation of about 125 RPM to about 400 RPM;
  (b) a concentration of the sensitizer of about 0 ppm to about 5000 ppm; and
  (c) a concentration of a protectant that is about 1 g/L to about 10 g/L.

In some embodiments, the protectant is a poloxamer, a poloxamine, or a non-ionic surfactant Pluronic®. In some embodiments, the poloxamer is poloxamer-188, poloxamer-401, poloxamer-402, or poloxamer-407. In some embodiments, the poloxamine is poloxamine-904 or poloxamine-908.

In another aspect, the disclosure also provides methods for culturing a cell in a production bioreactor, comprising a culturing a cell in a liquid culture medium under one or more of the following conditions:
  a) the production bioreactor has a P/V (W/m$^3$) from about 1.0 to about 110.0 (e.g., from about 10.0 to about 100.0, from about 20.0 to about 80.0, from about 40.0 to about 60.0, or about 6.0);
  b) the production bioreactor has a volume of air per volume of liquid per minute (VVM) (min') from about 0.01 to about 0.10 (e.g., from about 0.02 to about 0.08, from about 0.04 to about 0.06, or about 0.06);
  c) the medium comprises a sensitizer that has a concentration of about 0 ppm to about 5000 ppm (e.g., from about 50 ppm to about 4000 ppm, from about 1000 ppm to about 2000 ppm, or about 100 ppm); and
  d) the liquid culture medium comprises a protectant that has a concentration that is from about 1 g/L to about 15 g/L (e.g., from about 2 g/L to about 10 g/L, from about 3 g/L to about 7 g/L, from about 4 g/L to about 6 g/L, or about 5 g/L).

In some embodiments, the sensitizer is an antifoam agent.

In some embodiments, the antifoam is a polydimethylsiloxane-based antifoam. In some embodiments, the antifoam is simethicone.

In some embodiments, the protectant is a poloxamer, a poloxamine, or a non-ionic surfactant Pluronic®.

In some embodiments, the poloxamer is poloxamer-188, poloxamer-401, poloxamer-402, or poloxamer-407. In some embodiments, the poloxamine is poloxamine-904 or poloxamine-908.

In some embodiments, the production bioreactor has a volume of about 5 L to about 20,000 L. In some embodiments, the production bioreactor has a volume of about 50 L to about 10,000 L. In some embodiments, the production bioreactor is a perfusion bioreactor or a fed batch bioreactor.

In some embodiments, the methods result in a specific cell death rate of less than 40% per day during the culturing of the cell in the production bioreactor. In some embodiments, the methods result in a specific cell death rate of less than 20% per day during the culturing of the cell in the production bioreactor. In some embodiments, the methods result in a cell specific LDH production of less than 150 nU/cell/day during the culturing of the cell in the production bioreactor. In some embodiments, the methods result in a cell specific LDH production of less than 100 nU/cell/day during the culturing of the cell in the production bioreactor. In some embodiments, the methods result in an apparent growth rate of greater than 1% per day during the culturing of the cell in the production bioreactor. In some embodiments, the methods result in an apparent growth rate of greater than 5% per day during the culturing of the cell in the production bioreactor.

In some embodiments, the cell contains a nucleic acid encoding a recombinant therapeutic protein.

In some embodiments, the methods further comprise collecting the recombinant therapeutic protein. In some embodiments, the methods further comprise purifying the recombinant therapeutic protein. In some embodiments, the methods further comprise formulating the purified recombinant therapeutic protein.

In some embodiments, the cell is a bacterium, a yeast, or a mammalian cell. In some embodiments, the cell viability is determined by measuring a concentration of lactic acid dehydrogenase (LDH) in the test culture vessel.

As used herein, the word "a" before a noun represents one or more of the particular noun. For example, the phrase "a cell" represents "one or more cells."

The term "protectant" means an agent that decreases a cell's sensitivity (e.g., a mammalian cell's sensitivity) to shear stress during culturing in a vessel (e.g., a test culture vessel or a production bioreactor). A non-limiting examples of protectants include, e.g., poloxamers (e.g., poloxamer-188, poloxamer-401, poloxamer-402, and poloxamer-407), poloxamines (e.g., poloxamine-904 or poloxaminer-908), and non-ionic surfactant Pluronic®. Additional examples of protectants are described herein and are known in the art.

The term "sensitizer" means an agent that is added to and/or is present in a liquid culture medium of a culture of cells (e.g., a mammalian cell culture) that increases the cells' sensitivity to shear stress during culturing in a vessel (e.g., a test culture vessel or a production bioreactor). Non-limiting examples of sensitizers include antifoam (e.g., a polydimethylsiloxane-based antifoam or simethicone). Additional examples of sensitizers are described herein and are known in the art.

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "culturing" or "cell culturing" means the maintenance or proliferation of a mammalian cell under a controlled set of physical conditions.

The term "culture of cells" or "cell culture" means a liquid culture medium containing a plurality of cells that is maintained or proliferated under a controlled set of physical conditions.

The term "liquid culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a bioreactor can be substantially free of mammalian cells.

The term "animal-derived component free liquid culture medium" means a liquid culture medium that does not contain any components (e.g., proteins or serum) derived from a mammal.

The term "serum-free liquid culture medium" means a liquid culture medium that does not contain a mammalian serum.

The term "serum-containing liquid culture medium" means a liquid culture medium that contains a mammalian serum.

The term "chemically-defined liquid culture medium" is a term of art and means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "perfusion bioreactor" means a bioreactor containing a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, the second liquid culture medium can be the same as the first liquid culture medium. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder. In some examples of fed-batch culture, the second liquid culture medium is completely different formulation as compared to the first liquid culture medium.

The term "concentrated fed-batch bioreactor) is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium with substantial or significant removal of the first liquid culture medium or second liquid culture medium from the cell culture while without removing product from the bioreactor. The second liquid culture medium can be the same as the first liquid culture medium. In some examples of concentrated fed-batch culture, the second liquid culture medium is a concentrated form of the first liquid culture medium. In some examples of concentrated fed-batch culture, the second liquid culture medium is added as a dry powder. In some examples of concentrated fed-batch culture, the second liquid culture medium is completely different formulation of the first liquid culture medium.

"Rotary agitation" is a term well-known in the art and refers to the movement of a shake flask in a generally circular fashion, e.g., clock-wise or counter-clockwise, in order to, e.g., increase the dissolved O2 concentration in a liquid culture medium contained therein. Agitation can be performed using any art-known method, e.g., an instrument that moves the shake flask in a circular or ellipsoidal motion, such as a rotary shaker. Exemplary devices that can be used to perform rotary agitation are described herein. Additional examples of such devices are also known in the art and are commercially available.

The term "shake flask" is meant a vessel (e.g., a sterile vessel) that can hold a volume of liquid culture medium that has at least one gas permeable surface (e.g., an end that has at a gas-permeable element, e.g., a membrane, which may also act as a sterile barrier) and/or at least one vent cap, and at least a portion of its shape is approximately frustoconical. For example, a shake flask can be a baffled shake flask or an Erlenmeyer flask, or any art-recognized modified version thereof.

The term "production bioreactor" is a term of art and means a large-scale bioreactor (e.g., having an internal volume over 5 L, 1,000 L, 5,000 L, 10,000 L, 20,000 L, 50,000 L, or 100,000 L). For example, a production bioreactor can be a perfusion bioreactor.

The term "test culture vessel" is a term of art and means a small-scale bioreactor (e.g., relative to a production bioreactor) having a volume of about 2 mL to about 500 mL. In some examples, the height and width ratio of the test culture vessel corresponds to about the height and width ratio of the production bioreactor in the methods described herein. In some embodiments, the test culture vessel is a shake flask (e.g., a baffled shake flask). Additional examples of a test culture vessel are described herein and are known in the art.

The term "batch culturing" is a term of art and means a vessel (e.g., bioreactor) containing a plurality of cells (e.g., mammalian cells) in a liquid culture medium, wherein the culturing of the cells present in the vessel (e.g., bioreactor) does not include the addition of a substantial or significant amount of fresh liquid culture medium to the cell culture and does not include the removal of a substantial or significant amount of liquid culture medium from the cell culture during culturing.

The term "fed-batch culturing" is a term of art and means a vessel (e.g., a production bioreactor) including a plurality of cells (e.g., mammalian cells) in a liquid culture medium, wherein the culturing of the cells present in the vessel (e.g., production bioreactor) includes the periodic or continuous addition of fresh liquid culture medium to the vessel without substantial or significant removal of liquid culture medium from the vessel during culturing. The fresh liquid culture medium can be the same as the liquid culture medium present in the vessel at the start of the culturing. In some examples of fed-batch culturing, the fresh liquid culture medium is a concentrated form of the liquid culture medium present in the vessel at the start of culturing. In some examples of fed-batch culture, the fresh culture medium is added as a dry powder. In some examples of fed-batch culturing, the fresh culture medium is a completely different formulation compared to the liquid culture medium present in the vessel at the start of culturing.

The methods described herein provide several advantages. For example, it can align different scales, predict Δparameters, and optimize existing design space. It can also increase predictability/alignment of performance across scales, create more representative small scale models, increase process robustness, improve shear tolerance for process intensification, and provide guidance on sensitizer and protectant addition across different shear profiles (FIG. 12).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

This disclosure relates to methods of optimizing process intensification for production of proteins or polypeptides. In one aspect, the disclosure is related to a small scale test culture vessel (e.g., baffled shake flask) model that can characterize an operation space as defined by various operation parameters, e.g., protectant (e.g., poloxamer-188) concentration, sensitizer (e.g., antifoam), shear stress (e.g., agitation rate or oxygen sparging rate), media components and additives, pH, and time etc. Particularly, the methods described herein can be used to predict the effect of these operation parameters on cell culture growth and viability in a production bioreactor. Orthogonal approaches have been used to correlate shear stress between small scale and larger scale models, and the predicted operation space has been validated by the data at the benchtop scale and at the production scale.

Thus, provided herein are methods of predicting the effect of a concentration of a sensitizer on cell viability in a production bioreactor, methods of improving cell viability in a production bioreactor, methods for predicting cell viability in a production bioreactor, and methods for culturing a cell in a production bioreactor. Non-limiting aspects of these methods are described herein, and may be combined without limitation.

Process Intensification

Process intensification refers to improvements in manufacturing and processing by optimizing existing operation schemes so that the manufacturing process can be more precise and more efficient. These improvements can bring various advantages, e.g., increasing biomass, improving volumetric productivity, optimizing facility capacity utilization, reducing cost of goods, maintaining or improving product quality consistency, reducing facility footprint, and/or reducing unit operations. At the molecular level, process intensification can also involve enhancing mixing, improving reaction kinetics, and/or increasing yields and specificity.

Figure 1:
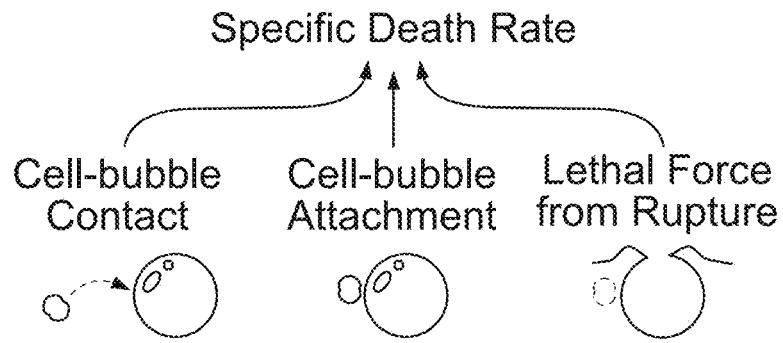
FIG. 1 is a diagram showing how bubbles in a cell culture medium can cause cell death.

The present disclosure is related to process intensification for the production of proteins or polypeptides (e.g., recombinant therapeutic proteins, recombinant proteins, or recombinant polypeptides). One strategy to increase recombinant therapeutic protein or polypeptide production is to increase cell densities. High cell densities usually require high oxygen consumption, and the required oxygen sparge often leads to foaming issues (i.e., bubbles). As shown in FIG. 1, bubbles can lead to cell death, e.g., through cell-bubble contact, cell bubble attachment, or lethal force from bubble rupture. Formula 1 shows the relationship between cell death rate, volumetric aeration, and bubble size.

$$\text{Death Rate} \propto \frac{\text{(Volumetric Aeration)}}{\text{(Bubble Size)}^3} \quad \text{(Formula 1)}$$

Thus, antifoaming agents are often added to the cell culture process. However, the addition and/or accumulation of antifoam agents can cause a negative impact on cell culture performance (e.g., mammalian cell culture performance). In some cases, the addition and accumulation of antifoam agents can lead to increased cell death rate, particularly at the production scale (production bioreactor scale). Therefore, it is important to assess the effects of operation parameters or changes in these operation parameters (e.g., antifoam agents or some other parameters) at the production scale (production bioreactor scale).

Sensitizers, Agitation, and Protectants

Because it is prohibitively expensive to test the effects of various operation parameters at the production scale (production bioreactor scale), pilot experiments are usually performed in test culture vessels (e.g., shake flasks, laboratory fermenters, or pilot fermenters) first. These test culture vessels can be operated to test the effects of various parameters, e.g., agitation, sensitizer concentration, protectant concentration, temperature, pH, nutrient composition, biomass loading and feeding strategy at a small scale, and correlate the observed effects with effects at the production scale (production bioreactor scale). In many traditional methods, power/volume (P/V), volumetric mass transfer coefficient (kLa), tip speed, mixing time, computational fluid dynamics (CFD) modelling are often used to correlate the results in test culture vessels with the effects at the production scale (production bioreactor scale).

Among these various parameters, sensitizer parameters (e.g., concentration of sensitizer) are especially difficult to scale-up. In some embodiments of any of the methods described herein, a sensitizer can be an antifoam agent (e.g., simethicone, simethicone emulsion, or a polydimethylsiloxane (PDMS)-based oil). A description of the antifoam agents can be found, e.g., in Brečević et al. "Mechanism of antifoaming action of simethicone," *J. Appl. Toxicol.* 14(3): 207-211, 1994; and Bergeron, et al. "Polydimethylsiloxane (PDMS)-based antifoams," Colloids and Surfaces A: Physicochemical and Engineering Aspects 122(1-3):103-120, 1997; both of which are incorporated herein by reference in its entirety.

Additional examples of sensitizers include, e.g., organic oil-based sensitizers, silicone oil-based sensitizers, and mixed liquid-solid mixture/emulsified sensitizers (e.g., fumed silica, oil combination antifoams). A sensitizer can be a silicone foam control agent, e.g., XIAMETER® ACP-0100 Antifoam Compound, XIAMETER® ACP-1500 Antifoam Compound, XIAMETER® AFE-1510 Antifoam Emulsion, XIAMETER® AFE-1520 Antifoam Emulsion, XIAMETER® AFE-1530 Antifoam Emulsion, XIAMETER® ACP-1400 Antifoam Compound, XIAMETER® AFE-0700 Antifoam Emulsion, XIAMETER® ACP-1920 Powdered Antifoam, and XIAMETER® PMX-200 Silicone Fluid. Additional examples of sensitizers include Dow Corning® antifoam C emulsion, Antifoam 204 (Sigma Aldrich), Antifoam A (Sigma Aldrich), Antifoam B emulsion (Sigma Aldrich), Antifoam C emulsion (Sigma Aldrich), Antifoam Y-30 Emulsion (Sigma Aldrich), Antifoam 0-30 (Sigma Aldrich), and Antifoam SE-15 (Sigma Aldrich). A non-limiting example of an organic, non-silicone polypropylene-based polyether sensitizer is antifoam 204. A non-limiting example of a simethicone emulsion is Antifoam EX-Cell. Non-limiting examples of mixed solid-liquid antifoams include silicone oil (PDMS), compound A, modified CA (MCA), emulsion A (EA), and analogue of EA (AEA) described in Marinova et al., Langmuir 17:2426-2436, 2001. Non-limiting examples of polydimethylsiloxane (PMSA)-based antifoams are described in Bergeron et al., *Colloids and Surfaces A: Physiochemical and Engineering Aspects* 122:103-120, 1997.

Additional examples of sensitizers are known in the art. See, e.g., Rashmika et al., *Biotechnol. Prog.* 34(1):262-270, 2018.

Some other parameters, for example, baffling, flask size, agitation, also have an impact on the cell's sensitivity to shear. Because of the interactions with other parameters, these sensitizer parameters (e.g., concentration of an antifoam agent) often have non-linear relation in the scale-up process, and are geometrically un-related across different scales. Therefore, traditional models are usually powerless in terms of predicting the effects of the sensitizer parameters at the production scale.

Figure 2:
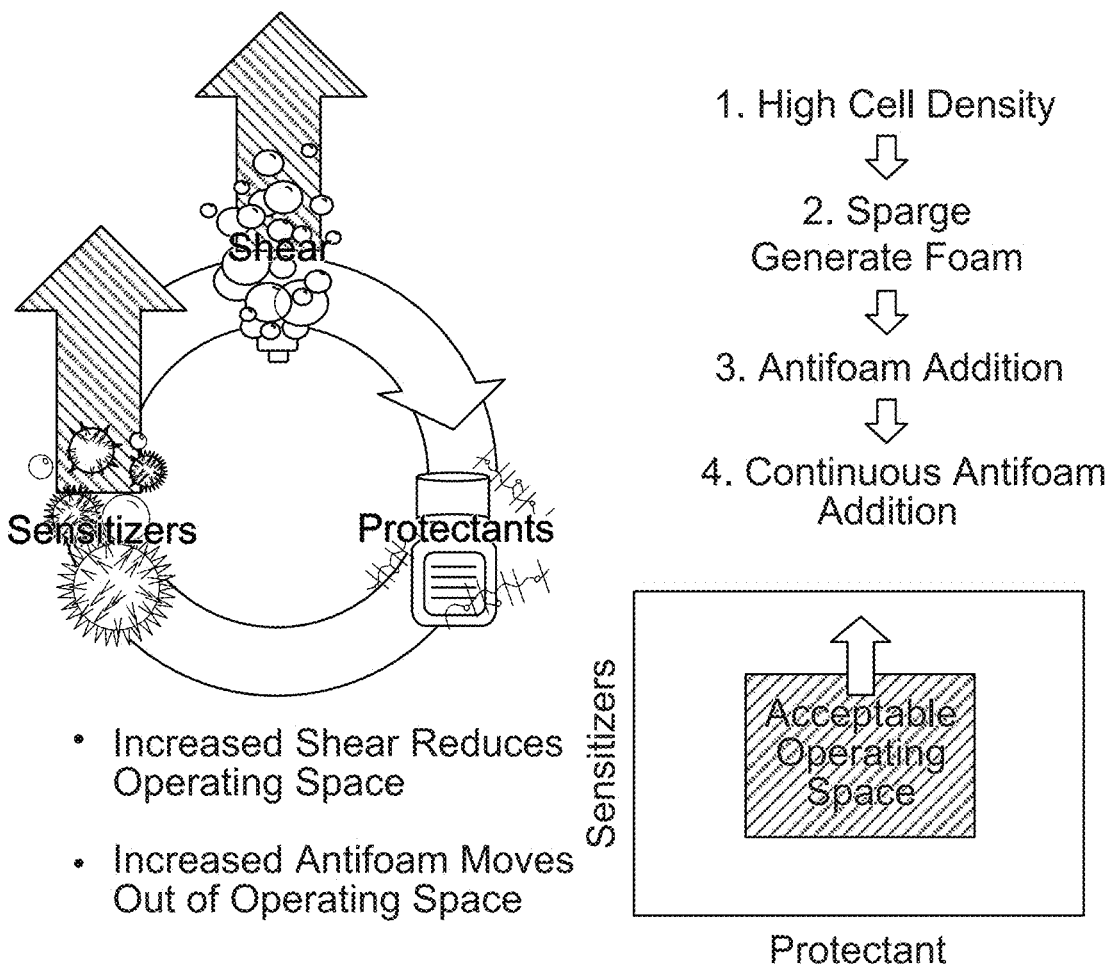
FIG. 2 is a diagram illustrating addition of antifoam (an exemplary sensitizer) can move the operating conditions out of the acceptable operating space.

What makes the prediction even more challenging is that the sensitizer parameter can change in the entire production period. For example, during the production process (e.g., the culturing of a cell in a production bioreactor), the cell density increases, and a higher oxygen sparge is required. Therefore, more antifoam agents are required and are added to the production bioreactor. The increased concentration of antifoam agents make the cells even more sensitive to shear stress, and moves the operating condition quickly out of acceptable operating space (FIG. 2).

In addition, protectants can protect cells from the increased shear stress and are often added to the liquid culture medium. The increased protectant concentration may be necessary to mitigate the negative impacts of sensitizers, but the interaction of protectants with other parameters makes it difficult to determine the exact amount of protectant that is needed. Some common protectants include, e.g., poloxamer, poloxamine, and/or non-ionic surfactant Pluronic®. In some embodiments, the protectant is a poloxamer (e.g., poloxamer-188, poloxamer-401, poloxamer-402, or poloxamer-407). In some other embodiments, the protectant is a poloxamine (e.g., poloxamine-904 or poloxamine-908). In some additional embodiments, the protectant is a non-ionic surfactant Pluronic® (e.g., L-61, L-121, P-103, P-123, P-84, P-104, P-65, P-105, L-35, F-127, F-38, F-68, or F-108) or a reverse non-ionic surfactant Pluronic® (e.g., 25 R-2, 25 R-4, 25 R-5, 25 R-8, 10 R-5, or 10 R-8). A detailed description of exemplary protectants can be found, e.g., in Moghimi et al., "Poloxamers and poloxamines in nanoparticle engineering and experimental medicine," Trends in Biotechnology 18(10):412-420, 2000; Murhammer et al., "Structural features of nonionic polyglycol polymer molecules responsible for the protective effect in sparged animal cell bioreactors," Biotechnology Progress 6(2):142-148, 1990; Murhammer, "Pluronic® polyols, cell protection," Encyclopedia of Bioprocess Technology (1999); each of which is incorporated herein by reference in its entirety.

Modeling Based on Factorial Design and Center Composite Design

The disclosure provides modeling methods to capture the effects (e.g., cell viability, cell death rate, recombinant therapeutic protein production, or yield) of various operation parameters, e.g., protectants (media component/additive, e.g., Pluronic®), sensitizers (e.g., antifoam agents), and shear stress (agitation) for the purposes of optimizing reactors at any scale based on the results from test culture vessel models.

In one aspect, the methods described herein can be used to predict cell viability in a production bioreactor. The methods involve selecting a set of parameters comprising at least two (e.g., three, four, five, or six) parameters; determining cell viability under a plurality of test conditions as defined by the set of parameters in a test culture vessel (e.g., any of the test culture vessels described herein); and based on the cell viability in the test culture vessel under the plurality of conditions, predicting cell viability in the production bioreactor. Based on the prediction, the conditions with the improved cell viability can be identified. Also provided herein are methods of predicting the effect of a concentration of a sensitizer on cell viability in a production bioreactor. The methods involve determining cell viability under a plurality of test conditions in a test culture vessel, where the plurality of test conditions are defined by a set of parameters; and based on the cell viability in the test culture vessel under the plurality of conditions, predicting the effect of a concentration of a sensitizer on cell viability in a production bioreactor.

The test culture vessel can be a spin tube (e.g. baffled spin tube), a flask (e.g., a shake flask having a volume of about 3 L) (e.g., baffled shake flask.), an automated laboratory fermenter (Ambr 15 and Amber 250 from Sartorius), a laboratory fermenter, or a pilot fermenter. In some embodiments, the test culture vessel can have a volume of less than 5 L, less than 3 L, less than 1 L, less than 500 ml, or less than 100 ml (e.g., less than 1 L, or from 50 ml to 500 ml). In some embodiments, the test culture vessel has a volume (an interior volume) of about 5 mL to about 5 L (e.g., about 10 mL to about 500 mL, or about 2.5 L to about 3.5 L). For example, a test culture vessel can have a volume (an interior volume) of about 5 mL to about 5 L, about 5 mL to about 4.5 L, about 5 mL to about 4.0 L, about 5 mL to about 3.5 L, about 5 mL to about 3.0 L, about 5 mL to about 2.5 L, about 5 mL to about 2 L, about 5 mL to about 1.5 L, about 5 mL to about 1 L, about 5 mL to about 900 mL, about 5 mL to about 800 mL, about 5 mL to about 700 mL, about 5 mL to about 600 mL, about 5 mL to about 500 mL, about 5 mL to about 450 mL, about 5 mL to about 400 mL, about 5 mL to about 350 mL, about 5 mL to about 300 mL, about 5 mL to about 250 mL, about 5 mL to about 200 mL, about 5 mL to about 150 mL, about 5 mL to about 100 mL, about 5 mL to about 80 mL, about 5 mL to about 60 mL, about 5 mL to about 50 mL, about 5 mL to about 40 mL, about 5 mL to about 30 mL, about 5 mL to about 25 mL, about 5 mL to about 20 mL, about 5 mL to about 15 mL, about 5 mL to about 10 mL, about 10 mL to about 5 L, about 10 mL to about 4.5 L, about 10 mL to about 4.0 L, about 10 mL to about 3.5 L, about 10 mL to about 3.0 L, about 10 mL to about 2.5 L, about 10 mL to about 2 L, about 10 mL to about 1.5 L, about 10 mL to about 1 L, about 10 mL to about 900 mL, about 10 mL to about 800 mL, about 10 mL to about 700 mL, about 10 mL to about 600 mL, about 10 mL to about 500 mL, about 10 mL to about 450 mL, about 10 mL to about 400 mL, about 10 mL to about 350 mL, about 10 mL to about 300 mL, about 10 mL to about 250 mL, about 10 mL to about 200 mL, about 10 mL to about 150 mL, about 10 mL to about 100 mL, about 10 mL to about 80 mL, about 10 mL to about 60 mL, about 10 mL to about 50 mL, about 10 mL to about 40 mL, about 10 mL to about 30 mL, about 10 mL to about 25 mL, about 10 mL to about 20 mL, about 10 mL to about 15 mL, about 15 mL to about 5 L, about 15 mL to about 4.5 L, about 15 mL to about 4.0 L, about 15 mL to about 3.5 L, about 15 mL to about 3.0 L, about 15 mL to about 2.5 L, about 15 mL to about 2 L, about 15 mL to about 1.5 L, about 15 mL to about 1 L, about 15 mL to about 900 mL, about 15 mL to about 800 mL, about 15 mL to about 700 mL, about 15 mL to about 600 mL, about 15 mL to about 500 mL, about 15 mL to about 450 mL, about 15 mL to about 400 mL, about 15 mL to about 350 mL, about 15 mL to about 300 mL, about 15 mL to about 250 mL, about 15 mL to about 200 mL, about 15 mL to about 150 mL, about 15 mL to about 100 mL, about 15 mL to about 80 mL, about 15 mL to about 60 mL, about 15 mL to about 50 mL, about 15 mL to about 40 mL, about 15 mL to about 30 mL, about 15 mL to about 25 mL, about 15 mL to about 20 mL, about 20 mL to about 5 L, about 20 mL to about 4.5 L, about 20 mL to about 4.0 L, about 20 mL to about 3.5 L, about 20 mL to about 3.0 L, about 20 mL to about 2.5 L, about 20 mL to about 2 L, about 20 mL to about 1.5 L, about 20 mL to about 1 L, about 20 mL to about 900 mL, about 20 mL to about 800 mL, about 20 mL to about 700 mL, about 20 mL to about 600 mL, about 20 mL to about 500 mL, about 20 mL to about 450 mL, about 20 mL to about 400 mL, about 20 mL to about 350 mL, about 20 mL to about 300 mL, about 20 mL to about 250 mL, about 20 mL to about 200 mL, about 20 mL to about 150 mL, about 20 mL to about 100 mL, about 20 mL to about 80 mL, about 20 mL to about 60 mL, about 20 mL to about 50 mL, about 20 mL to about 40 mL, about 20 mL to about 30 mL, about 20 mL to about 25 mL, about 25 mL to about 5 L, about 25 mL to about 4.5 L, about 25 mL to about 4.0 L, about 25 mL to about 3.5 L, about 25 mL to about 3.0 L, about 25 mL to about 2.5 L, about 25 mL to about 2 L, about 25 mL to about 1.5 L, about 25 mL to about 1 L, about 25 mL to about 900 mL, about 25 mL to about 800 mL, about 25 mL to about 700 mL, about 25 mL to about 600 mL, about 25 mL to about 500 mL, about 25 mL to about 450 mL, about 25 mL to about 400 mL, about 25 mL to about 350 mL, about 25 mL to about 300 mL, about 25 mL to about 250 mL, about 25 mL to about 200 mL, about 25 mL to about 150 mL, about 25 mL to about 100 mL, about 25 mL to about 80 mL, about 25 mL to about 60 mL, about 25 mL to about 50 mL, about 25 mL to about 40 mL, about 25 mL to about 30 mL, about 30 mL to about 5 L, about 30 mL to about 4.5 L, about 30 mL to about 4.0 L, about 30 mL to about 3.5 L, about 30 mL to about 3.0 L, about 30 mL to about 2.5 L, about 30 mL to about 2 L, about 30 mL to about 1.5 L, about 30 mL to about 1 L, about 30 mL to about 900 mL, about 30 mL to about 800 mL, about 30 mL to about 700 mL, about 30 mL to about 600 mL, about 30 mL to about 500 mL, about 30 mL to about 450 mL, about 30 mL to about 400 mL, about 30 mL to about 350 mL, about 30 mL to about 300 mL, about 30 mL to about 250 mL, about 30 mL to about 200 mL, about 30 mL to about 150 mL, about 30 mL to about 100 mL, about 30 mL to about 80 mL, about 30 mL to about 60 mL, about 30 mL to about 50 mL, about 30 mL to about 40 mL, about 40 mL to about 5 L, about 40 mL to about 4.5 L, about 40 mL to about 4.0 L, about 40 mL to about 3.5 L, about 40 mL to about 3.0 L, about 40 mL to about 2.5 L, about 40 mL to about 2 L, about 40 mL to about 1.5 L, about 40 mL to about 1 L, about 40 mL to about 900 mL, about 40 mL to about 800 mL, about 40 mL to about 700 mL, about 40 mL to about 600 mL, about 40 mL to about 500 mL, about 40 mL to about 450 mL, about 40 mL to about 400 mL, about 40 mL to about 350 mL, about 40 mL to about 300 mL, about 40 mL to about 250 mL, about 40 mL to about 200 mL, about 40 mL to about 150 mL, about 40 mL to about 100 mL, about 40 mL to about 80 mL, about 40 mL to about 60 mL, about 40 mL to about 50 mL, about 50 mL to about 5 L, about 50 mL to about 4.5 L, about 50 mL to about 4.0 L, about 50 mL to about 3.5 L, about 50 mL to about 3.0 L, about 50 mL to about 2.5 L, about 50 mL to about 2 L, about 50 mL to about 1.5 L, about 50 mL to about 1 L, about 50 mL to about 900 mL, about 50 mL to about 800 mL, about 50 mL to about 700 mL, about 50 mL to about 600 mL, about 50 mL to about 500 mL, about 50 mL to about 450 mL, about 50 mL to about 400 mL, about 50 mL to about 350 mL, about 50 mL to about 300 mL, about 50 mL to about 250 mL, about 50 mL to about 200 mL, about 50 mL to about 150 mL, about 50 mL to about 100 mL, about 50 mL to about 80 mL, about 50 mL to about 60 mL, about 60 mL to about 5 L, about 60 mL to about 4.5 L, about 60 mL to about 4.0 L, about 60 mL to about 3.5 L, about 60 mL to about 3.0 L, about 60 mL to about 2.5 L, about 60 mL to about 2 L, about 60 mL to about 1.5 L, about 60 mL to about 1 L, about 60 mL to about 900 mL, about 60 mL to about 800 mL, about 60 mL to about 700 mL, about 60 mL to about 600 mL, about 60 mL to about 500 mL, about 60 mL to about 450 mL, about 60 mL to about 400 mL, about 60 mL to about 350 mL, about 60 mL to about 300 mL, about 60 mL to about 250 mL, about 60 mL to about 200 mL, about 60 mL to about 150 mL, about 60 mL to about 100 mL, about 60 mL to about 80 mL, about 80 mL to about 5 L, about 80 mL to about 4.5 L, about 80 mL to about 4.0 L, about 80 mL to about 3.5 L, about 80 mL to about 3.0 L, about 80 mL to about 2.5 L, about 80 mL to about 2 L, about 80 mL to about 1.5 L, about 80 mL to about 1 L, about 80 mL to about 900 mL, about 80 mL to about 800 mL, about 80 mL to about 700 mL, about 80 mL to about 600 mL, about 80 mL to about 500 mL, about 80 mL to about 450 mL, about 80 mL to about 400 mL, about 80 mL to about 350 mL, about 80 mL to about 300 mL, about 80 mL to about 250 mL, about 80 mL to about 200 mL, about 80 mL to about 150 mL, about 80 mL to about 100 mL, about 100 mL to about 5 L, about 100 mL to about 4.5 L, about 100 mL to about 4.0 L, about 100 mL to about 3.5 L, about 100 mL to about 3.0 L, about 100 mL to about 2.5 L, about 100 mL to about 2 L, about 100 mL to about 1.5 L, about 100 mL to about 1 L, about 100 mL to about 900 mL, about 100 mL to about 800 mL, about 100 mL to about 700 mL, about 100 mL to about 600 mL, about 100 mL to about 500 mL, about 100 mL to about 450 mL, about 100 mL to about 400 mL, about 100 mL to about 350 mL, about 100 mL to about 300 mL, about 100 mL to about 250 mL, about 100 mL to about 200 mL, about 100 mL to about 150 mL, about 150 mL to about 5 L, about 150 mL to about 4.5 L, about 150 mL to about 4.0 L, about 150 mL to about 3.5 L, about 150 mL to about 3.0 L, about 150 mL to about 2.5 L, about 150 mL to about 2 L, about 150 mL to about 1.5 L, about 150 mL to about 1 L, about 150 mL to about 900 mL, about 150 mL to about 800 mL, about 150 mL to about 700 mL, about 150 mL to about 600 mL, about 150 mL to about 500 mL, about 150 mL to about 450 mL, about 150 mL to about 400 mL, about 150 mL to about 350 mL, about 150 mL to about 300 mL, about 150 mL to about 250 mL, about 150 mL to about 200 mL, about 200 mL to about 5 L, about 200 mL to about 4.5 L, about 200 mL to about 4.0 L, about 200 mL to about 3.5 L, about 200 mL to about 3.0 L, about 200 mL to about 2.5 L, about 200 mL to about 2 L, about 200 mL to about 1.5 L, about 200 mL to about 1 L, about 200 mL to about 900 mL, about 200 mL to about 800 mL, about 200 mL to about 700 mL, about 200 mL to about 600 mL, about 200 mL to about 500 mL, about 200 mL to about 450 mL, about 200 mL to about 400 mL, about 200 mL to about 350 mL, about 200 mL to about 300 mL, about 200 mL to about 250 mL, about 250 mL to about 5 L, about 250 mL to about 4.5 L, about 250 mL to about 4.0 L, about 250 mL to about 3.5 L, about 250 mL to about 3.0 L, about 250 mL to about 2.5 L, about 250 mL to about 2 L, about 250 mL to about 1.5 L, about 250 mL to about 1 L, about 250 mL to about 900 mL, about 250 mL to about 800 mL, about 250 mL to about 700 mL, about 250 mL to about 600 mL, about 250 mL to about 500 mL, about 250 mL to about 450 mL, about 250 mL to about 400 mL, about 250 mL to about 350 mL, about 250 mL to about 300 mL, about 300 mL to about 5 L, about 300 mL to about 4.5 L, about 300 mL to about 4.0 L, about 300 mL to about 3.5

L, about 300 mL to about 3.0 L, about 300 mL to about 2.5 L, about 300 mL to about 2 L, about 300 mL to about 1.5 L, about 300 mL to about 1 L, about 300 mL to about 900 mL, about 300 mL to about 800 mL, about 300 mL to about 700 mL, about 300 mL to about 600 mL, about 300 mL to about 500 mL, about 300 mL to about 450 mL, about 300 mL to about 400 mL, about 300 mL to about 350 mL, about 350 mL to about 5 L, about 350 mL to about 4.5 L, about 350 mL to about 4.0 L, about 350 mL to about 3.5 L, about 350 mL to about 3.0 L, about 350 mL to about 2.5 L, about 350 mL to about 2 L, about 350 mL to about 1.5 L, about 350 mL to about 1 L, about 350 mL to about 900 mL, about 350 mL to about 800 mL, about 350 mL to about 700 mL, about 350 mL to about 600 mL, about 350 mL to about 500 mL, about 350 mL to about 450 mL, about 350 mL to about 400 mL, about 400 mL to about 5 L, about 400 mL to about 4.5 L, about 400 mL to about 4.0 L, about 400 mL to about 3.5 L, about 400 mL to about 3.0 L, about 400 mL to about 2.5 L, about 400 mL to about 2 L, about 400 mL to about 1.5 L, about 400 mL to about 1 L, about 400 mL to about 900 mL, about 400 mL to about 800 mL, about 400 mL to about 700 mL, about 400 mL to about 600 mL, about 400 mL to about 500 mL, about 400 mL to about 450 mL, about 450 mL to about 5 L, about 450 mL to about 4.5 L, about 450 mL to about 4.0 L, about 450 mL to about 3.5 L, about 450 mL to about 3.0 L, about 450 mL to about 2.5 L, about 450 mL to about 2 L, about 450 mL to about 1.5 L, about 450 mL to about 1 L, about 450 mL to about 900 mL, about 450 mL to about 800 mL, about 450 mL to about 700 mL, about 450 mL to about 600 mL, about 450 mL to about 500 mL, about 500 mL to about 5 L, about 500 mL to about 4.5 L, about 500 mL to about 4.0 L, about 500 mL to about 3.5 L, about 500 mL to about 3.0 L, about 500 mL to about 2.5 L, about 500 mL to about 2 L, about 500 mL to about 1.5 L, about 500 mL to about 1 L, about 500 mL to about 900 mL, about 500 mL to about 800 mL, about 500 mL to about 700 mL, about 500 mL to about 600 mL, about 600 mL to about 5 L, about 600 mL to about 4.5 L, about 600 mL to about 4.0 L, about 600 mL to about 3.5 L, about 600 mL to about 3.0 L, about 600 mL to about 2.5 L, about 600 mL to about 2 L, about 600 mL to about 1.5 L, about 600 mL to about 1 L, about 600 mL to about 900 mL, about 600 mL to about 800 mL, about 600 mL to about 700 mL, about 700 mL to about 5 L, about 700 mL to about 4.5 L, about 700 mL to about 4.0 L, about 700 mL to about 3.5 L, about 700 mL to about 3.0 L, about 700 mL to about 2.5 L, about 700 mL to about 2 L, about 700 mL to about 1.5 L, about 700 mL to about 1 L, about 700 mL to about 900 mL, about 700 mL to about 800 mL, about 800 mL to about 5 L, about 800 mL to about 4.5 L, about 800 mL to about 4.0 L, about 800 mL to about 3.5 L, about 800 mL to about 3.0 L, about 800 mL to about 2.5 L, about 800 mL to about 2 L, about 800 mL to about 1.5 L, about 800 mL to about 1 L, about 800 mL to about 900 mL, about 900 mL to about 5 L, about 900 mL to about 4.5 L, about 900 mL to about 4.0 L, about 900 mL to about 3.5 L, about 900 mL to about 3.0 L, about 900 mL to about 2.5 L, about 900 mL to about 2 L, about 900 mL to about 1.5 L, about 900 mL to about 1 L, about 1 L to about 5 L, about 1 L to about 4.5 L, about 1 L to about 4.0 L, about 1 L to about 3.5 L, about 1 L to about 3.0 L, about 1 L to about 2.5 L, about 1 L to about 2 L, about 1 L to about 1.5 L, about 1.5 L to about 5 L, about 1.5 L to about 4.5 L, about 1.5 L to about 4.0 L, about 1.5 L to about 3.5 L, about 1.5 L to about 3.0 L, about 1.5 L to about 2.5 L, about 1.5 L to about 2 L, about 2 L to about 5 L, about 2 L to about 4.5 L, about 2 L to about 4.0 L, about 2 L to about 3.5 L, about 2 L to about 3.0 L, about 2 L to about 2.5 L, about 2.5 L to about 5 L, about 2.5 L to about 4.5 L, about 2.5 L to about 4.0 L, about 2.5 L to about 3.5 L, about 2.5 L to about 3.0 L, about 3.0 L to about 5 L, about 3.0 L to about 4.5 L, about 3.0 L to about 4.0 L, about 3.0 L to about 3.5 L, about 3.5 L to about 5 L, about 3.5 L to about 4.5 L, about 3.5 L to about 4.0 L, about 4.0 L to about 5 L, about 4.0 L to about 4.5 L, or about 4.5 L to about 5.0 L. In some embodiments, the ratio of the height to the width of the test culture vessel is about the same as the ratio of the height to the width of the production bioreactor.

In some embodiments, the volume of liquid culture medium disposed in the test culture vessel (during culturing) can range from about 0.5 mL to about 1.5 L, about 0.5 mL to about 1.4 L, about 0.5 mL to about 1.3 L, about 0.5 mL to about 1.2 L, about 0.5 mL to about 1.1 L, about 0.5 mL to about 1.0 L, about 0.5 mL to about 900 mL, about 0.5 mL to about 800 mL, about 0.5 mL to about 700 mL, about 0.5 mL to about 600 mL, about 0.5 mL to about 500 mL, about 0.5 mL to about 400 mL, about 0.5 mL to about 300 mL, about 0.5 mL to about 250 mL, about 0.5 mL to about 200 mL, about 0.5 mL to about 150 mL, about 0.5 mL to about 100 mL, about 0.5 mL to about 80 mL, about 0.5 mL to about 60 mL, about 0.5 mL to about 50 mL, about 0.5 mL to about 40 mL, about 0.5 mL to about 30 mL, about 0.5 mL to about 25 mL, about 0.5 mL to about 20 mL, about 0.5 mL to about 10 mL, about 0.5 mL to about 5 mL, about 0.5 mL to about 2.5 mL, about 2.5 mL to about 1.5 L, about 2.5 mL to about 1.4 L, about 2.5 mL to about 1.3 L, about 0.5 mL to about 1.2 L, about 0.5 mL to about 1.1 L, about 0.5 mL to about 1.0 L, about 2.5 mL to about 900 mL, about 2.5 mL to about 800 mL, about 2.5 mL to about 700 mL, about 2.5 mL to about 600 mL, about 2.5 mL to about 500 mL, about 2.5 mL to about 400 mL, about 2.5 mL to about 300 mL, about 2.5 mL to about 250 mL, about 2.5 mL to about 200 mL, about 2.5 mL to about 150 mL, about 2.5 mL to about 100 mL, about 2.5 mL to about 80 mL, about 2.5 mL to about 60 mL, about 2.5 mL to about 50 mL, about 2.5 mL to about 40 mL, about 2.5 mL to about 30 mL, about 2.5 mL to about 25 mL, about 2.5 mL to about 20 mL, about 2.5 mL to about 10 mL, about 2.5 mL to about 5 mL, about 5 mL to about 1.5 L, about 5 mL to about 1.4 L, about 5 mL to about 1.3 L, about 5 mL to about 1.2 L, about 5 mL to about 1.1 L, about 5 mL to about 1.0 L, about 5 mL to about 900 mL, about 5 mL to about 800 mL, about 5 mL to about 700 mL, about 5 mL to about 600 mL, about 5 mL to about 500 mL, about 5 mL to about 400 mL, about 5 mL to about 300 mL, about 5 mL to about 250 mL, about 5 mL to about 200 mL, about 5 mL to about 150 mL, about 5 mL to about 100 mL, about 5 mL to about 80 mL, about 5 mL to about 60 mL, about 5 mL to about 50 mL, about 5 mL to about 40 mL, about 5 mL to about 30 mL, about 5 mL to about 25 mL, about 5 mL to about 20 mL, about 5 mL to about 10 mL, about 10 mL to about 1.5 L, about 10 mL to about 1.4 L, about 10 mL to about 1.3 L, about 10 mL to about 1.2 L, about 10 mL to about 1.1 L, about 10 mL to about 1.0 L, about 10 mL to about 900 mL, about 10 mL to about 800 mL, about 10 mL to about 700 mL, about 10 mL to about 600 mL, about 10 mL to about 500 mL, about 10 mL to about 400 mL, about 10 mL to about 300 mL, about 10 mL to about 250 mL, about 10 mL to about 200 mL, about 10 mL to about 150 mL, about 10 mL to about 100 mL, about 10 mL to about 80 mL, about 10 mL to about 60 mL, about 10 mL to about 50 mL, about 10 mL to about 40 mL, about 10 mL to about 30 mL, about 10 mL to about 25 mL, about 10 mL to about 20 mL, about 20 mL to about 1.5 L, about 20 mL to about 1.4 L, about 20 mL to about 1.3 L, about 20 mL to about 1.2 L, about 20 mL to about 1.1 L, about 20 mL to about 1.0 L, about 20 mL to about 900 mL, about 20 mL to about 800 mL, about 20 mL to about 700 mL, about 20 mL to about 600 mL, about 20 mL to about 500 mL, about 20 mL to about 400 mL, about 20 mL to about 300 mL, about 20 mL to about 250 mL, about 20 mL to about 200 mL, about 20 mL to about 150 mL, about 20 mL to about 100 mL, about 20 mL to about 80 mL, about 20 mL to about 60 mL, about 20 mL to about 50 mL, about 20 mL to about 40 mL, about 20 mL to about 30 mL, about 20 mL to about 25 mL, about 25 mL to about 1.5 L, about 25 mL to about 1.4 L, about 25 mL to about 1.3 L, about 25 mL to about 1.2 L, about 25 mL to about 1.1 L, about 25 mL to about 1.0 L, about 25 mL to about 900 mL, about 25 mL to about 800 mL, about 25 mL to about 700 mL, about 25 mL to about 600 mL, about 25 mL to about 500 mL, about 25 mL to about 400 mL, about 25 mL to about 300 mL, about 25 mL to about 250 mL, about 25 mL to about 200 mL, about 25 mL to about 150 mL, about 25 mL to about 100 mL, about 25 mL to about 80 mL, about 25 mL to about 60 mL, about 25 mL to about 50 mL, about 25 mL to about 40 mL, about 25 mL to about 30 mL, about 30 mL to about 1.5 L, about 30 mL to about 1.4 L, about 30 mL to about 1.3 L, about 30 mL to about 1.2 L, about 30 mL to about 1.1 L, about 30 mL to about 1.0 L, about 30 mL to about 900 mL, about 30 mL to about 800 mL, about 30 mL to about 700 mL, about 30 mL to about 600 mL, about 30 mL to about 500 mL, about 30 mL to about 400 mL, about 30 mL to about 300 mL, about 30 mL to about 250 mL, about 30 mL to about 200 mL, about 30 mL to about 150 mL, about 30 mL to about 100 mL, about 30 mL to about 80 mL, about 30 mL to about 60 mL, about 30 mL to about 50 mL, about 30 mL to about 40 mL, about 40 mL to about 1.5 L, about 40 mL to about 1.4 L, about 40 mL to about 1.3 L, about 40 mL to about 1.2 L, about 40 mL to about 1.1 L, about 40 mL to about 1.0 L, about 40 mL to about 900 mL, about 40 mL to about 800 mL, about 40 mL to about 700 mL, about 40 mL to about 600 mL, about 40 mL to about 500 mL, about 40 mL to about 400 mL, about 40 mL to about 300 mL, about 40 mL to about 250 mL, about 40 mL to about 200 mL, about 40 mL to about 150 mL, about 40 mL to about 100 mL, about 40 mL to about 80 mL, about 40 mL to about 60 mL, about 40 mL to about 50 mL, about 50 mL to about 1.5 L, about 50 mL to about 1.4 L, about 50 mL to about 1.3 L, about 50 mL to about 1.2 L, about 50 mL to about 1.1 L, about 50 mL to about 1.0 L, about 50 mL to about 900 mL, about 50 mL to about 800 mL, about 50 mL to about 700 mL, about 50 mL to about 600 mL, about 50 mL to about 500 mL, about 50 mL to about 400 mL, about 50 mL to about 300 mL, about 50 mL to about 250 mL, about 50 mL to about 200 mL, about 50 mL to about 150 mL, about 50 mL to about 100 mL, about 50 mL to about 80 mL, about 50 mL to about 60 mL, about 60 mL to about 1.5 L, about 60 mL to about 1.4 L, about 60 mL to about 1.3 L, about 60 mL to about 1.2 L, about 60 mL to about 1.1 L, about 60 mL to about 1.0 L, about 60 mL to about 900 mL, about 60 mL to about 800 mL, about 60 mL to about 700 mL, about 60 mL to about 600 mL, about 60 mL to about 500 mL, about 60 mL to about 400 mL, about 60 mL to about 300 mL, about 60 mL to about 250 mL, about 60 mL to about 200 mL, about 60 mL to about 150 mL, about 60 mL to about 100 mL, about 60 mL to about 80 mL, about 80 mL to about 1.5 L, about 80 mL to about 1.4 L, about 80 mL to about 1.3 L, about 80 mL to about 1.2 L, about 80 mL to about 1.1 L, about 80 mL to about 1.0 L, about 80 mL to about 900 mL, about 80 mL to about 800 mL, about 80 mL to about 700 mL, about 80 mL to about 600 mL, about 80 mL to about 500 mL, about 80 mL to about 400 mL, about 80 mL to about 300 mL, about 80 mL to about 250 mL, about 80 mL to about 200 mL, about 80 mL to about 150 mL, about 80 mL to about 100 mL, about 100 mL to about 1.5 L, about 100 mL to about 1.4 L, about 100 mL to about 1.3 L, about 100 mL to about 1.2 L, about 100 mL to about 1.1 L, about 100 mL to about 1.0 L, about 100 mL to about 900 mL, about 100 mL to about 800 mL, about 100 mL to about 700 mL, about 100 mL to about 600 mL, about 100 mL to about 500 mL, about 100 mL to about 400 mL, about 100 mL to about 300 mL, about 100 mL to about 250 mL, about 100 mL to about 200 mL, about 100 mL to about 150 mL, about 150 mL to about 1.5 L, about 150 mL to about 1.4 L, about 150 mL to about 1.3 L, about 150 mL to about 1.2 L, about 150 mL to about 1.1 L, about 150 mL to about 1.0 L, about 150 mL to about 900 mL, about 150 mL to about 800 mL, about 150 mL to about 700 mL, about 150 mL to about 600 mL, about 150 mL to about 500 mL, about 150 mL to about 400 mL, about 150 mL to about 300 mL, about 150 mL to about 250 mL, about 150 mL to about 200 mL, about 200 mL to about 1.5 L, about 200 mL to about 1.4 L, about 200 mL to about 1.3 L, about 200 mL to about 1.2 L, about 200 mL to about 1.1 L, about 200 mL to about 1.0 L, about 200 mL to about 900 mL, about 200 mL to about 800 mL, about 200 mL to about 700 mL, about 200 mL to about 600 mL, about 200 mL to about 500 mL, about 200 mL to about 400 mL, about 200 mL to about 300 mL, about 200 mL to about 250 mL, about 250 mL to about 1.5 L, about 250 mL to about 1.4 L, about 250 mL to about 1.3 L, about 250 mL to about 1.2 L, about 250 mL to about 1.1 L, about 250 mL to about 1.0 L, about 250 mL to about 900 mL, about 250 mL to about 800 mL, about 250 mL to about 700 mL, about 250 mL to about 600 mL, about 250 mL to about 500 mL, about 250 mL to about 400 mL, about 250 mL to about 300 mL, about 300 mL to about 1.5 L, about 300 mL to about 1.4 L, about 300 mL to about 1.3 L, about 300 mL to about 1.2 L, about 300 mL to about 1.1 L, about 300 mL to about 1.0 L, about 300 mL to about 900 mL, about 300 mL to about 800 mL, about 300 mL to about 700 mL, about 300 mL to about 600 mL, about 300 mL to about 500 mL, about 300 mL to about 400 mL, about 400 mL to about 1.5 L, about 400 mL to about 1.4 L, about 400 mL to about 1.3 L, about 400 mL to about 1.2 L, about 400 mL to about 1.1 L, about 400 mL to about 1.0 L, about 400 mL to about 900 mL, about 400 mL to about 800 mL, about 400 mL to about 700 mL, about 400 mL to about 600 mL, about 400 mL to about 500 mL, about 500 mL to about 1.5 L, about 500 mL to about 1.4 L, about 500 mL to about 1.3 L, about 500 mL to about 1.2 L, about 500 mL to about 1.1 L, about 500 mL to about 1.0 L, about 500 mL to about 900 mL, about 500 mL to about 800 mL, about 500 mL to about 700 mL, about 500 mL to about 600 mL, about 600 mL to about 1.5 L, about 600 mL to about 1.4 L, about 600 mL to about 1.3 L, about 600 mL to about 1.2 L, about 600 mL to about 1.1 L, about 600 mL to about 1.0 L, about 600 mL to about 900 mL, about 600 mL to about 800 mL, about 600 mL to about 700 mL, about 700 mL to about 1.5 L, about 700 mL to about 1.4 L, about 700 mL to about 1.3 L, about 700 mL to about 1.2 L, about 700 mL to about 1.1 L, about 700 mL to about 1.0 L, about 700 mL to about 900 mL, about 700 mL to about 800 mL, about 800 mL to about 1.5 L, about 800 mL to about 1.4 L, about 800 mL to about 1.3 L, about 800 mL to about 1.2 L, about 800 mL to about 1.1 L, about 800 mL to about 1.0 L, about 800 mL to about 900 mL, about 900 mL to about 1.5 L, about 900 mL to about 1.4 L, about 900 mL to about 1.3 L, about 900 mL to about 1.2 L, about 900 mL to about 1.1 L, about 900 mL to about 1.0 L, about 1.0 L to about 1.5 L, about 1.0 L to about 1.4 L, about 1.0 L to about 1.3 L, about 1.0 L to about 1.2 L, about 1.0 L to about 1.1 L, about 1.1 L to about 1.5 L, about 1.1 L to about 1.4

L, about 1.1 L to about 1.3 L, about 1.1 L to about 1.2 L, about 1.2 L to about 1.5 L, about 1.2 L to about 1.4 L, about 1.2 L to about 1.3 L, about 1.3 L to about 1.5 L, about 1.3 L to about 1.4 L, or about 1.4 L to about 1.5 L.

In some embodiments, the test culture vessel is a shake flask, e.g., a baffled shake flask. A shake flask can have a volume, for example, of about 250 mL to about 300 mL, about 300 mL to about 400 mL, or about 400 mL to about 500 mL. The shake flask can include at least one gas permeable surface (e.g., at least one surface having a gas permeable membrane which may also act as a sterile barrier) and/or at least one vented cap. A shake flask may have on its outer surface a structure that allows the shake flask to be stably placed in a tissue culture incubator (e.g., a rotary incubator).

The interior surface of a shake flask may have at least one coating (e.g., at least one coating of gelatin, collagen, poly-L-ornithine, polystyrene, and laminin). Exemplary shake flasks that can be used in any of the methods described herein can be purchased from Corning Inc. (Tewsbury, Mass.), Presens (Brondby, Denmark), Nalge-Nunc International (Rochester, N.Y.). Exemplary shake flasks include baffled shake flasks or Erlenmeyer flasks, or any art-recognized modified versions thereof. Additional examples of shake flasks (e.g., different shapes and dimensions of shake flasks) and interior surface coatings of shake flasks are known in the art and can be used in the present methods.

In some embodiments, the test culture vessel can have a rotary agitation of about 125 RPM to about 400 RPM (e.g., about 150 RPM to about 350 RPM, or about 200 RPM to about 300 RPM). For example, the test culture vessel can have a rotary agitation of about 125 RPM to about 400 RPM, about 125 RPM to about 380 RPM, about 125 RPM to about 360 RPM, about 125 RPM to about 340 RPM, about 125 RPM to about 320 RPM, about 125 RPM to about 300 RPM, about 125 RPM to about 280 RPM, about 125 RPM to about 260 RPM, about 125 RPM to about 240 RPM, about 125 RPM to about 220 RPM, about 125 RPM to about 200 RPM, about 125 RPM to about 180 RPM, about 125 RPM to about 160 RPM, about 125 RPM to about 140 RPM, about 140 RPM to about 400 RPM, about 140 RPM to about 380 RPM, about 140 RPM to about 360 RPM, about 140 RPM to about 340 RPM, about 140 RPM to about 320 RPM, about 140 RPM to about 300 RPM, about 140 RPM to about 280 RPM, about 140 RPM to about 260 RPM, about 140 RPM to about 240 RPM, about 140 RPM to about 220 RPM, about 140 RPM to about 200 RPM, about 140 RPM to about 180 RPM, about 140 RPM to about 160 RPM, about 160 RPM to about 400 RPM, about 160 RPM to about 380 RPM, about 160 RPM to about 360 RPM, about 160 RPM to about 340 RPM, about 160 RPM to about 320 RPM, about 160 RPM to about 300 RPM, about 160 RPM to about 280 RPM, about 160 RPM to about 260 RPM, about 160 RPM to about 240 RPM, about 160 RPM to about 220 RPM, about 160 RPM to about 200 RPM, about 160 RPM to about 180 RPM, about 180 RPM to about 400 RPM, about 180 RPM to about 380 RPM, about 180 RPM to about 360 RPM, about 180 RPM to about 340 RPM, about 180 RPM to about 320 RPM, about 180 RPM to about 300 RPM, about 180 RPM to about 280 RPM, about 180 RPM to about 260 RPM, about 180 RPM to about 240 RPM, about 180 RPM to about 220 RPM, about 180 RPM to about 200 RPM, about 200 RPM to about 400 RPM, about 200 RPM to about 380 RPM, about 200 RPM to about 360 RPM, about 200 RPM to about 340 RPM, about 200 RPM to about 320 RPM, about 200 RPM to about 300 RPM, about 200 RPM to about 280 RPM, about 200 RPM to about 260 RPM, about 200 RPM to about 240 RPM, about 200 RPM to about 220 RPM, about 220 RPM to about 400 RPM, about 220 RPM to about 380 RPM, about 220 RPM to about 360 RPM, about 220 RPM to about 340 RPM, about 220 RPM to about 320 RPM, about 220 RPM to about 300 RPM, about 220 RPM to about 280 RPM, about 220 RPM to about 260 RPM, about 220 RPM to about 240 RPM, about 240 RPM to about 400 RPM, about 240 RPM to about 380 RPM, about 240 RPM to about 360 RPM, about 240 RPM to about 340 RPM, about 240 RPM to about 320 RPM, about 240 RPM to about 300 RPM, about 240 RPM to about 280 RPM, about 240 RPM to about 260 RPM, about 260 RPM to about 400 RPM, about 260 RPM to about 380 RPM, about 260 RPM to about 360 RPM, about 260 RPM to about 340 RPM, about 260 RPM to about 320 RPM, about 260 RPM to about 300 RPM, about 260 RPM to about 280 RPM, about 280 RPM to about 400 RPM, about 280 RPM to about 380 RPM, about 280 RPM to about 360 RPM, about 280 RPM to about 340 RPM, about 280 RPM to about 320 RPM, about 280 RPM to about 300 RPM, about 300 RPM to about 400 RPM, about 300 RPM to about 380 RPM, about 300 RPM to about 360 RPM, about 300 RPM to about 340 RPM, about 300 RPM to about 320 RPM, about 320 RPM to about 400 RPM, about 320 RPM to about 380 RPM, about 320 RPM to about 360 RPM, about 320 RPM to about 340 RPM, about 340 RPM to about 400 RPM, about 340 RPM to about 380 RPM, about 340 RPM to about 360 RPM, about 360 RPM to about 400 RPM, about 360 RPM to about 380 RPM, or about 380 RPM to about 400 RPM.

In some embodiments, rotary agitation of the test culture vessel can be performed using a rotary incubator with a throw (orbit) diameter of between about 25 mm to about 50 mm. In some embodiments, the test culture vessel can have a concentration of a sensitizer of about 0 ppm to about 5,000 ppm (e.g., about 0 ppm to about 120 ppm, about 30 ppm to about 120 ppm, or about 50 ppm to about 100 ppm). In some embodiments, the test culture vessel can have a concentration of a sensitizer (e.g., an antifoam, e.g., any of the antifoams described herein) of 0 ppm to about 200 ppm, 0 ppm to about 190 ppm, 0 ppm to about 180 ppm, 0 ppm to about 170 ppm, 0 ppm to about 160 ppm, 0 ppm to about 150 ppm, 0 ppm to about 140 ppm, 0 ppm to about 130 ppm, 0 ppm to about 120 ppm, 0 ppm to about 110 ppm, 0 ppm to about 100 ppm, 0 ppm, to about 90 ppm, 0 ppm to about 80 ppm, 0 ppm to about 70 ppm, 0 ppm to about 60 ppm, 0 ppm to about 50 ppm, 0 ppm to about 40 ppm, 0 ppm to about 30 ppm, 0 ppm to about 20 ppm, 0 ppm to about 10 ppm, about 10 ppm to about 200 ppm, about 10 ppm to about 190 ppm, about 10 ppm to about 180 ppm, about 10 ppm to about 170 ppm, about 10 ppm to about 160 ppm, about 10 ppm to about 150 ppm, about 10 ppm to about 140 ppm, about 10 ppm to about 130 ppm, about 10 ppm to about 120 ppm, about 10 ppm to about 110 ppm, about 10 ppm to about 100 ppm, about 10 ppm to about 90 ppm, about 10 ppm to about 80 ppm, about 10 ppm to about 70 ppm, about 10 ppm to about 60 ppm, about 10 ppm to about 50 ppm, about 10 ppm to about 40 ppm, about 10 ppm to about 30 ppm, about 10 ppm to about 20 ppm, about 20 ppm to about 200 ppm, about 20 ppm to about 190 ppm, about 20 ppm to about 180 ppm, about 20 ppm to about 170 ppm, about 20 ppm to about 160 ppm, about 20 ppm to about 150 ppm, about 20 ppm to about 140 ppm, about 20 ppm to about 130 ppm, about 20 ppm to about 120 ppm, about 20 ppm to about 110 ppm, about 20 ppm to about 100 ppm, about 20 ppm to about 90 ppm, about 20 ppm to about 80 ppm, about 20 ppm to about 70 ppm, about 20 ppm to about 60 ppm, about 20 ppm to about 50 ppm, about 20 ppm to about 40 ppm, about 20 ppm to about 30 ppm, about 30 ppm to about 200 ppm, about 30 ppm to about 190 ppm, about 30 ppm to about 180 ppm, about 30 ppm to about 170 ppm, about 30 ppm to about 160 ppm, about 30 ppm to about 150 ppm, about 30 ppm to about 140 ppm, about 30 ppm to about 130 ppm, about 30 ppm to about 120 ppm, about 30 ppm to about 110 ppm, about 30 ppm to about 100 ppm, about 30 ppm to about 90 ppm, about 30 ppm to about 80 ppm, about 30 ppm to about 70 ppm, about 30 ppm to about 60 ppm, about 30 ppm to about 50 ppm, about 30 ppm to about 40 ppm, about 40 ppm to about 200 ppm, about 40 ppm to about 190 ppm, about 40 ppm to about 180 ppm, about 40 ppm to about 170 ppm, about 40 ppm to about 160 ppm, about 40 ppm to about 150 ppm, about 40 ppm to about 140 ppm, about 40 ppm to about 130 ppm, about 40 ppm to about 120 ppm, about 40 ppm to about 110 ppm, about 40 ppm to about 100 ppm, about 40 ppm to about 90 ppm, about 40 ppm to about 80 ppm, about 40 ppm to about 70 ppm, about 40 ppm to about 60 ppm, about 40 ppm to about 50 ppm, about 50 ppm to about 200 ppm, about 50 ppm to about 190 ppm, about 50 ppm to about 180 ppm, about 50 ppm to about 170 ppm, about 50 ppm to about 160 ppm, about 50 ppm to about 150 ppm, about 50 ppm to about 140 ppm, about 50 ppm to about 130 ppm, about 50 ppm to about 120 ppm, about 50 ppm to about 110 ppm, about 50 ppm to about 100 ppm, about 50 ppm to about 90 ppm, about 50 ppm to about 80 ppm, about 50 ppm to about 70 ppm, about 50 ppm to about 60 ppm, about 60 ppm to about 200 ppm, about 60 ppm to about 190 ppm, about 60 ppm to about 180 ppm, about 60 ppm to about 170 ppm, about 60 ppm to about 160 ppm, about 60 ppm to about 150 ppm, about 60 ppm to about 140 ppm, about 60 ppm to about 130 ppm, about 60 ppm to about 120 ppm, about 60 ppm to about 110 ppm, about 60 ppm to about 100 ppm, about 60 ppm to about 90 ppm, about 60 ppm to about 80 ppm, about 60 ppm to about 70 ppm, about 70 ppm to about 200 ppm, about 70 ppm to about 190 ppm, about 70 ppm to about 180 ppm, about 70 ppm to about 170 ppm, about 70 ppm to about 160 ppm, about 70 ppm to about 150 ppm, about 70 ppm to about 140 ppm, about 70 ppm to about 130 ppm, about 70 ppm to about 120 ppm, about 70 ppm to about 110 ppm, about 70 ppm to about 100 ppm, about 70 ppm to about 90 ppm, about 70 ppm to about 80 ppm, about 80 ppm to about 200 ppm, about 80 ppm to about 190 ppm, about 80 ppm to about 180 ppm, about 80 ppm to about 170 ppm, about 80 ppm to about 160 ppm, about 80 ppm to about 150 ppm, about 80 ppm to about 140 ppm, about 80 ppm to about 130 ppm, about 80 ppm to about 120 ppm, about 80 ppm to about 110 ppm, about 80 ppm to about 100 ppm, about 80 ppm to about 90 ppm, about 90 ppm to about 200 ppm, about 90 ppm to about 190 ppm, about 90 ppm to about 180 ppm, about 90 ppm to about 170 ppm, about 90 ppm to about 160 ppm, about 90 ppm to about 150 ppm, about 90 ppm to about 140 ppm, about 90 ppm to about 130 ppm, about 90 ppm to about 120 ppm, about 90 ppm to about 110 ppm, about 90 ppm to about 100 ppm, about 100 ppm to about 200 ppm, about 100 ppm to about 190 ppm, about 100 ppm to about 180 ppm, about 100 ppm to about 170 ppm, about 100 ppm to about 160 ppm, about 100 ppm to about 150 ppm, about 100 ppm to about 140 ppm, about 100 ppm to about 130 ppm, about 100 ppm to about 120 ppm, about 100 ppm to about 110 ppm, about 110 ppm to about 200 ppm, about 110 ppm to about 190 ppm, about 110 ppm to about 180 ppm, about 110 ppm to about 170 ppm, about 110 ppm to about 160 ppm, about 110 ppm to about 150 ppm, about 110 ppm to about 140 ppm, about 110 ppm to about 130 ppm, about 110 ppm to about 120 ppm, about 120 ppm to about 200 ppm, about 120 ppm to about 190 ppm, about 120 ppm to about 180 ppm, about 120 ppm to about 170 ppm, about 120 ppm to about 160 ppm, about 120 ppm to about 150 ppm, about 120 ppm to about 140 ppm, about 120 ppm to about 130 ppm, about 130 ppm to about 200 ppm, about 130 ppm to about 190 ppm, about 130 ppm to about 180 ppm, about 130 ppm to about 170 ppm, about 130 ppm to about 160 ppm, about 130 ppm to about 150 ppm, about 130 ppm to about 140 ppm, about 140 ppm to about 200 ppm, about 140 ppm to about 190 ppm, about 140 ppm to about 180 ppm, about 140 ppm to about 170 ppm, about 140 ppm to about 160 ppm, about 140 ppm to about 150 ppm, about 150 ppm to about 200 ppm, about 150 ppm to about 190 ppm, about 150 ppm to about 180 ppm, about 150 ppm to about 170 ppm, about 150 ppm to about 160 ppm, about 160 ppm to about 200 ppm, about 160 ppm to about 190 ppm, about 160 ppm to about 180 ppm, about 160 ppm to about 170 ppm, about 170 ppm to about 200 ppm, about 170 ppm to about 190 ppm, about 170 ppm to about 180 ppm, about 180 ppm to about 200 ppm, about 180 ppm to about 190 ppm, or about 190 ppm to about 200 ppm (where the sensitizer is present in a liquid culture medium disposed in the test culture vessel, e.g., for a period of time during the culturing).

In some embodiments, the test culture vessel can have a concentration of a sensitizer (e.g., an antifoam, e.g., any of the antifoams described herein) of 0 ppm to about 5,000 ppm, 0 ppm to about 4,500 ppm, 0 ppm to about 4,000 ppm, 0 ppm to about 3,500 ppm, 0 ppm to about 3,000 ppm, 0 ppm to about 2,500 ppm, 0 ppm to about 2,000 ppm, 0 ppm to about 1,500 ppm, 0 ppm to about 1,000 ppm, 0 ppm to about 800 ppm, 0 ppm to about 600 ppm, 0 ppm to about 500 ppm, 0 ppm to about 450 ppm, 0 ppm to about 400 ppm, 0 ppm to about 350 ppm, 0 ppm to about 300 ppm, 0 ppm to about 250 ppm, 0 ppm to about 200 ppm, 0 ppm to about 150 ppm, 0 ppm to about 140 ppm, 0 ppm to about 120 ppm, 0 ppm to about 100 ppm, 0 ppm to about 80 ppm, 0 ppm to about 60 ppm, 0 ppm to about 50 ppm, 0 ppm to about 40 ppm, 0 ppm to about 30 ppm, 0 ppm to about 20 ppm, 0 ppm to about 10 ppm, about 10 ppm to about 5,000 ppm, about 10 ppm to about 4,500 ppm, about 10 ppm to about 4,000 ppm, about 10 ppm to about 3,500 ppm, about 10 ppm to about 3,000 ppm, about 10 ppm to about 2,500 ppm, about 10 ppm to about 2,000 ppm, about 10 ppm to about 1,500 ppm, about 10 ppm to about 1,000 ppm, about 10 ppm to about 800 ppm, about 10 ppm to about 600 ppm, about 10 ppm to about 500 ppm, about 10 ppm to about 450 ppm, about 10 ppm to about 400 ppm, about 10 ppm to about 350 ppm, about 10 ppm to about 300 ppm, about 10 ppm to about 250 ppm, about 10 ppm to about 200 ppm, about 10 ppm to about 150 ppm, about 10 ppm to about 140 ppm, about 10 ppm to about 120 ppm, about 10 ppm to about 100 ppm, about 10 ppm to about 80 ppm, about 10 ppm to about 60 ppm, about 10 ppm to about 50 ppm, about 10 ppm to about 40 ppm, about 10 ppm to about 30 ppm, about 10 ppm to about 20 ppm, about 20 ppm to about 5,000 ppm, about 20 ppm to about 4,500 ppm, about 20 ppm to about 4,000 ppm, about 20 ppm to about 3,500 ppm, about 20 ppm to about 3,000 ppm, about 20 ppm to about 2,500 ppm, about 20 ppm to about 2,000 ppm, about 20 ppm to about 1,500 ppm, about 20 ppm to about 1,000 ppm, about 20 ppm to about 800 ppm, about 20 ppm to about 600 ppm, about 20 ppm to about 500 ppm, about 20 ppm to about 450 ppm, about 20 ppm to about 400 ppm, about 20 ppm to about 350 ppm, about 20 ppm to about 300 ppm, about 20 ppm to about 250 ppm, about 20 ppm to about 200 ppm, about 20 ppm to about 150 ppm, about 20 ppm to about 140 ppm, about 20 ppm to about 120 ppm, about 20 ppm to about 100 ppm, about 20 ppm to about 80 ppm, about 20 ppm to about 60 ppm, about 20 ppm to about 50 ppm, about 20 ppm to about 40 ppm, about 20 ppm to about 30 ppm, about 30 ppm to about 5,000 ppm, about 30 ppm to about 4,500 ppm, about 30 ppm to about 4,000 ppm, about 30 ppm to about 3,500 ppm, about 30 ppm to about 3,000 ppm, about 30 ppm to about 2,500 ppm, about 30 ppm to about 2,000 ppm, about 30 ppm to about 1,500 ppm, about 30 ppm to about 1,000 ppm, about 30 ppm to about 800 ppm, about 30 ppm to about 600 ppm, about 30 ppm to about 500 ppm, about 30 ppm to about 450 ppm, about 30 ppm to about 400 ppm, about 30 ppm to about 350 ppm, about 30 ppm to about 300 ppm, about 30 ppm to about 250 ppm, about 30 ppm to about 200 ppm, about 30 ppm to about 150 ppm, about 30 ppm to about 140 ppm, about 30 ppm to about 120 ppm, about 30 ppm to about 100 ppm, about 30 ppm to about 80 ppm, about 30 ppm to about 60 ppm, about 30 ppm to about 50 ppm, about 30 ppm to about 40 ppm, about 40 ppm to about 5,000 ppm, about 40 ppm to about 4,500 ppm, about 40 ppm to about 4,000 ppm, about 40 ppm to about 3,500 ppm, about 40 ppm to about 3,000 ppm, about 40 ppm to about 2,500 ppm, about 40 ppm to about 2,000 ppm, about 40 ppm to about 1,500 ppm, about 40 ppm to about 1,000 ppm, about 40 ppm to about 800 ppm, about 40 ppm to about 600 ppm, about 40 ppm to about 500 ppm, about 40 ppm to about 450 ppm, about 40 ppm to about 400 ppm, about 40 ppm to about 350 ppm, about 40 ppm to about 300 ppm, about 40 ppm to about 250 ppm, about 40 ppm to about 200 ppm, about 40 ppm to about 150 ppm, about 40 ppm to about 140 ppm, about 40 ppm to about 120 ppm, about 40 ppm to about 100 ppm, about 40 ppm to about 80 ppm, about 40 ppm to about 60 ppm, about 40 ppm to about 50 ppm, about 50 ppm to about 5,000 ppm, about 50 ppm to about 4,500 ppm, about 50 ppm to about 4,000 ppm, about 50 ppm to about 3,500 ppm, about 50 ppm to about 3,000 ppm, about 50 ppm to about 2,500 ppm, about 50 ppm to about 2,000 ppm, about 50 ppm to about 1,500 ppm, about 50 ppm to about 1,000 ppm, about 50 ppm to about 800 ppm, about 50 ppm to about 600 ppm, about 50 ppm to about 500 ppm, about 50 ppm to about 450 ppm, about 50 ppm to about 400 ppm, about 50 ppm to about 350 ppm, about 50 ppm to about 300 ppm, about 50 ppm to about 250 ppm, about 50 ppm to about 200 ppm, about 50 ppm to about 150 ppm, about 50 ppm to about 140 ppm, about 50 ppm to about 120 ppm, about 50 ppm to about 100 ppm, about 50 ppm to about 80 ppm, about 50 ppm to about 60 ppm, about 60 ppm to about 5,000 ppm, about 60 ppm to about 4,500 ppm, about 60 ppm to about 4,000 ppm, about 60 ppm to about 3,500 ppm, about 60 ppm to about 3,000 ppm, about 60 ppm to about 2,500 ppm, about 60 ppm to about 2,000 ppm, about 60 ppm to about 1,500 ppm, about 60 ppm to about 1,000 ppm, about 60 ppm to about 800 ppm, about 60 ppm to about 600 ppm, about 60 ppm to about 500 ppm, about 60 ppm to about 450 ppm, about 60 ppm to about 400 ppm, about 60 ppm to about 350 ppm, about 60 ppm to about 300 ppm, about 60 ppm to about 250 ppm, about 60 ppm to about 200 ppm, about 60 ppm to about 150 ppm, about 60 ppm to about 140 ppm, about 60 ppm to about 120 ppm, about 60 ppm to about 100 ppm, about 60 ppm to about 80 ppm, about 80 ppm to about 5,000 ppm, about 80 ppm to about 4,500 ppm, about 80 ppm to about 4,000 ppm, about 80 ppm to about 3,500 ppm, about 80 ppm to about 3,000 ppm, about 80 ppm to about 2,500 ppm, about 80 ppm to about 2,000 ppm, about 80 ppm to about 1,500 ppm, about 80 ppm to about 1,000 ppm, about 80 ppm to about 800 ppm, about 80 ppm to about 600 ppm, about 80 ppm to about 500 ppm, about 80 ppm to about 450 ppm, about 80 ppm to about 400 ppm, about 80 ppm to about 350 ppm, about 80 ppm to about 300 ppm, about 80 ppm to about 250 ppm, about 80 ppm to about 200 ppm, about 80 ppm to about 150 ppm, about 80 ppm to about 140 ppm, about 80 ppm to about 120 ppm, about 80 ppm to about 100 ppm, about 100 ppm to about 5,000 ppm, about 100 ppm to about 4,500 ppm, about 100 ppm to about 4,000 ppm, about 100 ppm to about 3,500 ppm, about 100 ppm to about 3,000 ppm, about 100 ppm to about 2,500 ppm, about 100 ppm to about 2,000 ppm, about 100 ppm to about 1,500 ppm, about 100 ppm to about 1,000 ppm, about 100 ppm to about 800 ppm, about 100 ppm to about 600 ppm, about 100 ppm to about 500 ppm, about 100 ppm to about 450 ppm, about 100 ppm to about 400 ppm, about 100 ppm to about 350 ppm, about 100 ppm to about 300 ppm, about 100 ppm to about 250 ppm, about 100 ppm to about 200 ppm, about 100 ppm to about 150 ppm, about 100 ppm to about 140 ppm, about 100 ppm to about 120 ppm, about 120 ppm to about 5,000 ppm, about 120 ppm to about 4,500 ppm, about 120 ppm to about 4,000 ppm, about 120 ppm to about 3,500 ppm, about 120 ppm to about 3,000 ppm, about 120 ppm to about 2,500 ppm, about 120 ppm to about 2,000 ppm, about 120 ppm to about 1,500 ppm, about 120 ppm to about 1,000 ppm, about 120 ppm to about 800 ppm, about 120 ppm to about 600 ppm, about 120 ppm to about 500 ppm, about 120 ppm to about 450 ppm, about 120 ppm to about 400 ppm, about 120 ppm to about 350 ppm, about 120 ppm to about 300 ppm, about 120 ppm to about 250 ppm, about 120 ppm to about 200 ppm, about 120 ppm to about 150 ppm, about 120 ppm to about 140 ppm, about 140 ppm to about 5,000 ppm, about 140 ppm to about 4,500 ppm, about 140 ppm to about 4,000 ppm, about 140 ppm to about 3,500 ppm, about 140 ppm to about 3,000 ppm, about 140 ppm to about 2,500 ppm, about 140 ppm to about 2,000 ppm, about 140 ppm to about 1,500 ppm, about 140 ppm to about 1,000 ppm, about 140 ppm to about 800 ppm, about 140 ppm to about 600 ppm, about 140 ppm to about 500 ppm, about 140 ppm to about 450 ppm, about 140 ppm to about 400 ppm, about 140 ppm to about 350 ppm, about 140 ppm to about 300 ppm, about 140 ppm to about 250 ppm, about 140 ppm to about 200 ppm, about 140 ppm to about 150 ppm, about 150 ppm to about 5,000 ppm, about 150 ppm to about 4,500 ppm, about 150 ppm to about 4,000 ppm, about 150 ppm to about 3,500 ppm, about 150 ppm to about 3,000 ppm, about 150 ppm to about 2,500 ppm, about 150 ppm to about 2,000 ppm, about 150 ppm to about 1,500 ppm, about 150 ppm to about 1,000 ppm, about 150 ppm to about 800 ppm, about 150 ppm to about 600 ppm, about 150 ppm to about 500 ppm, about 150 ppm to about 450 ppm, about 150 ppm to about 400 ppm, about 150 ppm to about 350 ppm, about 150 ppm to about 300 ppm, about 150 ppm to about 250 ppm, about 150 ppm to about 200 ppm, about 200 ppm to about 5,000 ppm, about 200 ppm to about 4,500 ppm, about 200 ppm to about 4,000 ppm, about 200 ppm to about 3,500 ppm, about 200 ppm to about 3,000 ppm, about 200 ppm to about 2,500 ppm, about 200 ppm to about 2,000 ppm, about 200 ppm to about 1,500 ppm, about 200 ppm to about 1,000 ppm, about 200 ppm to about 800 ppm, about 200 ppm to about 600 ppm, about 200 ppm to about 500 ppm, about 200 ppm to about 450 ppm, about 200 ppm to about 400 ppm, about 200 ppm to about 350 ppm, about 200 ppm to about 300 ppm, about 200 ppm to about 250 ppm, about 250 ppm to about 5,000 ppm, about 250 ppm to about 4,500 ppm, about 250 ppm to about 4,000 ppm, about 250 ppm to about 3,500 ppm, about 250 ppm to about 3,000 ppm, about 250 ppm to about 2,500 ppm, about 250 ppm to about 2,000 ppm, about 250 ppm to about 1,500 ppm, about 250 ppm to about 1,000 ppm, about 250 ppm to about 800 ppm, about 250 ppm to about 600 ppm, about 250 ppm to about 500 ppm, about 250 ppm to about 450 ppm, about 250 ppm to about 400 ppm, about 250 ppm to about 350 ppm, about 250 ppm to about 300 ppm, about 300 ppm to about 5,000 ppm, about 300 ppm to about 4,500 ppm, about 300 ppm to about 4,000 ppm, about 300 ppm to about 3,500 ppm, about 300 ppm to about 3,000 ppm, about 300 ppm to about 2,500 ppm, about 300 ppm to about 2,000 ppm, about 300 ppm to about 1,500 ppm, about 300 ppm to about 1,000 ppm, about 300 ppm to about 800 ppm, about 300 ppm to about 600 ppm, about 300 ppm to about 500 ppm, about 300 ppm to about 450 ppm, about 300 ppm to about 400 ppm, about 300 ppm to about 350 ppm, about 350 ppm to about 5,000 ppm, about 350 ppm to about 4,500 ppm, about 350 ppm to about 4,000 ppm, about 350 ppm to about 3,500 ppm, about 350 ppm to about 3,000 ppm, about 350 ppm to about 2,500 ppm, about 350 ppm to about 2,000 ppm, about 350 ppm to about 1,500 ppm, about 350 ppm to about 1,000 ppm, about 350 ppm to about 800 ppm, about 350 ppm to about 600 ppm, about 350 ppm to about 500 ppm, about 350 ppm to about 450 ppm, about 350 ppm to about 400 ppm, about 400 ppm to about 5,000 ppm, about 400 ppm to about 4,500 ppm, about 400 ppm to about 4,000 ppm, about 400 ppm to about 3,500 ppm, about 400 ppm to about 3,000 ppm, about 400 ppm to about 2,500 ppm, about 400 ppm to about 2,000 ppm, about 400 ppm to about 1,500 ppm, about 400 ppm to about 1,000 ppm, about 400 ppm to about 800 ppm, about 400 ppm to about 600 ppm, about 400 ppm to about 500 ppm, about 400 ppm to about 450 ppm, about 450 ppm to about 5,000 ppm, about 450 ppm to about 4,500 ppm, about 450 ppm to about 4,000 ppm, about 450 ppm to about 3,500 ppm, about 450 ppm to about 3,000 ppm, about 450 ppm to about 2,500 ppm, about 450 ppm to about 2,000 ppm, about 450 ppm to about 1,500 ppm, about 450 ppm to about 1,000 ppm, about 450 ppm to about 800 ppm, about 450 ppm to about 600 ppm, about 450 ppm to about 500 ppm, about 500 ppm to about 5,000 ppm, about 500 ppm to about 4,500 ppm, about 500 ppm to about 4,000 ppm, about 500 ppm to about 3,500 ppm, about 500 ppm to about 3,000 ppm, about 500 ppm to about 2,500 ppm, about 500 ppm to about 2,000 ppm, about 500 ppm to about 1,500 ppm, about 500 ppm to about 1,000 ppm, about 500 ppm to about 800 ppm, about 500 ppm to about 600 ppm, about 600 ppm to about 5,000 ppm, about 600 ppm to about 4,500 ppm, about 600 ppm to about 4,000 ppm, about 600 ppm to about 3,500 ppm, about 600 ppm to about 3,000 ppm, about 600 ppm to about 2,500 ppm, about 600 ppm to about 2,000 ppm, about 600 ppm to about 1,500 ppm, about 600 ppm to about 1,000 ppm, about 600 ppm to about 800 ppm, about 800 ppm to about 5,000 ppm, about 800 ppm to about 4,500 ppm, about 800 ppm to about 4,000 ppm, about 800 ppm to about 3,500 ppm, about 800 ppm to about 3,000 ppm, about 800 ppm to about 2,500 ppm, about 800 ppm to about 2,000 ppm, about 800 ppm to about 1,500 ppm, about 800 ppm to about 1,000 ppm, about 1,000 ppm to about 5,000 ppm, about 1,000 ppm to about 4,500 ppm, about 1,000 ppm to about 4,000 ppm, about 1,000 ppm to about 3,500 ppm, about 1,000 ppm to about 3,000 ppm, about 1,000 ppm to about 2,500 ppm, about 1,000 ppm to about 2,000 ppm, about 1,000 ppm to about 1,500 ppm, about 1,500 ppm to about 5,000 ppm, about 1,500 ppm to about 4,500 ppm, about 1,500 ppm to about 4,000 ppm, about 1,500 ppm to about 3,500 ppm, about 1,500 ppm to about 3,000 ppm, about 1,500 ppm to about 2,500 ppm, about 1,500 ppm to about 2,000 ppm, about 2,000 ppm to about 5,000 ppm, about 2,000 ppm to about 4,500 ppm, about 2,000 ppm to about 4,000 ppm, about 2,000 ppm to about 3,500 ppm, about 2,000 ppm to about 3,000 ppm, about 2,000 ppm to about 2,500 ppm, about 2,500 ppm to about 5,000 ppm, about 2,500 ppm to about 4,500 ppm, about 2,500 ppm to about 4,000 ppm, about 2,500 ppm to about 3,500 ppm, about 2,500 ppm to about 3,000 ppm, about 3,000 ppm to about 5,000 ppm, about 3,000 ppm to about 4,500 ppm, about 3,000 ppm to about 4,000 ppm, about 3,000 ppm to about 3,500 ppm, about 3,500 ppm to about 5,000 ppm, about 3,500 ppm to about 4,500 ppm, about 3,500 ppm to about 4,000 ppm, about 4,000 ppm to about 5,000 ppm, about 4,000 ppm to about 4,500 ppm, or about 4,500 ppm to about 5,000 ppm (where the sensitizer is present in a liquid culture medium disposed in the test culture vessel, e.g., for a period of time during the culturing).

In some embodiments, the test culture vessel can have a concentration of a protectant that is about 1 g/L to about 10 g/L (e.g., from about 2 g/L to about 8 g/L, from about 3 g/L to about 7 g/L, from about 4 g/L to about 6 g/L, or about 5 g/L). In some embodiments, the test culture vessel can have a concentration of a protectant (e.g., any of the protectants described herein or known in the art) of about 1.0 g/L to about 10.0 g/L, about 1.0 g/L to about 9.5 g/L, about 1.0 g/L to about 9.0 g/L, about 1.0 g/L to about 8.5 g/L, about 1.0 g/L to about 8.0 g/L, about 1.0 g/L to about 7.5 g/L, about 1.0 g/L to about 7.0 g/L, about 1.0 g/L to about 6.5 g/L, about 1.0 g/L to about 6.0 g/L, about 1.0 g/L to about 5.5 g/L, about 1.0 g/L to about 5.0 g/L, about 1.0 g/L to about 4.5 g/L, about 1.0 g/L to about 4.0 g/L, about 1.0 g/L to about 3.5 g/L, about 1.0 g/L to about 3.0 g/L, about 1.0 g/L to about 2.5 g/L, about 1.0 g/L to about 2.0 g/L, about 1.0 g/L to about 1.5 g/L, about 1.5 g/L to about 10.0 g/L, about 1.5 g/L to about 9.5 g/L, about 1.5 g/L to about 9.0 g/L, about 1.5 g/L to about 8.5 g/L, about 1.5 g/L to about 8.0 g/L, about 1.5 g/L to about 7.5 g/L, about 1.5 g/L to about 7.0 g/L, about 1.5 g/L to about 6.5 g/L, about 1.5 g/L to about 6.0 g/L, about 1.5 g/L to about 5.5 g/L, about 1.5 g/L to about 5.0 g/L, about 1.5 g/L to about 4.5 g/L, about 1.5 g/L to about 4.0 g/L, about 1.5 g/L to about 3.5 g/L, about 1.5 g/L to about 3.0 g/L, about 1.5 g/L to about 2.5 g/L, about 1.5 g/L to about 2.0 g/L, about 2.0 g/L to about 10.0 g/L, about 2.0 g/L to about 9.5 g/L, about 2.0 g/L to about 9.0 g/L, about 2.0 g/L to about 8.5 g/L, about 2.0 g/L to about 8.0 g/L, about 2.0 g/L to about 7.5 g/L, about 2.0 g/L to about 7.0 g/L, about 2.0 g/L to about 6.5 g/L, about 2.0 g/L to about 6.0 g/L, about 2.0 g/L to about 5.5 g/L, about 2.0 g/L to about 5.0 g/L, about 2.0 g/L to about 4.5 g/L, about 2.0 g/L to about 4.0 g/L, about 2.0 g/L to about 3.5 g/L, about 2.0 g/L to about 3.0 g/L, about 2.0 g/L to about 2.5 g/L, about 2.5 g/L to about 10.0 g/L, about 2.5 g/L to about 9.5 g/L, about 2.5 g/L to about 9.0 g/L, about 2.5 g/L to about 8.5 g/L, about 2.5 g/L to about 8.0 g/L, about 2.5 g/L to about 7.5 g/L, about 2.5 g/L to about 7.0 g/L, about 2.5 g/L to about 6.5 g/L, about 2.5 g/L to about 6.0 g/L, about 2.5 g/L to about 5.5 g/L, about 2.5 g/L to about 5.0 g/L, about 2.5 g/L to about 4.5 g/L, about 2.5 g/L to about 4.0 g/L, about 2.5 g/L to about 3.5 g/L, about 2.5 g/L to about 3.0 g/L, about 3.0 g/L to about 10.0 g/L, about 3.0 g/L to about 9.5 g/L, about 3.0 g/L to about 9.0 g/L, about 3.0 g/L to about 8.5 g/L, about 3.0 g/L to about 8.0 g/L, about 3.0 g/L to about 7.5 g/L, about 3.0 g/L to about 7.0 g/L, about 3.0 g/L to about 6.5 g/L, about 3.0 g/L to about 6.0 g/L, about 3.0 g/L to about 5.5 g/L, about 3.0 g/L to about 5.0 g/L, about 3.0 g/L to about 4.5 g/L, about 3.0 g/L to about 4.0 g/L, about 3.0 g/L to about 3.5 g/L, about 3.5 g/L to about 10.0 g/L, about 3.5 g/L to about 9.5 g/L, about 3.5 g/L to about 9.0 g/L, about 3.5 g/L to about 8.5 g/L, about 3.5 g/L to about 8.0 g/L, about 3.5 g/L to about 7.5 g/L, about 3.5 g/L to about 7.0 g/L, about 3.5 g/L to about 6.5 g/L, about 3.5 g/L to about 6.0 g/L, about 3.5 g/L to about 5.5 g/L, about 3.5 g/L to about 5.0 g/L, about 3.5 g/L to about 4.5 g/L, about 3.5 g/L to about 4.0 g/L, about 4.0 g/L to about 10.0 g/L, about 4.0 g/L to about 9.5 g/L, about 4.0 g/L to about 9.0 g/L, about 4.0 g/L to about 8.5 g/L, about 4.0 g/L to about 8.0 g/L, about 4.0 g/L to about 7.5 g/L, about 4.0 g/L to about 7.0 g/L, about 4.0 g/L to about 6.5 g/L, about 4.0 g/L to about 6.0 g/L, about 4.0 g/L to about 5.5 g/L, about 4.0 g/L to about 5.0 g/L, about 4.0 g/L to about 4.5 g/L, about 4.5 g/L to about 10.0 g/L, about 4.5 g/L to about 9.5 g/L, about 4.5 g/L to about 9.0 g/L, about 4.5 g/L to about 8.5 g/L, about 4.5 g/L to about 8.0 g/L, about 4.5 g/L to about 7.5 g/L, about 4.5 g/L to about 7.0 g/L, about 4.5 g/L to about 6.5 g/L, about 4.5 g/L to about 6.0 g/L, about 4.5 g/L to about 5.5 g/L, about 4.5 g/L to about 5.0 g/L, about 5.0 g/L to about 10.0 g/L, about 5.0 g/L to about 9.5 g/L, about 5.0 g/L to about 9.0 g/L, about 5.0 g/L to about 8.5 g/L, about 5.0 g/L to about 8.0 g/L, about 5.0 g/L to about 7.5 g/L, about 5.0 g/L to about 7.0 g/L, about 5.0 g/L to about 6.5 g/L, about 5.0 g/L to about 6.0 g/L, about 5.0 g/L to about 5.5 g/L, about 5.5 g/L to about 10.0 g/L, about 5.5 g/L to about 9.5 g/L, about 5.5 g/L to about 9.0 g/L, about 5.5 g/L to about 8.5 g/L, about 5.5 g/L to about 8.0 g/L, about 5.5 g/L to about 7.5 g/L, about 5.5 g/L to about 7.0 g/L, about 5.5 g/L to about 6.5 g/L, about 5.5 g/L to about 6.0 g/L, about 6.0 g/L to about 10.0 g/L, about 6.0 g/L to about 9.5 g/L, about 6.0 g/L to about 9.0 g/L, about 6.0 g/L to about 8.5 g/L, about 6.0 g/L to about 8.0 g/L, about 6.0 g/L to about 7.5 g/L, about 6.0 g/L to about 7.0 g/L, about 6.0 g/L to about 6.5 g/L, about 6.5 g/L to about 10.0 g/L, about 6.5 g/L to about 9.5 g/L, about 6.5 g/L to about 9.0 g/L, about 6.5 g/L to about 8.5 g/L, about 6.5 g/L to about 8.0 g/L, about 6.5 g/L to about 7.5 g/L, about 6.5 g/L to about 7.0 g/L, about 7.0 g/L to about 10.0 g/L, about 7.0 g/L to about 9.5 g/L, about 7.0 g/L to about 9.0 g/L, about 7.0 g/L to about 8.5 g/L, about 7.0 g/L to about 8.0 g/L, about 7.0 g/L to about 7.5 g/L, about 7.5 g/L to about 10.0 g/L, about 7.5 g/L to about 9.5 g/L, about 7.5 g/L to about 9.0 g/L, about 7.5 g/L to about 8.5 g/L, about 7.5 g/L to about 8.0 g/L, about 8.0 g/L to about 10.0 g/L, about 8.0 g/L to about 9.5 g/L, about 8.0 g/L to about 9.0 g/L, about 8.0 g/L to about 8.5 g/L, about 8.5 g/L to about 10.0 g/L, about 8.5 g/L to about 9.5 g/L, about 8.5 g/L to about 9.0 g/L, about 9.0 g/L to about 10.0 g/L, about 9.0 g/L to about 9.5 g/L, or about 9.5 g/L to about 10.0 g/L (where the protectant is present in a liquid culture medium disposed in the test culture vessel, e.g., for a period of time during the culturing).

The production bioreactor can be a perfusion bioreactor, a fed batch bioreactor, or a concentrated fed-batch bioreactor. In some embodiments, the production bioreactor can have a volume of about 5 L to about 20,000 L (e.g., about 50 L to about 10,000 L). In some embodiments, the production bioreactor can have a volume of more than 5 L, more than 10 L, more than 50 L, more than 100 L, more than 1000 L, more than 2000 L, more than 5000 L, more than 20000 L, more than 100000 L, or more than 150000 L (e.g., more than 1000 L). In some embodiments, the production bioreactor can have a volume of about 5 L to about 20,000 L, about 5 L to about 18,000 L, about 5 L to about 16,000 L, about 5 L to about 14,000 L, about 5 L to about 12,000 L, about 5 L to about 10,000 L, about 5 L to about 9,500 L, about 5 L to about 9,000 L, about 5 L to about 8,500 L, about 5 L to about 8,000 L, about 5 L to about 7,500 L, about 5 L to about 7,000 L, about 5 L to about 6,500 L, about 5 L to about 6,000 L, about 5 L to about 5,500 L, about 5 L to about 5,000 L, about 5 L to about 4,500 L, about 5 L to about 4,000 L, about 5 L to about 3,500 L, about 5 L to about 3,000 L, about 5 L to about 2,500 L, about 5 L to about 2,000 L, about 5 L to about 1,500 L, about 5 L to about 1,000 L, about 5 L to about 900 L, about 5 L to about 800 L, about 5 L to about 700 L, about 5 L to about 600 L, about 5 L to about 500 L, about 5 L to about 400 L, about 5 L to about 300 L, about 5 L to about 250 L, about 5 L to about 200 L, about 5 L to about 150 L, about 5 L to about 100 L, about 5 L to about 80 L, about 5 L to about 60 L, about 5 L to about 50 L, about 5 L to about 25 L, about 5 L to about 10 L, about 10 L to about 20,000 L, about 10 L to about 18,000 L, about 10 L to about 16,000 L, about 10 L to about 14,000 L, about 10 L to about 12,000 L, about 10 L to about 10,000 L, about 10 L to about 9,500 L, about 10 L to about 9,000 L, about 10 L to about 8,500 L, about 10 L to about 8,000 L, about 10 L to about 7,500 L, about 10 L to about 7,000 L, about 10 L to about 6,500 L, about 10 L to about 6,000 L, about 10 L to about 5,500 L, about 10 L to about 5,000 L, about 10 L to about 4,500 L, about 10 L to about 4,000 L, about 10 L to about 3,500 L, about 10 L to about 3,000 L, about 10 L to about 2,500 L, about 10 L to about 2,000 L, about 10 L to about 1,500 L, about 10 L to about 1,000 L, about 10 L to about 900 L, about 10 L to about 800 L, about 10 L to about 700 L, about 10 L to about 600 L, about 10 L to about 500 L, about 10 L to about 400 L, about 10 L to about 300 L, about 10 L to about 250 L, about 10 L to about 200 L, about 10 L to about 150 L, about 10 L to about 100 L, about 10 L to about 80 L, about 10 L to about 60 L, about 10 L to about 50 L, about 10 L to about 25 L, about 25 L to about 20,000 L, about 25 L to about 18,000 L, about 25 L to about 16,000 L, about 25 L to about 14,000 L, about 25 L to about 12,000 L, about 25 L to about 10,000 L, about 25 L to about 9,500 L, about 25 L to about 9,000 L, about 25 L to about 8,500 L, about 25 L to about 8,000 L, about 25 L to about 7,500 L, about 25 L to about 7,000 L, about 25 L to about 6,500 L, about 25 L to about 6,000 L, about 25 L to about 5,500 L, about 25 L to about 5,000 L, about 25 L to about 4,500 L, about 25 L to about 4,000 L, about 25 L to about 3,500 L, about 25 L to about 3,000 L, about 25 L to about 2,500 L, about 25 L to about 2,000 L, about 25 L to about 1,500 L, about 25 L to about 1,000 L, about 25 L to about 900 L, about 25 L to about 800 L, about 25 L to about 700 L, about 25 L to about 600 L, about 25 L to about 500 L, about 25 L to about 400 L, about 25 L to about 300 L, about 25 L to about 250 L, about 25 L to about 200 L, about 25 L to about 150 L, about 25 L to about 100 L, about 25 L to about 80 L, about 25 L to about 60 L, about 25 L to about 50 L, about 50 L to about 20,000 L, about 50 L to about 18,000 L, about 50 L to about 16,000 L, about 50 L to about 14,000 L, about 50 L to about 12,000 L, about 50 L to about 10,000 L, about 50 L to about 9,500 L, about 50 L to about 9,000 L, about 50 L to about 8,500 L, about 50 L to about 8,000 L, about 50 L to about 7,500 L, about 50 L to about 7,000 L, about 50 L to about 6,500 L, about 50 L to about 6,000 L, about 50 L to about 5,500 L, about 50 L to about 5,000 L, about 50 L to about 4,500 L, about 50 L to about 4,000 L, about 50 L to about 3,500 L, about 50 L to about 3,000 L, about 50 L to about 2,500 L, about 50 L to about 2,000 L, about 50 L to about 1,500 L, about 50 L to about 1,000 L, about 50 L to about 900 L, about 50 L to about 800 L, about 50 L to about 700 L, about 50 L to about 600 L, about 50 L to about 500 L, about 50 L to about 400 L, about 50 L to about 300 L, about 50 L to about 250 L, about 50 L to about 200 L, about 50 L to about 150 L, about 50 L to about 100 L, about 50 L to about 80 L, about 50 L to about 60 L, about 60 L to about 20,000 L, about 60 L to about 18,000 L, about 60 L to about 16,000 L, about 60 L to about 14,000 L, about 60 L to about 12,000 L, about 60 L to about 10,000 L, about 60 L to about 9,500 L, about 60 L to about 9,000 L, about 60 L to about 8,500 L, about 60 L to about 8,000 L, about 60 L to about 7,500 L, about 60 L to about 7,000 L, about 60 L to about 6,500 L, about 60 L to about 6,000 L, about 60 L to about 5,500 L, about 60 L to about 5,000 L, about 60 L to about 4,500 L, about 60 L to about 4,000 L, about 60 L to about 3,500 L, about 60 L to about 3,000 L, about 60 L to about 2,500 L, about 60 L to about 2,000 L, about 60 L to about 1,500 L, about 60 L to about 1,000 L, about 60 L to about 900 L, about 60 L to about 800 L, about 60 L to about 700 L, about 60 L to about 600 L, about 60 L to about 500 L, about 60 L to about 400 L, about 60 L to about 300 L, about 60 L to about 250 L, about 60 L to about 200 L, about 60 L to about 150 L, about 60 L to about 100 L, about 60 L to about 80 L, about 80 L to about 20,000 L, about 80 L to about 18,000 L, about 80 L to about 16,000 L, about 80 L to about 14,000 L, about 80 L to about 12,000 L, about 80 L to about 10,000 L, about 80 L to about 9,500 L, about 80 L to about 9,000 L, about 80 L to about 8,500 L, about 80 L to about 8,000 L, about 80 L to about 7,500 L, about 80 L to about 7,000 L, about 80 L to about 6,500 L, about 80 L to about 6,000 L, about 80 L to about 5,500 L, about 80 L to about 5,000 L, about 80 L to about 4,500 L, about 80 L to about 4,000 L, about 80 L to about 3,500 L, about 80 L to about 3,000 L, about 80 L to about 2,500 L, about 80 L to about 2,000 L, about 80 L to about 1,500 L, about 80 L to about 1,000 L, about 80 L to about 900 L, about 80 L to about 800 L, about 80 L to about 700 L, about 80 L to about 600 L, about 80 L to about 500 L, about 80 L to about 400 L, about 80 L to about 300 L, about 80 L to about 250 L, about 80 L to about 200 L, about 80 L to about 150 L, about 80 L to about 100 L, about 100 L to about 20,000 L, about 100 L to about 18,000 L, about 100 L to about 16,000 L, about 100 L to about 14,000 L, about 100 L to about 12,000 L, about 100 L to about 10,000 L, about 100 L to about 9,500 L, about 100 L to about 9,000 L, about 100 L to about 8,500 L, about 100 L to about 8,000 L, about 100 L to about 7,500 L, about 100 L to about 7,000 L, about 100 L to about 6,500 L, about 100 L to about 6,000 L, about 100 L to about 5,500 L, about 100 L to about 5,000 L, about 100 L to about 4,500 L, about 100 L to about 4,000 L, about 100 L to about 3,500 L, about 100 L to about 3,000 L, about 100 L to about 2,500 L, about 100 L to about 2,000 L, about 100 L to about 1,500 L, about 100 L to about 1,000 L, about 100 L to about 900 L, about 100 L to about 800 L, about 100 L to about 700 L, about 100 L to about 600 L, about 100 L to about 500 L, about 100 L to about 400 L, about 100 L to about 300 L, about 100 L to about 250 L, about 100 L to about 200 L, about 100 L to about 150 L, about 150 L to about 20,000 L, about 150 L to about 18,000 L, about 150 L to about 16,000 L, about 150 L to about 14,000 L, about 150 L to about 12,000 L, about 150 L to about 10,000 L, about 150 L to about 9,500 L, about 150 L to about 9,000 L, about 150 L to about 8,500 L, about 150 L to about 8,000 L, about 150 L to about 7,500 L, about 150 L to about 7,000 L, about 150 L to about 6,500 L, about 150 L to about 6,000 L, about 150 L to about 5,500 L, about 150 L to about 5,000 L, about 150 L to about 4,500 L, about 150 L to about 4,000 L, about 150 L to about 3,500 L, about 150 L to about 3,000 L, about 150 L to about 2,500 L, about 150 L to about 2,000 L, about 150 L to about 1,500 L, about 150 L to about 1,000 L, about 150 L to about 900 L, about 150 L to about 800 L, about 150 L to about 700 L, about 150 L to about 600 L, about 150 L to about 500 L, about 150 L to about 400 L, about 150 L to about 300 L, about 150 L to about 250 L, about 150 L to about 200 L, about 200 L to about 20,000 L, about 200 L to about 18,000 L, about 200 L to about 16,000 L, about 200 L to about 14,000 L, about 200 L to about 12,000 L, about 200 L to about 10,000 L, about 200 L to about 9,500 L, about 200 L to about 9,000 L, about 200 L to about 8,500 L, about 200 L to about 8,000 L, about 200 L to about 7,500 L, about 200 L to about 7,000 L, about 200 L to about 6,500 L, about 200 L to about 6,000 L, about 200 L to about 5,500 L, about 200 L to about 5,000 L, about 200 L to about 4,500 L, about 200 L to about 4,000 L, about 200 L to about 3,500 L, about 200 L to about 3,000 L, about 200 L to about 2,500 L, about 200 L to about 2,000 L, about 200 L to about 1,500 L, about 200 L to about 1,000 L, about 200 L to about 900 L, about 200 L to about 800 L, about 200 L to about 700 L, about 200 L to about 600 L, about 200 L to about 500 L, about 200 L to about 400 L, about 200 L to about 300 L, about 200 L to about 250 L, about 250 L to about 20,000 L, about 250 L to about 18,000 L, about 250 L to about 16,000 L, about 250 L to about 14,000 L, about 250 L to about 12,000 L, about 250 L to about 10,000 L, about 250 L to about 9,500 L, about 250 L to about 9,000 L, about 250 L to about 8,500 L, about 250 L to about 8,000 L, about 250 L to about 7,500 L, about 250 L to about 7,000 L, about 250 L to about 6,500 L, about 250 L to about 6,000 L, about 250 L to about 5,500 L, about 250 L to about 5,000 L, about 250 L to about 4,500 L, about 250 L to about 4,000 L, about 250 L to about 3,500 L, about 250 L to about 3,000 L, about 250 L to about 2,500 L, about 250 L to about 2,000 L, about 250 L to about 1,500 L, about 250 L to about 1,000 L, about 250 L to about 900 L, about 250 L to about 800 L, about 250 L to about 700 L, about 250 L to about 600 L, about 250 L to about 500 L, about 250 L to about 400 L, about 250 L to about 300 L, about 300 L to about 20,000 L, about 300 L to about 18,000 L, about 300 L to about 16,000 L, about 300 L to about 14,000 L, about 300 L to about 12,000 L, about 300 L to about 10,000 L, about 300 L to about 9,500 L, about 300 L to about 9,000 L, about 300 L to about 8,500 L, about 300 L to about 8,000 L, about 300 L to about 7,500 L, about 300 L to about 7,000 L, about 300 L to about 6,500 L, about 300 L to about 6,000 L, about 300 L to about 5,500 L, about 300 L to about 5,000 L, about 300 L to about 4,500 L, about 300 L to about 4,000 L, about 300 L to about 3,500 L, about 300 L to about 3,000 L, about 300 L to about 2,500 L, about 300 L to about 2,000 L, about 300 L to about 1,500 L, about 300 L to about 1,000 L, about 300 L to about 900 L, about 300 L to about 800 L, about 300 L to about 700 L, about 300 L to about 600 L, about 300 L to about 500 L, about 300 L to about 400 L, about 400 L to about 20,000 L, about 400 L to about 18,000 L, about 400 L to about 16,000 L, about 400 L to about 14,000 L, about 400 L to about 12,000 L, about 400 L to about 10,000 L, about 400 L to about 9,500 L, about 400 L to about 9,000 L, about 400 L to about 8,500 L, about 400 L to about 8,000 L, about 400 L to about 7,500 L, about 400 L to about 7,000 L, about 400 L to about 6,500 L, about 400 L to about 6,000 L, about 400 L to about 5,500 L, about 400 L to about 5,000 L, about 400 L to about 4,500 L, about 400 L to about 4,000 L, about 400 L to about 3,500 L, about 400 L to about 3,000 L, about 400 L to about 2,500 L, about 400 L to about 2,000 L, about 400 L to about 1,500 L, about 400 L to about 1,000 L, about 400 L to about 900 L, about 400 L to about 800 L, about 400 L to about 700 L, about 400 L to about 600 L, about 400 L to about 500 L, about 500 L to about 20,000 L, about 500 L to about 18,000 L, about 500 L to about 16,000 L, about 500 L to about 14,000 L, about 500 L to about 12,000 L, about 500 L to about 10,000 L, about 500 L to about 9,500 L, about 500 L to about 9,000 L, about 500 L to about 8,500 L, about 500 L to about 8,000 L, about 500 L to about 7,500 L, about 500 L to about 7,000 L, about 500 L to about 6,500 L, about 500 L to about 6,000 L, about 500 L to about 5,500 L, about 500 L to about 5,000 L, about 500 L to about 4,500 L, about 500 L to about 4,000 L, about 500 L to about 3,500 L, about 500 L to about 3,000 L, about 500 L to about 2,500 L, about 500 L to about 2,000 L, about 500 L to about 1,500 L, about 500 L to about 1,000 L, about 500 L to about 900 L, about 500 L to about 800 L, about 500 L to about 700 L, about 500 L to about 600 L, about 600 L to about 20,000 L, about 600 L to about 18,000 L, about 600 L to about 16,000 L, about 600 L to about 14,000 L, about 600 L to about 12,000 L, about 600 L to about 10,000 L, about 600 L to about 9,500 L, about 600 L to about 9,000 L, about 600 L to about 8,500 L, about 600 L to about 8,000 L, about 600 L to about 7,500 L, about 600 L to about 7,000 L, about 600 L to about 6,500 L, about 600 L to about 6,000 L, about 600 L to about 5,500 L, about 600 L to about 5,000 L, about 600 L to about 4,500 L, about 600 L to about 4,000 L, about 600 L to about 3,500 L, about 600 L to about 3,000 L, about 600 L to about 2,500 L, about 600 L to about 2,000 L, about 600 L to about 1,500 L, about 600 L to about 1,000 L, about 600 L to about 900 L, about 600 L to about 800 L, about 600 L to about 700 L, about 700 L to about 20,000 L, about 700 L to about 18,000 L, about 700 L to about 16,000 L, about 700 L to about 14,000 L, about 700 L to about 12,000 L, about 700 L to about 10,000 L, about 700 L to about 9,500 L, about 700 L to about 9,000 L, about 700 L to about 8,500 L, about 700 L to about 8,000 L, about 700 L to about 7,500 L, about 700 L to about 7,000 L, about 700 L to about 6,500 L, about 700 L to about 6,000 L, about 700 L to about 5,500 L, about 700 L to about 5,000 L, about 700 L to about 4,500 L, about 700 L to about 4,000 L, about 700 L to about 3,500 L, about 700 L to about 3,000 L, about 700 L to about 2,500 L, about 700 L to about 2,000 L, about 700 L to about 1,500 L, about 700 L to about 1,000 L, about 700 L to about 900 L, about 700 L to about 800 L, about 800 L to about 20,000 L, about 800 L to about 18,000 L, about 800 L to about 16,000 L, about 800 L to about 14,000 L, about 800 L to about 12,000 L, about 800 L to about 10,000 L, about 800 L to about 9,500 L, about 800 L to about 9,000 L, about 800 L to about 8,500 L, about 800 L to about 8,000 L, about 800 L to about 7,500 L, about 800 L to about 7,000 L, about 800 L to about 6,500 L, about 800 L to about 6,000 L, about 800 L to about 5,500 L, about 800 L to about 5,000 L, about 800 L to about 4,500 L, about 800 L to about 4,000 L, about 800 L to about 3,500 L, about 800 L to about 3,000 L, about 800 L to about 2,500 L, about 800 L to about 2,000 L, about 800 L to about 1,500 L, about 800 L to about 1,000 L, about 800 L to about 900 L, about 900 L to about 20,000 L, about 900 L to about 18,000 L, about 900 L to about 16,000 L, about 900 L to about 14,000 L, about 900 L to about 12,000 L, about 900 L to about 10,000 L, about 900 L to about 9,500 L, about 900 L to about 9,000 L, about 900 L to about 8,500 L, about 900 L to about 8,000 L, about 900 L to about 7,500 L, about 900 L to about 7,000 L, about 900 L to about 6,500 L, about 900 L to about 6,000 L, about 900 L to about 5,500 L, about 900 L to about 5,000 L, about 900 L to about 4,500 L, about 900 L to about 4,000 L, about 900 L to about 3,500 L, about 900 L to about 3,000 L, about 900 L to about 2,500 L, about 900 L to about 2,000 L, about 900 L to about 1,500 L, about 900 L to about 1,000 L, about 1,000 L to about 20,000 L, about 1,000 L to about 18,000 L, about 1,000 L to about 16,000 L, about 1,000 L to about 14,000 L, about 1,000 L to about 12,000 L, about 1,000 L to about 10,000 L, about 1,000 L to about 9,500 L, about 1,000 L to about 9,000 L, about 1,000 L to about 8,500 L, about 1,000 L to about 8,000 L, about 1,000 L to about 7,500 L, about 1,000 L to about 7,000 L, about 1,000 L to about 6,500 L, about 1,000 L to about 6,000 L, about 1,000 L to about 5,500 L, about 1,000 L to about 5,000 L, about 1,000 L to about 4,500 L, about 1,000 L to about 4,000 L, about 1,000 L to about 3,500 L, about 1,000 L to about 3,000 L, about 1,000 L to about 2,500 L, about 1,000 L to about 2,000 L, about 1,000 L to about 1,500 L, about 1,500 L to about 20,000 L, about 1,500 L to about 18,000 L, about 1,500 L to about 16,000 L, about 1,500 L to about 14,000 L, about 1,500 L to about 12,000 L, about 1,500 L to about 10,000 L, about 1,500 L to about 9,500 L, about 1,500 L to about 9,000 L, about 1,500 L to about 8,500 L, about 1,500 L to about 8,000 L, about 1,500 L to about 7,500 L, about 1,500 L to about 7,000 L, about 1,500 L to about 6,500 L, about 1,500 L to about 6,000 L, about 1,500 L to about 5,500 L, about 1,500 L to about 5,000 L, about 1,500 L to about 4,500 L, about 1,500 L to about 4,000 L, about 1,500 L to about 3,500 L, about 1,500 L to about 3,000 L, about 1,500 L to about 2,500 L, about 1,500 L to about 2,000 L, about 2,000 L to about 20,000 L, about 2,000 L to about 18,000 L, about 2,000 L to about 16,000 L, about 2,000 L to about 14,000 L, about 2,000 L to about 12,000 L, about 2,000 L to about 10,000 L, about 2,000 L to about 9,500 L, about 2,000 L to about 9,000 L, about 2,000 L to about 8,500 L, about 2,000 L to about 8,000 L, about 2,000 L to about 7,500 L, about 2,000 L to about 7,000 L, about 2,000 L to about 6,500 L, about 2,000 L to about 6,000 L, about 2,000 L to about 5,500 L, about 2,000 L to about 5,000 L, about 2,000 L to about 4,500 L, about 2,000 L to about 4,000 L, about 2,000 L to about 3,500 L, about 2,000 L to about 3,000 L, about 2,000 L to about 2,500 L, about 2,500 L to about 20,000 L, about 2,500 L to about 18,000 L, about 2,500 L to about 16,000 L, about 2,500 L to about 14,000 L, about 2,500 L to about 12,000 L, about 2,500 L to about 10,000 L, about 2,500 L to about 9,500 L, about 2,500 L to about 9,000 L, about 2,500 L to about 8,500 L, about 2,500 L to about 8,000 L, about 2,500 L to about 7,500 L, about 2,500 L to about 7,000 L, about 2,500 L to about 6,500 L, about 2,500 L to about 6,000 L, about 2,500 L to about 5,500 L, about 2,500 L to about 5,000 L, about 2,500 L to about 4,500 L, about 2,500 L to about 4,000 L, about 2,500 L to about 3,500 L, about 2,500 L to about 3,000 L, about 3,000 L to about 20,000 L, about 3,000 L to about 18,000 L, about 3,000 L to about 16,000 L, about 3,000 L to about 14,000 L, about 3,000 L to about 12,000 L, about 3,000 L to about 10,000 L, about 3,000 L to about 9,500 L, about 3,000 L to about 9,000 L, about 3,000 L to about 8,500 L, about 3,000 L to about 8,000 L, about 3,000 L to about 7,500 L, about 3,000 L to about 7,000 L, about 3,000 L to about 6,500 L, about 3,000 L to about 6,000 L, about 3,000 L to about 5,500 L, about 3,000 L to about 5,000 L, about 3,000 L to about 4,500 L, about 3,000 L to about 4,000 L, about 3,000 L to about 3,500 L, about 3,500 L to about 20,000 L, about 3,500 L to about 18,000 L, about 3,500 L to about 16,000 L, about 3,500 L to about 14,000 L, about 3,500 L to about 12,000 L, about 3,500 L to about 10,000 L, about 3,500 L to about 9,500 L, about 3,500 L to about 9,000 L, about 3,500 L to about 8,500 L, about 3,500 L to about 8,000 L, about 3,500 L to about 7,500 L, about 3,500 L to about 7,000 L, about 3,500 L to about 6,500 L, about 3,500 L to about 6,000 L, about 3,500 L to about 5,500 L, about 3,500 L to about 5,000 L, about 3,500 L to about 4,500 L, about 3,500 L to about 4,000 L, about 4,000 L to about 20,000 L, about 4,000 L to about 18,000 L, about 4,000 L to about 16,000 L, about 4,000 L to about 14,000 L, about 4,000 L to about 12,000 L, about 4,000 L to about 10,000 L, about 4,000 L to about 9,500 L, about 4,000 L to about 9,000 L, about 4,000 L to about 8,500 L, about 4,000 L to about 8,000 L, about 4,000 L to about 7,500 L, about 4,000 L to about 7,000 L, about 4,000 L to about 6,500 L, about 4,000 L to about 6,000 L, about 4,000

L to about 5,500 L, about 4,000 L to about 5,000 L, about 4,000 L to about 4,500 L, about 4,500 L to about 20,000 L, about 4,500 L to about 18,000 L, about 4,500 L to about 16,000 L, about 4,500 L to about 14,000 L, about 4,500 L to about 12,000 L, about 4,500 L to about 10,000 L, about 4,500 L to about 9,500 L, about 4,500 L to about 9,000 L, about 4,500 L to about 8,500 L, about 4,500 L to about 8,000 L, about 4,500 L to about 7,500 L, about 4,500 L to about 7,000 L, about 4,500 L to about 6,500 L, about 4,500 L to about 6,000 L, about 4,500 L to about 5,500 L, about 4,500 L to about 5,000 L, about 5,000 L to about 20,000 L, about 5,000 L to about 18,000 L, about 5,000 L to about 16,000 L, about 5,000 L to about 14,000 L, about 5,000 L to about 12,000 L, about 5,000 L to about 10,000 L, about 5,000 L to about 9,500 L, about 5,000 L to about 9,000 L, about 5,000 L to about 8,500 L, about 5,000 L to about 8,000 L, about 5,000 L to about 7,500 L, about 5,000 L to about 7,000 L, about 5,000 L to about 6,500 L, about 5,000 L to about 6,000 L, about 5,000 L to about 5,500 L, about 5,500 L to about 20,000 L, about 5,500 L to about 18,000 L, about 5,500 L to about 16,000 L, about 5,500 L to about 14,000 L, about 5,500 L to about 12,000 L, about 5,500 L to about 10,000 L, about 5,500 L to about 9,500 L, about 5,500 L to about 9,000 L, about 5,500 L to about 8,500 L, about 5,500 L to about 8,000 L, about 5,500 L to about 7,500 L, about 5,500 L to about 7,000 L, about 5,500 L to about 6,500 L, about 5,500 L to about 6,000 L, about 6,000 L to about 20,000 L, about 6,000 L to about 18,000 L, about 6,000 L to about 16,000 L, about 6,000 L to about 14,000 L, about 6,000 L to about 12,000 L, about 6,000 L to about 10,000 L, about 6,000 L to about 9,500 L, about 6,000 L to about 9,000 L, about 6,000 L to about 8,500 L, about 6,000 L to about 8,000 L, about 6,000 L to about 7,500 L, about 6,000 L to about 7,000 L, about 6,000 L to about 6,500 L, about 6,500 L to about 20,000 L, about 6,500 L to about 18,000 L, about 6,500 L to about 16,000 L, about 6,500 L to about 14,000 L, about 6,500 L to about 12,000 L, about 6,500 L to about 10,000 L, about 6,500 L to about 9,500 L, about 6,500 L to about 9,000 L, about 6,500 L to about 8,500 L, about 6,500 L to about 8,000 L, about 6,500 L to about 7,500 L, about 6,500 L to about 7,000 L, about 7,000 L to about 20,000 L, about 7,000 L to about 18,000 L, about 7,000 L to about 16,000 L, about 7,000 L to about 14,000 L, about 7,000 L to about 12,000 L, about 7,000 L to about 10,000 L, about 7,000 L to about 9,500 L, about 7,000 L to about 9,000 L, about 7,000 L to about 8,500 L, about 7,000 L to about 8,000 L, about 7,000 L to about 7,500 L, about 7,500 L to about 20,000 L, about 7,500 L to about 18,000 L, about 7,500 L to about 16,000 L, about 7,500 L to about 14,000 L, about 7,500 L to about 12,000 L, about 7,500 L to about 10,000 L, about 7,500 L to about 9,500 L, about 7,500 L to about 9,000 L, about 7,500 L to about 8,500 L, about 7,500 L to about 8,000 L, about 8,000 L to about 20,000 L, about 8,000 L to about 18,000 L, about 8,000 L to about 16,000 L, about 8,000 L to about 14,000 L, about 8,000 L to about 12,000 L, about 8,000 L to about 10,000 L, about 8,000 L to about 9,500 L, about 8,000 L to about 9,000 L, about 8,000 L to about 8,500 L, about 8,500 L to about 20,000 L, about 8,500 L to about 18,000 L, about 8,500 L to about 16,000 L, about 8,500 L to about 14,000 L, about 8,500 L to about 12,000 L, about 8,500 L to about 10,000 L, about 8,500 L to about 9,500 L, about 8,500 L to about 9,000 L, about 9,000 L to about 20,000 L, about 9,000 L to about 18,000 L, about 9,000 L to about 16,000 L, about 9,000 L to about 14,000 L, about 9,000 L to about 12,000 L, about 9,000 L to about 10,000 L, about 9,000 L to about 9,500 L, about 9,500 L to about 20,000 L, about 9,500 L to about 18,000 L, about 9,500 L to about 16,000 L, about 9,500 L to about 14,000 L, about 9,500 L to about 12,000 L, about 9,500 L to about 10,000 L, about 10,000 L to about 20,000 L, about 10,000 L to about 18,000 L, about 10,000 L to about 16,000 L, about 10,000 L to about 14,000 L, about 10,000 L to about 12,000 L, about 12,000 L to about 20,000 L, about 12,000 L to about 18,000 L, about 12,000 L to about 16,000 L, about 12,000 L to about 14,000 L, about 14,000 L to about 20,000 L, about 14,000 L to about 18,000 L, about 14,000 L to about 16,000 L, about 16,000 L to about 20,000 L, about 16,000 L to about 18,000 L, or about 18,000 L to about 20,000 L.

Figure 3:
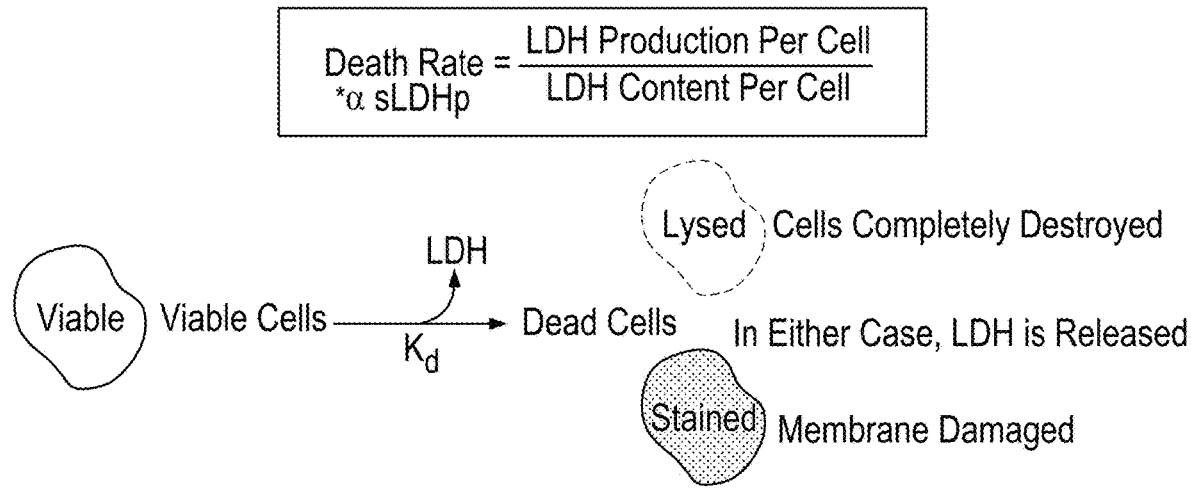
FIG. 3 is a diagram showing the relationship between specific lactate dehydrogenase (LDH) production and cell death rate.

In some embodiments, the operation parameters can be any parameter that are related to cell viability or cell death (e.g., shear stress, concentration of a sensitizer, concentration of a protectant, temperature, pH, nutrient composition, biomass loading and feeding strategy). The cell viability or cell death rate can be measured by using cells that can express lactate dehydrogenase (LDH). When the cell that can express LDH dies, LDH in the cell is released into the liquid culture medium. Thus, the cell viability or the cell death rate can be measured orthogonally with LDH, and is proportional to specific LDH production (sLDHp) (FIG. 3).

Figure 4:
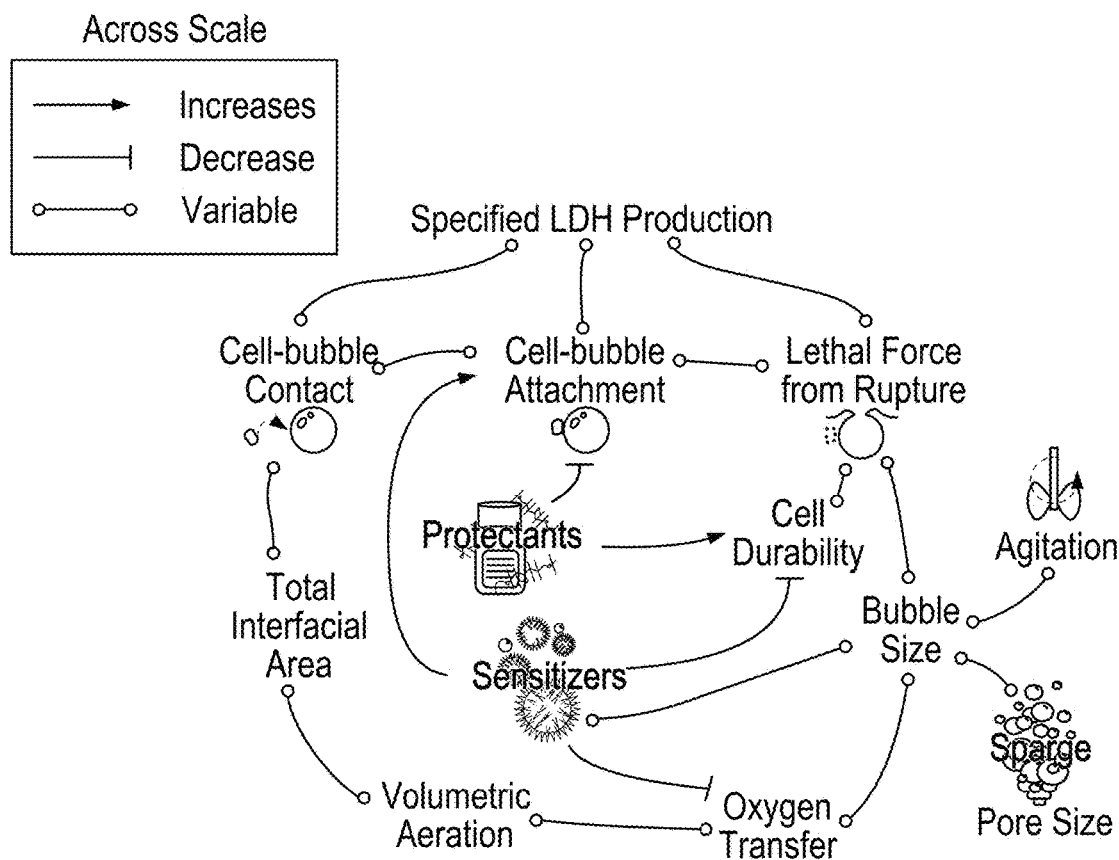
FIG. 4 is a diagram showing the relationship between protectants, sensitizers, and rotary agitation, and the impact of protectants, sensitizers, and agitation on specific LDH production in a cell culture.

FIG. 4 shows how Pluronic® (e.g., protectants), sensitizer, and shear (e.g., agitation) can affect specific LDH production. As shown in FIG. 4, protectants can decrease cell-bubble attachment and increase cell durability, thus maintaining high cell viability and protecting cells from death. In contrast, sensitizers can increase cell-bubble attachments and decrease cell durability, thus decreasing cell viability. As these parameters are interconnected with each other, it is often very difficult to predict the exact effects of sensitizers, agitation, and/or protectants by traditional models.

Figure 5:
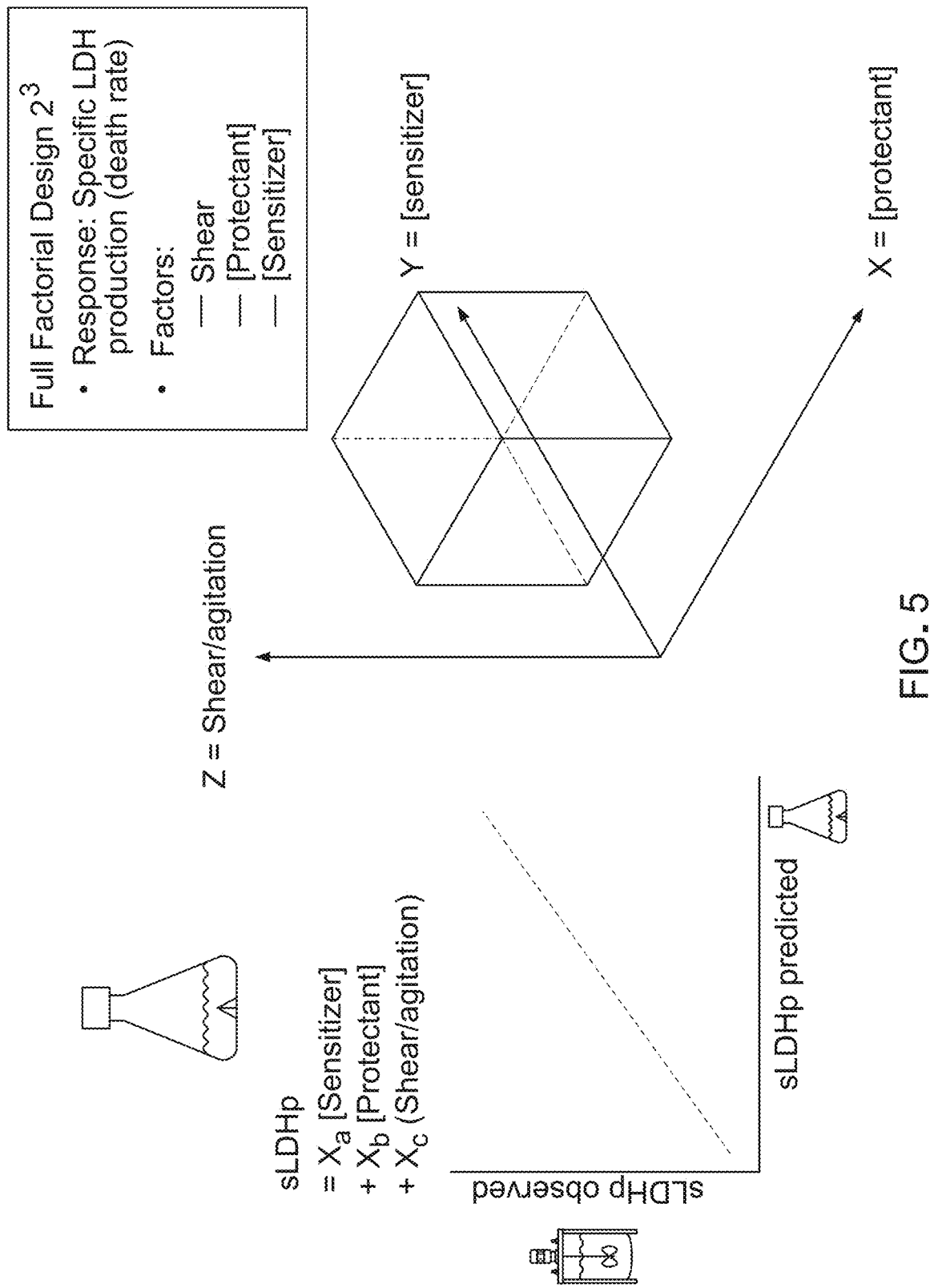
FIG. 5 is a diagram showing that the specific LDH production is a consequence of sensitizer concentration, protectant concentration, and rotary agitation (shear stress).

FIG. 5 shows that the specific LDH production in the small scale model is a function of sensitizer concentration, protectant concentration, and agitation. Because of the interaction among there parameters, the specific LDH production usually does not have a linear relationship with any of these parameters. The effects of these parameters on the specific LDH production can be determined by factorial design, e.g., full factorial design, or fractional factorial design.

Figure 6:
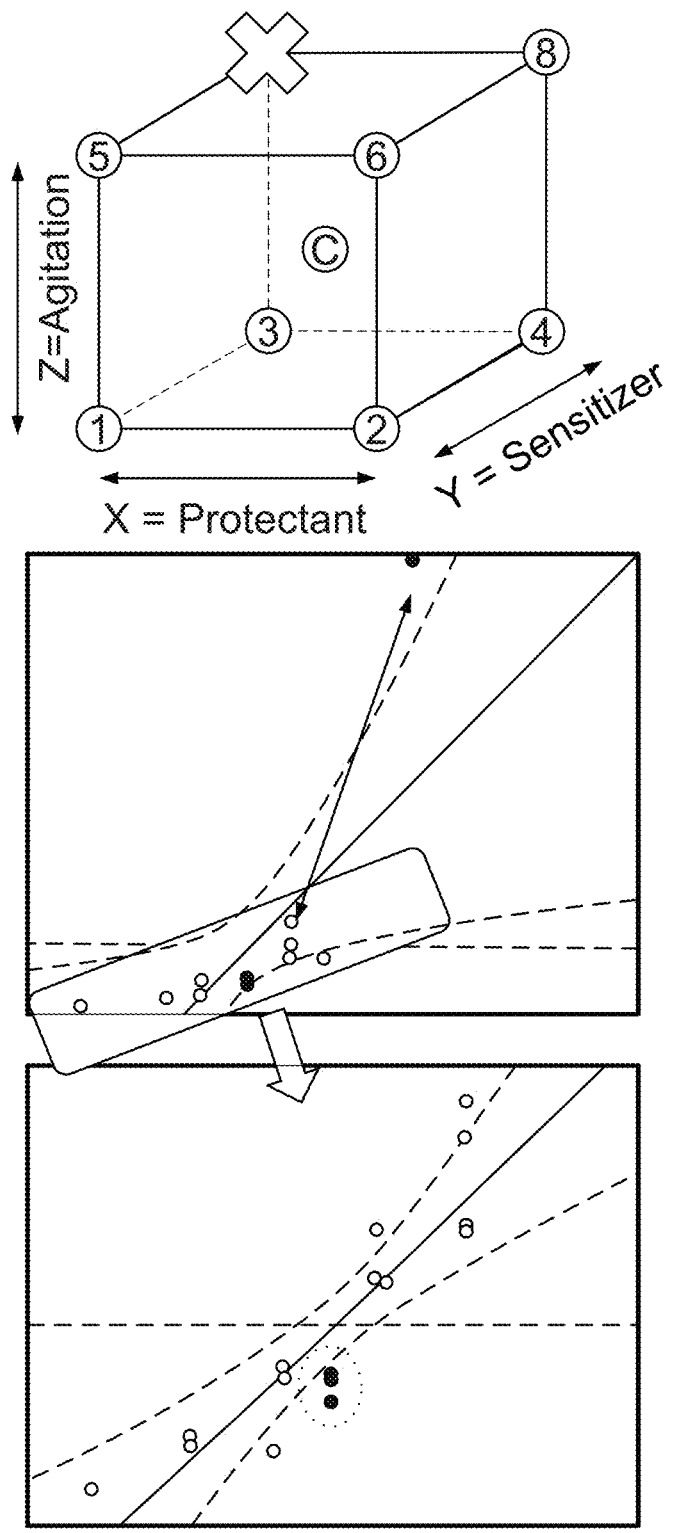
FIG. 6 shows full factorial design for the three selected parameters: sensitizer concentration, protectant concentration, and rotary agitation (shear stress). The top panel shows the full factorial design ($2^3$), where the response is specific LDH production (death rate) and the factors are shear, concentration of protectant, and concentration of sensitizer. The middle panel shows that failure resulted in an extreme value, there is a large range between point of failure versus the rest of the data, the point of failure is difficult to model, and the extreme value is excluded (inoperable region). The bottom panel shows that centerpoints are poorly predicted (indication of curvature, response is likely non-linear, and increasing RPM doesn't scale linearly).

Factorial design involves performing experiments under a set of conditions, and the conditions are defined by a set of parameters (e.g., operation parameters). In the set of conditions, each parameter can have two or more levels. The purpose of factorial design is to study the main effects and the interaction effects among different parameters (e.g., sensitizer concentration, protectant concentration, and agitation). The term "full factorial design" refers to an experiment design that includes all possible combinations of different levels across all parameters. For example, with three parameters (i.e., factors) each taking two levels, a full factorial design will have 8 combinations in total, and is usually called a $2^3$ factorial design (FIG. 6). In contrast, the term "fractional factorial designs" refers to experimental designs consisting of a carefully chosen subset (fraction) of the experimental runs of a full factorial design. The subset is chosen so as to exploit the sparsity-of-effects principle to expose information about the most important features of the problem studied, while using a fraction of the effort of a full factorial design in terms of experimental runs and resources. By performing factorial design, the inoperable region (e.g., the combination of values of parameters that make the operation fail) can be identified. The factorial design is known in the art, and is described, e.g., in Box, G. E.; Hunter, W. G.; Hunter, J. S. (2005). Statistics for Experimenters: Design, Innovation, and Discovery (2nd ed.).

Wiley. ISBN 0-471-71813-0; Vicente, Gemma, et al. "Application of the factorial design of experiments and response surface methodology to optimize biodiesel production." Industrial crops and products 8.1 (1998): 29-35; Vandervoort, Jo, and Annick Ludwig. "Biocompatible stabilizers in the preparation of PLGA nanoparticles: a factorial design study." International journal of pharmaceutics 238.1-2 (2002): 77-92; each of which is incorporated by reference herein in its entirety.

Figure 7:
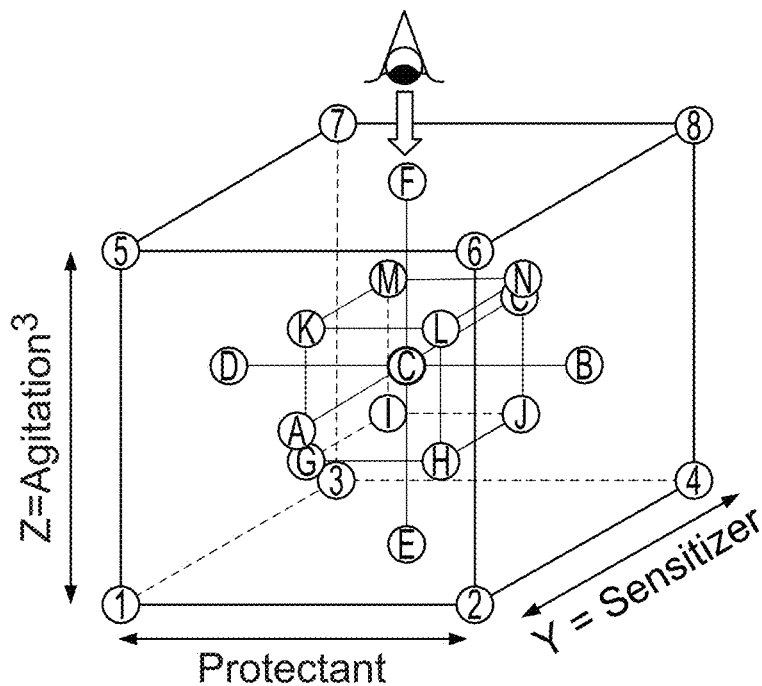
FIG. 7 is a diagram showing full factorial design combined with inscribed center composite design for the selected parameters of sensitizer concentration, protectant concentration, and rotary agitation (shear stress).

In a typical factorial design, the center points (e.g., regions of interest) are often poorly predicted. Thus, in some embodiments, the factorial design can be used in combination with center composite design (e.g., inscribed center composite design, circumscribed center composite design, or face centered composite design) (FIG. 7). A center composite design is an experimental design that contains an imbedded factorial or fractional factorial design with center points that is augmented with a group of axial points that allow estimation of curvature. The composite design is known in the art, and a detailed description regarding center composite design can be found, e.g., in Box, G. E.; Hunter, W. G.; Hunter, J. S. (2005). Statistics for Experimenters: Design, Innovation, and Discovery (2nd ed.). Wiley. ISBN 0-471-71813-0; Ahmadi, M., et al. "Application of the central composite design and response surface methodology to the advanced treatment of olive oil processing wastewater using Fenton's peroxidation." Journal of Hazardous Materials 123.1-3 (2005): 187-195; each of which is incorporated herein by reference in its entirety.

Figure 8:
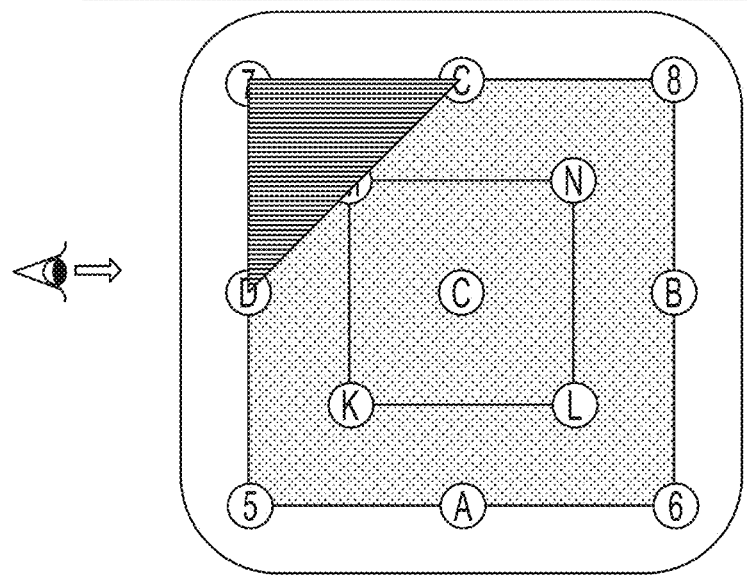
FIG. 8 is a diagram showing the advantages of the full factorial design combined with inscribed center composite design.
Figure 9:
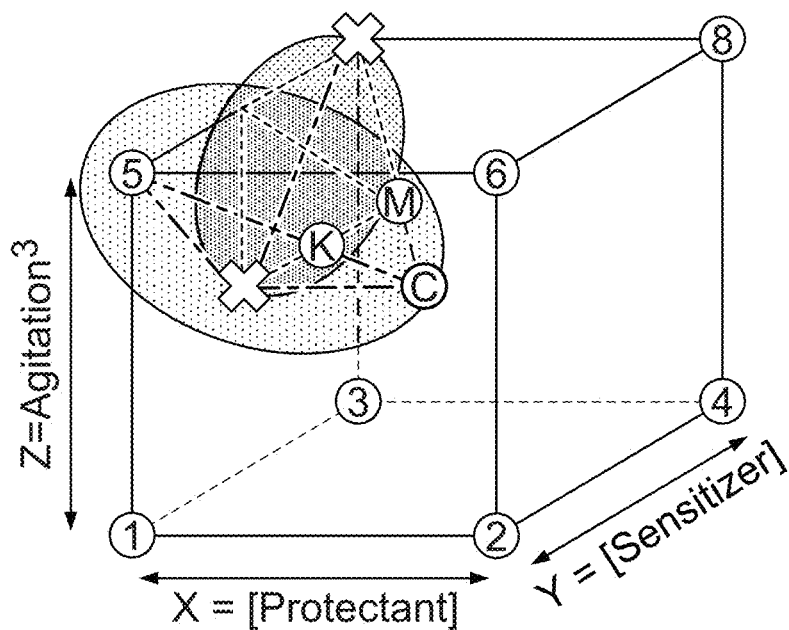
FIG. 9 is a diagram illustrating that the methods described herein can be used to identify region of poor performance (light shading) and region of operation failure (dark shading).
Figure 9:
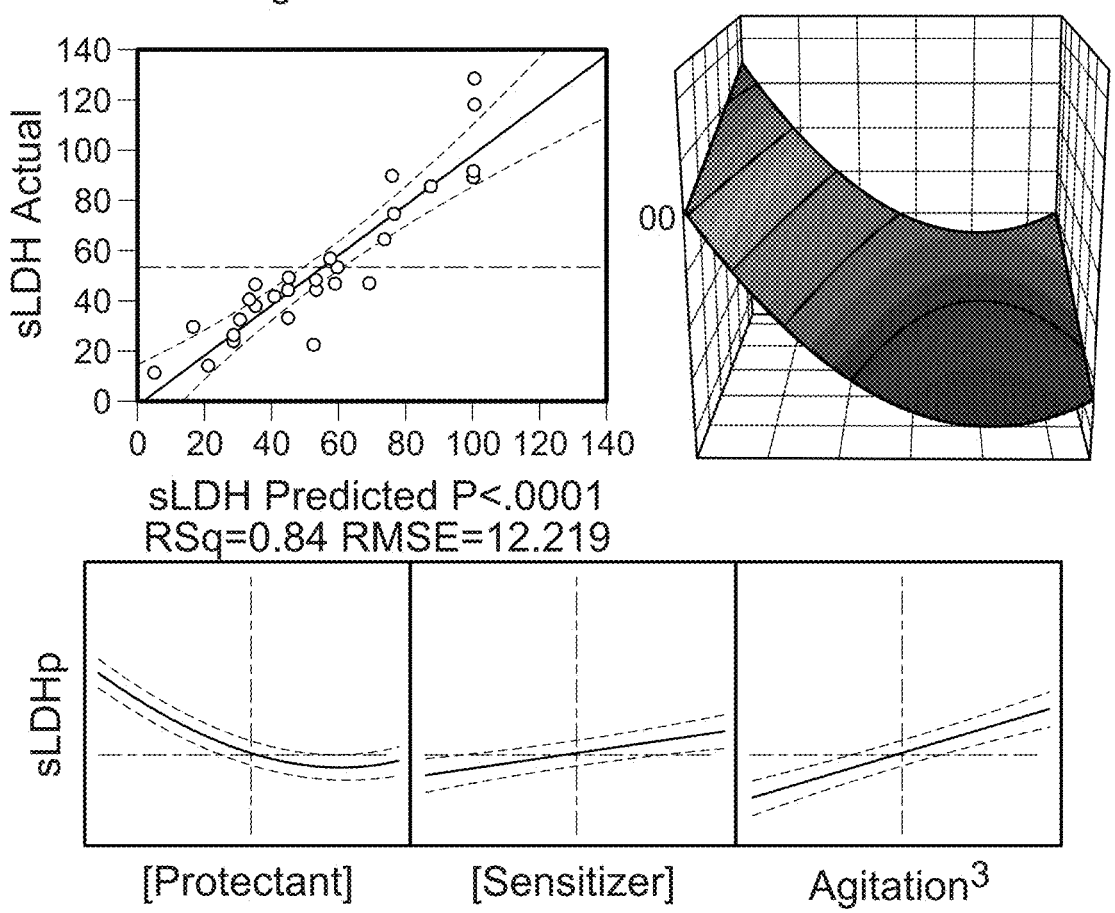

In some embodiments, the testing conditions are selected based on full factorial screening and center composite design (e.g., inscribed center composite design). By combining the full factorial screening and center composite design, the selected testing conditions can maximize regions of interest and minimize regions of potential failure (FIG. 8 and FIG. 9).

The experiment results of these test conditions in test culture vessels provide an estimated contour that illustrates the relationship among the selected parameters. Once the contour of the small scale model has been determined, the small scale model can be used to predict the missing values. For example, with the knowledge of antifoam concentration or shear stress, it can predict how much Pluronic® is required for operations. This relationship is determined by correlating cell growth rate and death rates across different scales (e.g., small scale, benchtop, production, etc.).

Figure 10:
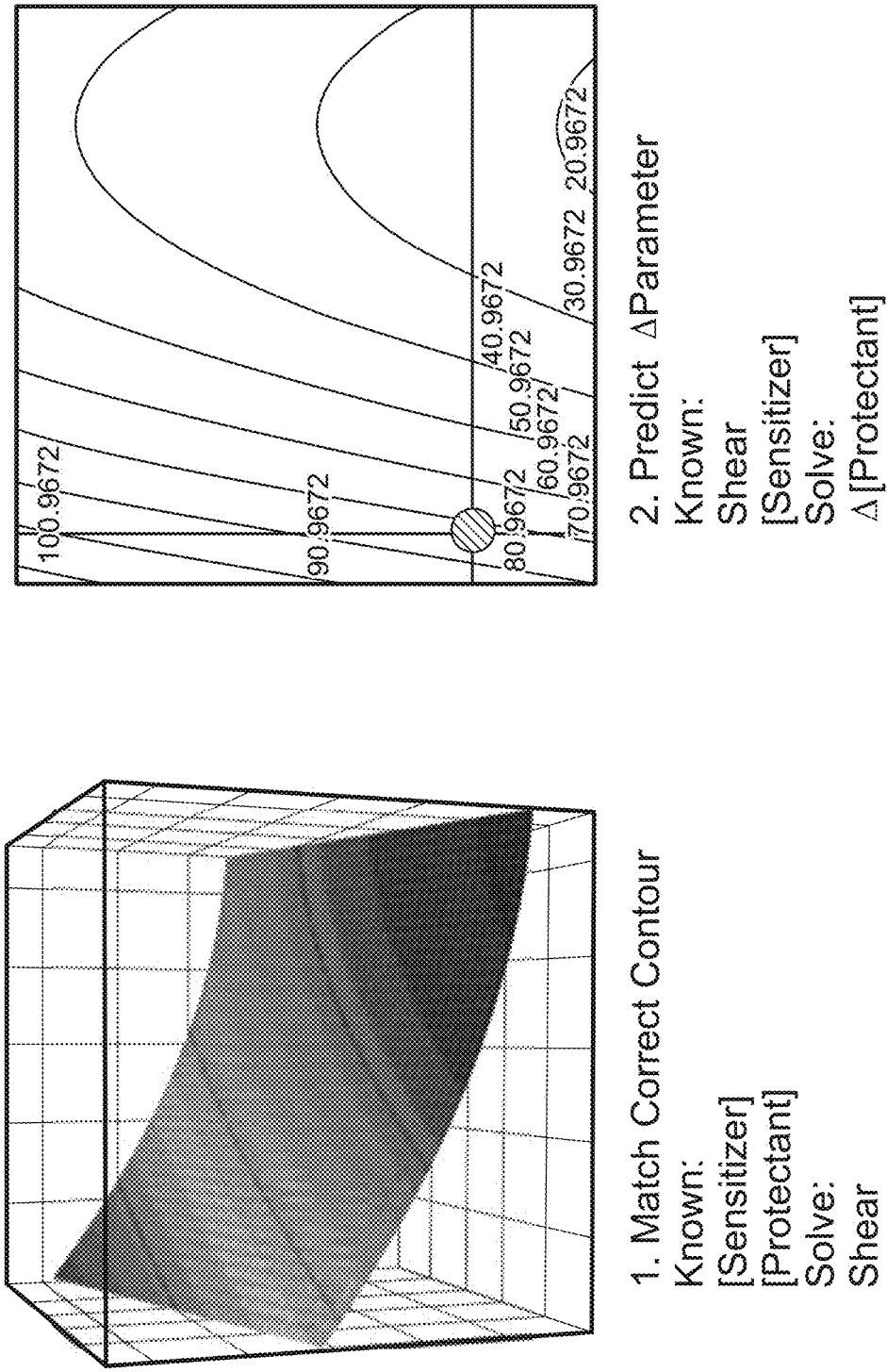
FIG. 10 is a diagram illustrating methods of normalizing shear stress across scale via specific LDH production and methods of predicting effects of parameter changes (Δparameter).
Figure 11:
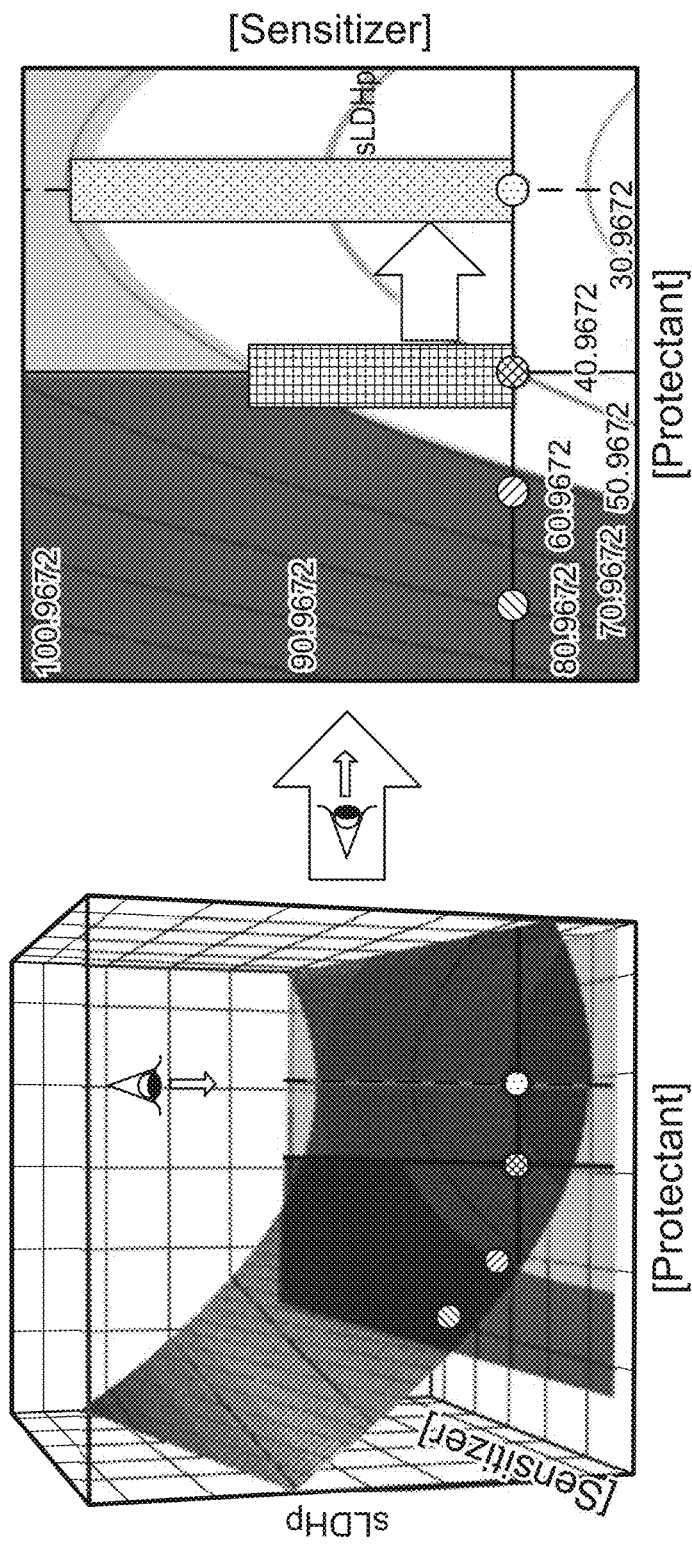
FIG. 11 is a diagram illustrating how the models described herein can be used to optimize operating conditions of a production bioreactor. The data show that the operating condition (rectangle with filled with open squares) currently works, but can be further optimized (light shaded rectangle to the right of the large arrow) (e.g., increase concentration range of sensitizer tolerance in process and improve resilience to vessel foam out).
Figure 12:
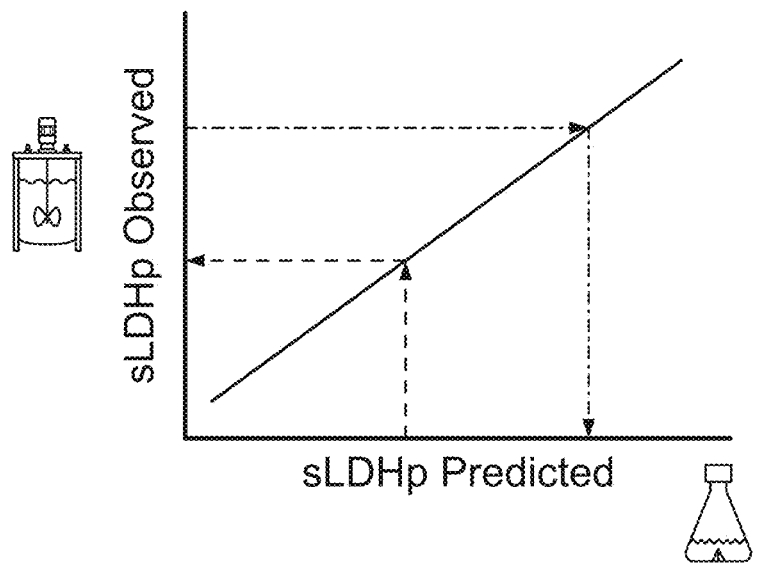
FIG. 12 lists the capabilities and utilities of the models described herein. The model is able to align different scales, predict changes in parameters, and optimize existing design spaces. The model also provides for an increase in the predictability/alignment of performance across scales (e.g., create more representative small scale models and augment understanding of shear across scale on top of traditional methodologies). The model also provide for increased process robustness (e.g., improved shear tolerance for process intensification and improved guidance on concentration of sensitizer and concentration of protectant addition across different shear profiles).

In some embodiments, the estimated contour of the small scale model can be used to match the data points collected at a different scale (e.g., the production scale). Because the concentration of sensitizer and protectants are known, it is possible to determine the shear stress in the small scale model that corresponds to the shear stress in the production bioreactor from the contour (FIG. 10). Based on shear stress that corresponds to the shear stress in the production bioreactor and the concentration of sensitizer, the effect of protectant concentration change (A[Protectant]) can be determined from the estimated contour (FIG. 11). For example, as shown in FIG. 11, the far left point (circle), the left center point (circle), the right center point (circle), and the far right point (circle) all have the same shear stress and sensitizer concentration. The shaded region is inoperable space. By increasing the protectant concentration (from the right center point (circle) to the far right point (circle), with an arrow depicted between these two points), the acceptable range of sensitizer concentration can be increased, leading to better resilience to sensitizer.

Thus, in some embodiments, the model as described herein can be used to determine interactive effects among different parameters. The traditional models usually study the effect of each parameter individually. The models as described herein can study the effects of three parameters at once rather than the effect of each parameter individually. Thus, this model described herein can predict where the expected cell culture performance will be if any single parameter is changed.

Furthermore, those traditional scale-up parameters usually do not provide cell culture performance predictions. The model described herein can predict an operating range with better guidance which leads to a lower chance of failure when moving to a production scale, and it provides the ability to scale up once other traditional parameters have been met (P/V, tip speed, mixing time, KLa).

In some other embodiments, the models as described herein can be used to establish an operating design space for reactors at any scale given any individual parameter or combination of parameters (e.g., Pluronic®, antifoam, and shear). The model can be used to determine maximum amount of antifoam agents that the cell culture can tolerate before failure for a given shear condition.

In some embodiments, the model can be used to determine maximum amount of antifoam agents that the Pluronic® concentration can sustain before losing its efficacy for a given shear condition.

In some embodiments, the model can be used to test different types of antifoam agents (antifoam C, autoclaved antifoam, irradiated antifoams, etc.) against different Pluronic®.

In some embodiments, the model can be cell-density-range independent, and need not apply only to intensified perfusion cultures, as it uses LDH to normalize across scales.

In some embodiments, the model can also test antifoam concentrations either with absolute addition (1 time bolus at beginning) or daily addition.

In some embodiments, the model can be used to test for the kinetics behind antifoam deactivation and its impact to cell culture.

Cells

The methods provided herein can be used to culture a variety of different cells (e.g., mammalian cells, bacterial cells, and yeast cells).

Non-limiting examples of bacterial cells include *E. coli*, *Clostridium difficile*, *Clostridium sporogenes*, *Clostridium beijerinkii*, and *Clostridium acetobutylicum*. Exemplary commercially available bacterial cells that can be used in any of the methods described herein include BL21(DE3) (Novagen), BL21(DE3)-pLysS (Novagen), BL21 Star-pLysS (Invitrogen), BL21-SI (Invitrogen), BL21-AI (Invitrogen), Tuner (Novagen), Tuner pLysS (Novagen), Origami (Novagen), Origami D (Novagen), Origami B pLysS (Novagen), Rosetta (Novagen), Rosetta pLysS (Novagen), Rosetta-gami-pLysS (Novagen), BL21 CodonPlus (Stratagene), AD494 (Novagen), BL21trxB (Novagen), HMS174 (Novagen), NovaBlue (DE3) (Novagen), BLR (Novagen), C41(DE3) (Lucigen), C43(DE3) (Lucigen), Lemo21(DE3) (New England BioLabs), SHuffle T7 (New England BioLabs), ArticExpress (Agilent Technologies), and Artic Express (DE3) (Agilent Technologies).

Non-limiting examples of yeast cells include: *S. cerevisiae*, *S. exiguus*, and *Pichia pastoris*. Additional examples of yeast cells that can be used in any of the methods described herein include those from the genera *Saccharomyces*, *Pichia*, *Kluyveromyces*, *Hansenula*, and *Yarrowia*. Additional examples of yeast cells that can be used in any of the methods described herein are described in Nielsen, *Methods in Enzymology* 536:133-147, 2014.

Non-limiting examples of mammalian cells that can be cultured using any of the methods described herein include: Chinese hamster ovary (CHO) cells (e.g., CHO DG44 cells, CHO-K1s cells, and CHO-DXB11 cells), Sp2.0, myeloma cells (e.g., NS/0), B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. Additional mammalian cells that can be cultured using the methods described herein are known in the art. In non-limiting examples of any of the methods described herein, the concentration of mammalian cells present in a test culture vessel and/or a production bioreactor at the start of culturing is about $0.1 \times 10^6$ cells/mL to about $10 \times 10^6$ cells/mL (e.g., about $0.1 \times 10^6$ cells/mL to about $9 \times 10^6$ cells/mL, about $0.1 \times 10^6$ cells/mL to about $8 \times 10^6$ cells/mL, about $0.1 \times 10^6$ cells/mL to about $7 \times 10^6$ cells/mL, about $0.1 \times 10^6$ cells/mL to about $6 \times 10^6$ cells/mL, about $0.1 \times 10^6$ cells/mL to about $5 \times 10^6$ cells/mL, about $0.1 \times 10^6$ cells/mL to about $4 \times 10^6$ cells/mL, about $0.1 \times 10^6$ cells/mL to about $3 \times 10^6$ cells/mL, about $0.1 \times 10^6$ cells/mL to about $2 \times 10^6$ cells/mL, about $0.1 \times 10^6$ cells/mL to about $1.5 \times 10^6$ cells/mL, about $0.1 \times 10^6$ cells/mL to about $1.0 \times 10^6$ cells/mL, about $0.1 \times 10^6$ cells/mL to about $0.8 \times 10^6$ cells/mL, about $0.1 \times 10^6$ cells/mL to about $0.5 \times 10^6$ cells/mL, about $0.1 \times 10^6$ cells/mL to about $0.3 \times 10^6$ cells/mL, about $0.2 \times 10^6$ cells/mL to about $10 \times 10^6$ cells/mL, about $0.2 \times 10^6$ cells/mL to about $9 \times 10^6$ cells/mL, about $0.2 \times 10^6$ cells/mL to about $8 \times 10^6$ cells/mL, about $0.2 \times 10^6$ cells/mL to about $7 \times 10^6$ cells/mL, about $0.2 \times 10^6$ cells/mL to about $6 \times 10^6$ cells/mL, about $0.2 \times 10^6$ cells/mL to about $5 \times 10^6$ cells/mL, about $0.2 \times 10^6$ cells/mL to about $4 \times 10^6$ cells/mL, about $0.2 \times 10^6$ cells/mL to about $3 \times 10^6$ cells/mL, about $0.2 \times 10^6$ cells/mL to about $2 \times 10^6$ cells/mL, about $0.2 \times 10^6$ cells/mL to about $1.5 \times 10^6$ cells/mL, about $0.2 \times 10^6$ cells/mL to about $1.0 \times 10^6$ cells/mL, about $0.2 \times 10^6$ cells/mL to about $0.8 \times 10^6$ cells/mL, about $0.2 \times 10^6$ cells/mL to about $0.5 \times 10^6$ cells/mL, about $0.3 \times 10^6$ cells/mL to about $10 \times 10^6$ cells/mL, about $0.3 \times 10^6$ cells/mL to about $9 \times 10^6$ cells/mL, about $0.3 \times 10^6$ cells/mL to about $8 \times 10^6$ cells/mL, about $0.3 \times 10^6$ cells/mL to about $7 \times 10^6$ cells/mL, about $0.3 \times 10^6$ cells/mL to about $6 \times 10^6$ cells/mL, about $0.3 \times 10^6$ cells/mL to about $5 \times 10^6$ cells/mL, about $0.3 \times 10^6$ cells/mL to about $4 \times 10^6$ cells/mL, about $0.3 \times 10^6$ cells/mL to about $3 \times 10^6$ cells/mL, about $0.3 \times 10^6$ cells/mL to about $2 \times 10^6$ cells/mL, about $0.3 \times 10^6$ cells/mL to about $1.5 \times 10^6$ cells/mL, about $0.3 \times 10^6$ cells/mL to about $1.0 \times 10^6$ cells/mL, about $0.3 \times 10^6$ cells/mL to about $0.8 \times 10^6$ cells/mL, about $0.3 \times 10^6$ cells/mL to about $0.5 \times 10^6$ cells/mL, about $0.5 \times 10^6$ cells/mL to about $10 \times 10^6$ cells/mL, about $0.5 \times 10^6$ cells/mL to about $9 \times 10^6$ cells/mL, about $0.5 \times 10^6$ cells/mL to about $8 \times 10^6$ cells/mL, about $0.5 \times 10^6$ cells/mL to about $7 \times 10^6$ cells/mL, about $0.5 \times 10^6$ cells/mL to about $6 \times 10^6$ cells/mL, about $0.5 \times 10^6$ cells/mL to about $5 \times 10^6$ cells/mL, about $0.5 \times 10^6$ cells/mL to about $4 \times 10^6$ cells/mL, about $0.5 \times 10^6$ cells/mL to about $3 \times 10^6$ cells/mL, about $0.5 \times 10^6$ cells/mL to about $2 \times 10^6$ cells/mL, about $0.5 \times 10^6$ cells/mL to about $1.5 \times 10^6$ cells/mL, about $0.5 \times 10^6$ cells/mL to about $1.0 \times 10^6$ cells/mL, about $0.5 \times 10^6$ cells/mL to about $0.8 \times 10^6$ cells/mL, about $0.8 \times 10^6$ cells/mL to about $10 \times 10^6$ cells/mL, about $0.8 \times 10^6$ cells/mL to about $9 \times 10^6$ cells/mL, about $0.8 \times 10^6$ cells/mL to about $8 \times 10^6$ cells/mL, about $0.8 \times 10^6$ cells/mL to about $7 \times 10^6$ cells/mL, about $0.8 \times 10^6$ cells/mL to about $6 \times 10^6$ cells/mL, about $0.8 \times 10^6$ cells/mL to about $5 \times 10^6$ cells/mL, about $0.8 \times 10^6$ cells/mL to about $4 \times 10^6$ cells/mL, about $0.8 \times 10^6$ cells/mL to about $3 \times 10^6$ cells/mL, about $0.8 \times 10^6$ cells/mL to about $2 \times 10^6$ cells/mL, about $0.8 \times 10^6$ cells/mL to about $1.5 \times 10^6$ cells/mL, about $0.8 \times 10^6$ cells/mL to about $1.0 \times 10^6$ cells/mL, about $1.0 \times 10^6$ cells/mL to about $10 \times 10^6$ cells/mL, about $1.0 \times 10^6$ cells/mL to about $9 \times 10^6$ cells/mL, about $1.0 \times 10^6$ cells/mL to about $8 \times 10^6$ cells/mL, about $1.0 \times 10^6$ cells/mL to about $7 \times 10^6$ cells/mL, about $1.0 \times 10^6$ cells/mL to about $6 \times 10^6$ cells/mL, about $1.0 \times 10^6$ cells/mL to about $5 \times 10^6$ cells/mL, about $1.0 \times 10^6$ cells/mL to about $4 \times 10^6$ cells/mL, about $1.0 \times 10^6$ cells/mL to about $3 \times 10^6$ cells/mL, about $1.0 \times 10^6$ cells/mL to about $2 \times 10^6$ cells/mL, about $1.0 \times 10^6$ cells/mL to about $1.5 \times 10^6$ cells/mL, about $1.5 \times 10^6$ cells/mL to about $10 \times 10^6$ cells/mL, about $1.5 \times 10^6$ cells/mL to about $9 \times 10^6$ cells/mL, about $1.5 \times 10^6$ cells/mL to about $8 \times 10^6$ cells/mL, about $1.5 \times 10^6$ cells/mL to about $7 \times 10^6$ cells/mL, about $1.5 \times 10^6$ cells/mL to about $6 \times 10^6$ cells/mL, about $1.5 \times 10^6$ cells/mL to about $5 \times 10^6$ cells/mL, about $1.5 \times 10^6$ cells/mL to about $4 \times 10^6$ cells/mL, about $1.5 \times 10^6$ cells/mL to about $3 \times 10^6$ cells/mL, about $1.5 \times 10^6$ cells/mL to about $2 \times 10^6$ cells/mL, about $2 \times 10^6$ cells/mL to about $10 \times 10^6$ cells/mL, about $2 \times 10^6$ cells/mL to about $9 \times 10^6$ cells/mL, about $2 \times 10^6$ cells/mL to about $8 \times 10^6$ cells/mL, about $2 \times 10^6$ cells/mL to about $7 \times 10^6$ cells/mL, about $2 \times 10^6$ cells/mL to about $6 \times 10^6$ cells/mL, about $2 \times 10^6$ cells/mL to about $5 \times 10^6$ cells/mL, about $2 \times 10^6$ cells/mL to about $4 \times 10^6$ cells/mL, about $2 \times 10^6$ cells/mL to about $3 \times 10^6$ cells/mL, about $3 \times 10^6$ cells/mL to about $10 \times 10^6$ cells/mL, about $3 \times 10^6$ cells/mL to about $9 \times 10^6$ cells/mL, about $3 \times 10^6$ cells/mL to about $8 \times 10^6$ cells/mL, about $3 \times 10^6$ cells/mL to about $7 \times 10^6$ cells/mL, about $3 \times 10^6$ cells/mL to about $6 \times 10^6$ cells/mL, about $3 \times 10^6$ cells/mL to about $5 \times 10^6$ cells/mL, about $3 \times 10^6$ cells/mL to about $4 \times 10^6$ cells/mL, about $4 \times 10^6$ cells/mL to about $10 \times 10^6$ cells/mL, about $4 \times 10^6$ cells/mL to about $9 \times 10^6$ cells/mL, about $4 \times 10^6$ cells/mL to about $8 \times 10^6$ cells/mL, about $4 \times 10^6$ cells/mL to about $7 \times 10^6$ cells/mL, about $4 \times 10^6$ cells/mL to about $6 \times 10^6$ cells/mL, about $4 \times 10^6$ cells/mL to about $5 \times 10^6$ cells/mL, about $5 \times 10^6$ cells/mL to about $10 \times 10^6$ cells/mL, about $5 \times 10^6$ cells/mL to about $9 \times 10^6$ cells/mL, about $5 \times 10^6$ cells/mL to about $8 \times 10^6$ cells/mL, about $5 \times 10^6$ cells/mL to about $7 \times 10^6$ cells/mL, about $5 \times 10^6$ cells/mL to about $6 \times 10^6$ cells/mL, about $6 \times 10^6$ cells/mL to about $10 \times 10^6$ cells/mL, about $6 \times 10^6$ cells/mL to about $9 \times 10^6$ cells/mL, about $6 \times 10^6$ cells/mL to about $8 \times 10^6$ cells/mL, about $6 \times 10^6$ cells/mL to about $7 \times 10^6$ cells/mL, about $7 \times 10^6$ cells/mL to about $10 \times 10^6$ cells/mL, about $7 \times 10^6$ cells/mL to about $9 \times 10^6$ cells/mL, about $7 \times 10^6$ cells/mL to about $8 \times 10^6$ cells/mL, about $8 \times 10^6$ cells/mL to about $10 \times 10^6$ cells/mL, about $8 \times 10^6$ cells/mL to about $9 \times 10^6$ cells/mL, or about $9 \times 10^6$ cells/mL to about $10 \times 10^6$ cells/mL).

The cell (e.g., mammalian cell) can contain a recombinant nucleic acid (e.g., a nucleic acid stably integrated in the cell's genome) that encodes a recombinant therapeutic protein (e.g., a recombinant therapeutic protein that is secreted by the cell). Non-limiting examples of recombinant therapeutic proteins are described herein and are known in the art.

Recombinant Therapeutic Proteins

A recombinant therapeutic protein can be a secreted protein that is released by the cell (e.g., mammalian cell) into the liquid culture medium of the cell culture. For example, a nucleic acid sequence encoding a soluble recombinant protein can contain a sequence that encodes a secretion signal peptide at the N- or C-terminus of the recombinant protein, which is cleaved by an enzyme present in the cell (e.g., mammalian cell), and subsequently released into the liquid culture medium of the cell culture. In other instances, the recombinant protein is a soluble protein that is not secreted, and the recombinant protein is recovered from within the cell (e.g., mammalian cell).

Non-limiting examples of recombinant proteins include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., human erythropoietin, tumor necrosis factor (TNF), or an interferon alpha or beta), or immunogenic or antigenic proteins or protein fragments (e.g., proteins for use in a vaccine). In some embodiments, the recombinant protein is an engineered antigen-binding polypeptide that contains at least one multifunctional recombinant protein scaffold (see, e.g., the recombinant antigen-binding proteins described in Gebauer et al., *Current Opin. Chem. Biol.* 13:245-255, 2009; and U.S. Patent Application Publication No. 2012/0164066 (herein incorporated by reference in its entirety)). Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies are known in the art. Additional non-limiting examples of recombinant proteins include: alglucosidase alfa, laronidase, abatacept, galsulfase, lutropin alfa, antihemophilic factor, agalsidase beta, interferon beta-la, darbepoetin alfa, tenecteplase, etanercept, coagulation factor IX, follicle stimulating hormone, interferon beta-la, imiglucerase, dornase alfa, epoetin alfa, and alteplase.

A secreted, soluble recombinant protein can be recovered from the liquid culture medium. A variety of different methods for removing liquid culture medium from cells (e.g., mammalian cells) are known in the art, including, for example, centrifugation, filtration, pipetting, and/or aspiration. The secreted recombinant protein can then be recovered and further purified from the liquid culture medium using a variety of biochemical techniques including various types of chromatography (e.g., affinity chromatography, molecular sieve chromatography, cation exchange chromatography, or anion exchange chromatography) and/or filtration (e.g., molecular weight cut-off filtration).

To recover an intracellular recombinant protein, the cell (e.g., mammalian cell) can be lysed. A wide variety of methods for lysing cells (e.g., mammalian cells) are known in the art, including, for example, sonication and/or detergent, enzymatic, and/or chemical lysis. A recombinant protein can be purified from a cell lysate (e.g., a mammalian cell lysate) using a variety of biochemical methods known in the art, typically starting with a step of centrifugation to remove the cellular debris, and then one or more additional steps (e.g., one or more types of chromatography (e.g., affinity chromatography, molecular sieve chromatography, cation exchange chromatography, or anion exchange chromatography) and/or filtration (e.g., molecular weight cut-off filtration)).

In some embodiments, the recovered recombinant protein is at least or about 50% pure by weight, e.g., at least or about 55% pure by weight, at least 60% pure by weight, at least 65% pure by weight, at least 70% pure by weight, at least 75% pure by weight, at least 80% pure by weight, at least 85% pure by weight, at least 90% pure by weight, at least 95% pure by weight, at least 96% pure by weight, at least 97% pure by weight, at least 98% pure by weight, or at least or about 99% pure by weight, or greater than 99% pure by weight.

In some embodiments, the recovered recombinant protein is a recombinant human therapeutic protein that has one or more different biophysical properties as compared to the same native protein in a human (e.g., differences in the type or amount of glycosylation, differences in phosphorylation, differences in acylation, differences in metallation or metal stoichiometry, and/or differences in cofactor binding).

Also provided herein is a recombinant therapeutic protein produced by any of the methods described herein.

Liquid Culture Media

Liquid culture media are known in the art. The liquid culture medium can be supplemented with a mammalian serum (e.g., fetal calf serum and bovine serum), and/or a growth hormone or growth factor (e.g., insulin, transferrin, and epidermal growth factor). Alternatively or in addition, liquid culture medium can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture medium can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these or other additives.

Non-limiting examples of liquid culture media that are particularly useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid tissue culture medium and medium components are known in the art.

Perfusion Culturing

The culturing of a cell can be performed using perfusion culturing. Perfusion culturing a cell (e.g., a mammalian cell) in a vessel includes the removal from the vessel of a first volume of a first liquid culture medium (e.g., containing any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the vessel or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the vessel or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the vessel volume or the first liquid culture medium volume to about 25% to about 150% of the vessel volume or the first liquid culture medium volume.

Skilled practitioners will appreciate that the first liquid culture medium and the second liquid culture medium can be the same type of media. In other instances, the first liquid culture medium and the second liquid culture medium can be different.

The first volume of the first liquid culture medium can be removed, e.g., by a mechanical system that can remove the first volume of the first liquid culture medium from the vessel (e.g., the first volume of the first liquid culture medium that is substantially free of cells from the bioreactor). Alternatively or in addition, the first volume of the first liquid culture medium can be removed by seeping or gravity flow of the first volume of the first liquid culture medium through a sterile membrane with a molecular weight cut-off that excludes the cell (e.g., mammalian cell).

The second volume of the second liquid culture medium can be added to the first liquid culture medium in an automated fashion, e.g., by perfusion pump.

In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the vessel with a cell (e.g., a mammalian cell).

Fed-Batch Culturing

The culturing of a cell (e.g., a mammalian cell) can be performed using fed-batch culturing. Fed-batch culturing a cell (e.g., a mammalian cell) includes, over the majority of the culturing period, the addition (e.g., periodic or continuous addition) to a first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the vessel or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the vessel or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the vessel volume or the first liquid culture medium volume to about 25% to about 150% of the vessel volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media. In other instances, the first liquid culture medium and the second liquid culture medium can be different. The volume of the second liquid culture medium can be added to the first liquid culture medium in an automated fashion, e.g., by perfusion pump.

In some instances, adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the vessel with a cell (e.g., a mammalian cell). The cell culture medium in fed-batch cultures is typically harvested at the end of culture period and used in any of the processes described herein, however, the cell culture medium in fed-batch cultures can also be harvested at one or more time points during the culturing period and used in any of the processes described herein.

Skilled practitioners will appreciate that any of the various culture parameters (e.g., vessels, volumes, rates or frequencies of replacing culture volumes, agitation frequencies, temperatures, media, and $CO_2$ concentrations) can be used in any combination in to perform these methods.

Temperature

Culturing can be performed at a temperature of 32° C. to about 39° C., e.g., about 32° C. to about 37° C. Skilled practitioners will appreciate that the temperature can be changed at specific time point(s) in the culturing method (e.g., during one or more of the first time period, the second time period, and the third time period), e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the shake flask with the mammalian cell) or at any time point within the first, second, and/or third time periods described herein. For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C.). For example, the temperature can be shifted downwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.).

$CO_2$

Culturing can include incubating a cell culture in an atmosphere containing at most or about 1% to 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$). Culturing can include incubating a cell culture in a humidified atmosphere (e.g., at least or about 20%, 30%, 40%, 50%, 60%, 70%, 85%, 80%, 85%, 90%, or at least or about 95% humidity, or about 100% humidity).

Cell Viability Measurement

A variety of methods and assays that can be used to determine cell viability of a cell culture (e.g., a mammalian cell culture) are known in the art. For example, lactate dehydrogenase (LDH) can be detected in a liquid culture medium of a cell culture. Commercial kits for detection of LDH in a liquid culture medium of a cell culture are known in the art.

A variety of different dyes which are excluded by viable cells, but selectively taken up by non-viable cells are used to determine cell viability. Non-limiting examples of these dyes include propidium iodide, trypan blue, and 7-aminoactinomycin D. The viability of the cells is determined by visualizing or otherwise detecting the staining of the cells after incubation with the dye.

Additional assays for determining cell viability of a culture of cells include the detection of mitochondrial activity or caspase activity in the cells (e.g., Resazurin and Formazan). Additional methods for determining cell viability in a culture of cells are known in the art.

Methods of Predicting the Effect of a Concentration of a Sensitizer on Cell Viability in a Production Bioreactor Provided herein are methods of predicting the effect of a concentration of a sensitizer (e.g., any of the sensitizers described herein or known in the art) on cell viability in a production bioreactor that include: (a) determining cell viability under a plurality of test conditions in a test culture vessel (e.g., any of the test culture vessels described herein), where the plurality of test conditions are defined by a set of parameters; and (b) based on the cell viability in the test culture vessel under the plurality of conditions, predicting the effect of a concentration of a sensitizer on cell viability in a production bioreactor (e.g., any of the production bioreactors described herein).

In some embodiments, the set of parameters includes, consists, or consists essentially of shear stress, concentration of the sensitizer, and concentration of a protectant (e.g., any of the protectants described herein). In some embodiments of these methods, the plurality of testing conditions are selected based on full factorial screening and/or inscribed center composite design. In some embodiments of any of these methods, the sensitizer is an antifoam (e.g., a polydimethylsiloxane-based antifoam, simethicone, or any other antifoam described herein or known in the art).

In some embodiments, the test culture vessel (e.g., any of the exemplary test culture vessels described herein or known in the art) has a volume of about 5 mL to about 5 L (or any of the subranges of this range described herein). In some embodiments, the test culture vessel is a shake flask, e.g., a baffled shake flask.

In some embodiments, the production bioreactor (e.g., any of the exemplary production bioreactors described herein or known in the art) has a volume of about 5 L to about 20,000 L (or any of the subranges of this range described herein). In some examples, the production bioreactor is a perfusion bioreactor. In other examples, the production bioreactor is a fed batch bioreactor.

The specific cell death rate as described herein is defined by the formula below:

Specific cell death rate=(specific LDH production)/(LDH content per cell).

Some embodiments of these methods further include culturing a cell (e.g., any of the cells described herein) in the production bioreactor using a concentration of the sensitizer predicted to have a specific cell death rate of less 40% per day, less than 39% per day, less than 38% per day, less than 37% per day, less than 36% per day, less than 35% per day, less than 34% per day, less than 33% per day, less than 32% per day, less than 31% per day, less than 30% per day, less than 29% per day, less than 28% per day, less than 27% per day, less than 26% per day, less than 25% per day, less than 24% per day, less than 23% per day, less than 22% per day, less than 21% per day, less than 20% per day, less than 19% per day, less than 18% per day, less than 17% per day, less than 16% per day, less than 15% per day, less than 14% per day, less than 13% per day, less than 12% per day, less than 11% per day, less than 10% per day, less than 9% per day, less than 8% per day, less than 7% per day, less than 6% per day, less than 5% per day, less than 4% per day, less than 3% per day, less than 2% per day, or less than 1% per day, during the culturing of the cell (e.g., any of the cells described herein) in the production bioreactor. Some embodiments of any of the methods described herein further include culturing a cell (e.g., any of the cells described herein) in the production bioreactor using a concentration of the sensitizer predicted to have a specific cell death rate of about 0.1% to about 40% per day, about 0.1% to about 38% per day, about 0.1% to about 36% per day, about 0.1% to about 34% per day, about 0.1% to about 32% per day, about 0.1% to about 30% per day, about 0.1% to about 28% per day, about 0.1% to about 26% per day, about 0.1% to about 24% per day, about 0.1% to about 22% per day, about 0.1% to about 20% per day, about 0.1% to about 18% per day, about 0.1% to about 16% per day, about 0.1% to about 14% per day, about 0.1% to about 12% per day, about 0.1% to about 10% per day, about 0.1% to about 8% per day, about 0.1% to about 6% per day, about 0.1% to about 5% per day, about 0.1% to about 4.5% per day, about 0.1% to about 4.0% per day, about 0.1% to about 3.5% per day, about 0.1% to about 3.0% per day, about 0.1% to about 2.5% per day, about 0.1% to about 2.0% per day, about 0.1% to about 1.5% per day, about 0.1% to about 1.0% per day, about 0.1% to about 0.5% per day, about 0.5% to about 40% per day, about 0.5% to about 38% per day, about 0.5% to about 36% per day, about 0.5% to about 34% per day, about 0.5% to about 32% per day, about 0.5% to about 30% per day, about 0.5% to about 28% per day, about 0.5% to about 26% per day, about 0.5% to about 24% per day, about 0.5% to about 22% per day, about 0.5% to about 20% per day, about 0.5% to about 18% per day, about 0.5% to about 16% per day, about 0.5% to about 14% per day, about 0.5% to about 12% per day, about 0.5% to about 10% per day, about 0.5% to about 8% per day, about 0.5% to about 6% per day, about 0.5% to about 5% per day, about 0.5% to about 4.5% per day, about 0.5% to about 4.0% per day, about 0.5% to about 3.5% per day, about 0.5% to about 3.0% per day, about 0.5% to about 2.5% per day, about 0.5% to about 2.0% per day, about 0.5% to about 1.5% per day, about 0.5% to about 1.0% per day, about 1.0% to about 40% per day, about 1.0% to about 38% per day, about 1.0% to about 36% per day, about 1.0% to about 34% per day, about 1.0% to about 32% per day, about 1.0% to about 30% per day, about 1.0% to about 28% per day, about 1.0% to about 26% per day, about 1.0% to about 24% per day, about 1.0% to about 22% per day, about 1.0% to about 20% per day, about 1.0% to about 18% per day, about 1.0% to about 16% per day, about 1.0% to about 14% per day, about 1.0% to about 12% per day, about 1.0% to about 10% per day, about 1.0% to about 8% per day, about 1.0% to about 6% per day, about 1.0% to about 5% per day, about 1.0% to about 4.5% per day, about 1.0% to about 4.0% per day, about 1.0% to about 3.5% per day, about 1.0% to about 3.0% per day, about 1.0% to about 2.5% per day, about 1.0% to about 2.0% per day, about 1.0% to about 1.5% per day, about 1.5% to about 40% per day, about 1.5% to about 38% per day, about 1.5% to about 36% per day, about 1.5% to about 34% per day, about 1.5% to about 32% per day, about 1.5% to about 30% per day, about 1.5% to about 28% per day, about 1.5% to about 26% per day, about 1.5% to about 24% per day, about 1.5% to about 22% per day, about 1.5% to about 20% per day, about 1.5% to about 18% per day, about 1.5% to about 16% per day, about 1.5% to about 14% per day, about 1.5% to about 12% per day, about 1.5% to about 10% per day, about 1.5% to about 8% per day, about 1.5% to about 6% per day, about 1.5% to about 5% per day, about 1.5% to about 4.5% per day, about 1.5% to about 4.0% per day, about 1.5% to about 3.5% per day, about 1.5% to about 3.0% per day, about 1.5% to about 2.5% per day, about 1.5% to about 2.0% per day, about 2.0% to about 40% per day, about 2.0% to about 38% per day, about 2.0% to about 36% per day, about 2.0% to about 34% per day, about 2.0% to about 32% per day, about 2.0% to about 30% per day, about 2.0% to about 28% per day, about 2.0% to about 26% per day, about 2.0% to about 24% per day, about 2.0% to about 22% per day, about 2.0% to about 20% per day, about 2.0% to about 18% per day, about 2.0% to about 16% per day, about 2.0% to about 14% per day, about 2.0% to about 12% per day, about 2.0% to about 10% per day, about 2.0% to about 8% per day, about 2.0% to about 6% per day, about 2.0% to about 5% per day, about 2.0% to about 4.5% per day, about 2.0% to about 4.0% per day, about 2.0% to about 3.5% per day, about 2.0% to about 3.0% per day, about 2.0% to about 2.5% per day, about 2.5% to about 40% per day, about 2.5% to about 38% per day, about 2.5% to about 36% per day, about 2.5% to about 34% per day, about 2.5% to about 32% per day, about 2.5% to about 30% per day, about 2.5% to about 28% per day, about 2.5% to about 26% per day, about 2.5% to about 24% per day, about 2.5% to about 22% per day, about 2.5% to about 20% per day, about 2.5% to about 18% per day, about 2.5% to about 16% per day, about 2.5% to about 14% per day, about 2.5% to about 12% per day, about 2.5% to about 10% per day, about 2.5% to about 8% per day, about 2.5% to about 6% per day, about 2.5% to about 5% per day, about 2.5% to about 4.5% per day, about 2.5% to about 4.0% per day, about 2.5% to about 3.5% per day, about 2.5% to about 3.0% per day, about 3.0% to about 40% per day, about 3.0% to about 38% per day, about 3.0% to about 36% per day, about 3.0% to about 34% per day, about 3.0% to about 32% per day, about 3.0% to about 30% per day, about 3.0% to about 28% per day, about 3.0% to about 26% per day, about 3.0% to about 24% per day, about 3.0% to about 22% per day, about 3.0% to about 20% per day, about 3.0% to about 18% per day, about 3.0% to about 16% per day, about 3.0% to about 14% per day, about 3.0% to about 12% per day, about 3.0% to about 10% per day, about 3.0% to about 8% per day, about 3.0% to about 6% per day, about 3.0% to about 5% per day, about 3.0% to about 4.5% per day, about 3.0% to about 4.0% per day, about 3.0% to about 3.5% per day, about 3.5% to about 40% per day, about 3.5% to about 38% per day, about 3.5% to about 36% per day, about 3.5% to about 34% per day, about 3.5% to about 32% per day, about 3.5% to about 30% per day, about 3.5% to about 28% per day, about 3.5% to about 26% per day, about 3.5% to about 24% per day, about 3.5% to about 22% per day, about 3.5% to about 20% per day, about 3.5% to about 18% per day, about 3.5% to about 16% per day, about 3.5% to about 14% per day, about 3.5% to about 12% per day, about 3.5% to about 10% per day, about 3.5% to about 8% per day, about 3.5% to about 6% per day, about 3.5% to about 5% per day, about 3.5% to about 4.5% per day, about 3.5% to about 4.0% per day, about 4.0% to about 40% per day, about 4.0% to about 38% per day, about 4.0% to about 36% per day, about 4.0% to about 34% per day, about 4.0% to about 32% per day, about 4.0% to about 30% per day, about 4.0% to about 28% per day, about 4.0% to about 26% per day, about 4.0% to about 24% per day, about 4.0% to about 22% per day, about 4.0% to about 20% per day, about 4.0% to about 18% per day, about 4.0% to about 16% per day, about 4.0% to about 14% per day, about 4.0% to about 12% per day, about 4.0% to about 10% per day, about 4.0% to about 8% per day, about 4.0% to about 6% per day, about 4.0% to about 5% per day, about 4.0% to about 4.5% per day, about 4.5% to about 40% per day, about 4.5% to about 38% per day, about 4.5% to about 36% per day, about 4.5% to about 34% per day, about 4.5% to about 32% per day, about 4.5% to about 30% per day, about 4.5% to about 28% per day, about 4.5% to about 26% per day, about 4.5% to about 24% per day, about 4.5% to about 22% per day, about 4.5% to about 20% per day, about 4.5% to about 18% per day, about 4.5% to about 16% per day, about 4.5% to about 14% per day, about 4.5% to about 12% per day, about 4.5% to about 10% per day, about 4.5% to about 8% per day, about 4.5% to about 6% per day, about 4.5% to about 5% per day, about 5% to about 40% per day, about 5% to about 38% per day, about 5% to about 36% per day, about 5% to about 34% per day, about 5% to about 32% per day, about 5% to about 30% per day, about 5% to about 28% per day, about 5% to about 26% per day, about 5% to about 24% per day, about 5% to about 22% per day, about 5% to about 20% per day, about 5% to about 18% per day, about 5% to about 16% per day, about 5% to about 14% per day, about 5% to about 12% per day, about 5% to about 10% per day, about 5% to about 8% per day, about 5% to about 6% per day, about 6% to about 40% per day, about 6% to about 38% per day, about 6% to about 36% per day, about 6% to about 34% per day, about 6% to about 32% per day, about 6% to about 30% per day, about 6% to about 28% per day, about 6% to about 26% per day, about 6% to about 24% per day, about 6% to about 22% per day, about 6% to about 20% per day, about 6% to about 18% per day, about 6% to about 16% per day, about 6% to about 14% per day, about 6% to about 12% per day, about 6% to about 10% per day, about 6% to about 8% per day, about 8% to about 40% per day, about 8% to about 38% per day, about 8% to about 36% per day, about 8% to about 34% per day, about 8% to about 32% per day, about 8% to about 30% per day, about 8% to about 28% per day, about 8% to about 26% per day, about 8% to about 24% per day, about 8% to about 22% per day, about 8% to about 20% per day, about 8% to about 18% per day, about 8% to about 16% per day, about 8% to about 14% per day, about 8% to about 12% per day, about 8% to about 10% per day, about 10% to about 40% per day, about 10% to about 38% per day, about 10% to about 36% per day, about 10% to about 34% per day, about 10% to about 32% per day, about 10% to about 30% per day, about 10% to about 28% per day, about 10% to about 26% per day, about 10% to about 24% per day, about 10% to about 22% per day, about 10% to about 20% per day, about 10% to about 18% per day, about 10% to about 16% per day, about 10% to about 14% per day, about 10% to about 12% per day, about 12% to about 40% per day, about 12% to about 38% per day, about 12% to about 36% per day, about 12% to about 34% per day, about 12% to about 32% per day, about 12% to about 30% per day, about 12% to about 28% per day, about 12% to about 26% per day, about 12% to about 24% per day, about 12% to about 22% per day, about 12% to about 20% per day, about 12% to about 18% per day, about 12% to about 16% per day, about 12% to about 14% per day, about 14% to about 40% per day, about 14% to about 38% per day, about 14% to about 36% per day, about 14% to about 34% per day, about 14% to about 32% per day, about 14% to about 30% per day, about 14% to about 28% per day, about 14% to about 26% per day, about 14% to about 24% per day, about 14% to about 22% per day, about 14% to about 20% per day, about 14% to about 18% per day, about 14% to about 16% per day, about 16% to about 40% per day, about 16% to about 38% per day, about 16% to about 36% per day, about 16% to about 34% per day, about 16% to about 32% per day, about 16% to about 30% per day, about 16% to about 28% per day, about 16% to about 26% per day, about 16% to about 24% per day, about 16% to about 22% per day, about 16% to about 20% per day, about 16% to about 18% per day, about 18% to about 40% per day, about 18% to about 38% per day, about 18% to about 36% per day, about 18% to about 34% per day, about 18% to about 32% per day, about 18% to about 30% per day, about 18% to about 28% per day, about 18% to about 26% per day, about 18% to about 24% per day, about 18% to about 22% per day, about 18% to about 20% per day, about 20% to about 40% per day, about 20% to about 38% per day, about 20% to about 36% per day, about 20% to about 34% per day, about 20% to about 32% per day, about 20% to about 30% per day, about 20% to about 28% per day, about 20% to about 26% per day, about 20% to about 24% per day, about 20% to about 22% per day, about 22% to about 40% per day, about 22% to about 38% per day, about 22% to about 36% per day, about 22% to about 34% per day, about 22% to about 32% per day, about 22% to about 30% per day, about 22% to about 28% per day, about 22% to about 26% per day, about 22% to about 24% per day, about 24% to about 40% per day, about 24% to about 38% per day, about 24% to about 36% per day, about 24% to about 34% per day, about 24% to about 32% per day, about 24% to about 30% per day, about 24% to about 28% per day, about 24% to about 26% per day, about 26% to about 40% per day, about 26% to about 38% per day, about 26% to about 36% per day, about 26% to about 34% per day, about 26% to about 32% per day, about 26% to about 30% per day, about 26% to about 28% per day, about 28% to about 40% per day, about 28% to about 38% per day, about 28% to about 36% per day, about 28% to about 34% per day, about 28% to about 32% per day, about 28% to about 30% per day, about 30% to about 40% per day, about 30% to about 38% per day, about 30% to about 36% per day, about 30% to about 34% per day, about 30% to about 32% per day, about 32% to about 40% per day, about 32% to about 38% per day, about 32% to about 36% per day, about 32% to about 34% per day, about 34% to about 40% per day, about 34% to about 38% per day, about 34% to about 36% per day, about 36% to about 40% per day, about 36% to about 38% per day, or about 38% to about 40% per day, during the culturing of the cell (e.g., any of the cells described herein) in the production bioreactor.

Some embodiments of these methods further include culturing a cell (e.g., any of the cells described herein) in the production bioreactor (e.g., any of the production bioreactors described herein) using a concentration of the sensitizer predicted to result in a cell specific LDH production of less than 150 nU/cell/day, less than 145 nU/cell/day, less than 140 nU/cell/day, less than 135 nU/cell/day, less than 130 nU/cell/day, less than 125 nU/cell/day, less than 120 nU/cell/day, less than 115 nU/cell/day, less than 150 nU/cell/day, less than 110 nU/cell/day, less than 105 nU/cell/day, less than 100 nU/cell/day, less than 95 nU/cell/day, less than 90 nU/cell/day, less than 85 nU/cell/day, less than 80 nU/cell/day, less than 75 nU/cell/day, less than 70 nU/cell/day, less than 65 nU/cell/day, less than 60 nU/cell/day, less than 55 nU/cell/day, less than 50 nU/cell/day, less than 45 nU/cell/day, less than 45 nU/cell/day, less than 40 nU/cell/day, less than 35 nU/cell/day, less than 30 nU/cell/day, less than 25 nU/cell/day, less than 20 nU/cell/day, less than 15 nU/cell/day, less than 10 nU/cell/day, less than 5 nU/cell/day, or less than less than 1 nU/cell/day, during the culturing of the cell in the production bioreactor. Some embodiments of these methods further include culturing a cell (e.g., any of the cells described herein) in the production bioreactor (e.g., any of the production bioreactors described herein) using a concentration of the sensitizer predicted to result in a cell specific LDH production of about 0.1 nU/cell/day to about 150 nU/cell/day, about 0.1 nU/cell/day to about 140 nU/cell/day, about 0.1 nU/cell/day to about 130 nU/cell/day, about 0.1 nU/cell/day to about 120 nU/cell/day, about 0.1 nU/cell/day to about 110 nU/cell/day, about 0.1 nU/cell/day to about 100 nU/cell/day, about 0.1 nU/cell/day to about 95 nU/cell/day, about 0.1 nU/cell/day to about 90 nU/cell/day, about 0.1 nU/cell/day to about 85 nU/cell/day, about 0.1 nU/cell/day to about 80 nU/cell/day, about 0.1 nU/cell/day to about 75 nU/cell/day, about 0.1 nU/cell/day to about 70 nU/cell/day, about 0.1 nU/cell/day to about 65 nU/cell/day, about 0.1 nU/cell/day to about 60 nU/cell/day, about 0.1 nU/cell/day to about 55 nU/cell/day, about 0.1 nU/cell/day to about 50 nU/cell/day, about 0.1 nU/cell/day to about 45 nU/cell/day, about 0.1 nU/cell/day to about 40 nU/cell/day, about 0.1 nU/cell/day to about 35 nU/cell/day, about 0.1 nU/cell/day to about 30 nU/cell/day, about 0.1 nU/cell/day to about 25 nU/cell/day, about 0.1 nU/cell/day to about 20 nU/cell/day, about 0.1 nU/cell/day to about 15 nU/cell/day, about 0.1 nU/cell/day to about 10 nU/cell/day, about 0.1 nU/cell/day to about 5 nU/cell/day, about 0.1 nU/cell/day to about 2.5 nU/cell/day, about 0.1 nU/cell/day to about 1.0 nU/cell/day, about 1.0 nU/cell/day to about 150 nU/cell/day, about 1.0 nU/cell/day to about 140 nU/cell/day to about 130 nU/cell/day, about 1.0 nU/cell/day to about 120 nU/cell/day, about 1.0 nU/cell/day to about 110 nU/cell/day, about 1.0 nU/cell/day to about 100 nU/cell/day, about 1.0 nU/cell/day to about 95 nU/cell/day to about 90 nU/cell/day, about 1.0 nU/cell/day to about 85 nU/cell/day, about 1.0 nU/cell/day to about 80 nU/cell/day, about 1.0 nU/cell/day to about 75 nU/cell/day, about 1.0 nU/cell/day to about 70 nU/cell/day, about 1.0 nU/cell/day to about 65 nU/cell/day, about 1.0 nU/cell/day to about 60 nU/cell/day, about 1.0 nU/cell/day to about 55 nU/cell/day, about 1.0 nU/cell/day to about 50 nU/cell/day, about 1.0 nU/cell/day to about 45 nU/cell/day, about 1.0 nU/cell/day to about 40 nU/cell/day, about 1.0 nU/cell/day to about 35 nU/cell/day, about 1.0 nU/cell/day to about 30 nU/cell/day, about 1.0 nU/cell/day to about 25 nU/cell/day, about 1.0 nU/cell/day to about 20 nU/cell/day, about 1.0 nU/cell/day to about 15 nU/cell/day, about 1.0 nU/cell/day to about 10 nU/cell/day, about 1.0 nU/cell/day to about 5 nU/cell/day, about 1.0 nU/cell/day to about 2.5 nU/cell/day, about 2.5 nU/cell/day to about 150 nU/cell/day, about 2.5 nU/cell/day to about 140 nU/cell/day, about 2.5 nU/cell/day to about 130 nU/cell/day, about 2.5 nU/cell/day to about 120 nU/cell/day, about 2.5 nU/cell/day to about 110 nU/cell/day, about 2.5 nU/cell/day to about 100 nU/cell/day, about 2.5 nU/cell/day to about 95 nU/cell/day, about 2.5 nU/cell/day to about 90 nU/cell/day, about 2.5 nU/cell/day to about 85 nU/cell/day, about 2.5 nU/cell/day to about 80 nU/cell/day, about 2.5 nU/cell/day to about 75 nU/cell/day, about 2.5 nU/cell/day to about 70 nU/cell/day, about 2.5 nU/cell/day to about 65 nU/cell/day, about 2.5 nU/cell/day to about 60 nU/cell/day, about 2.5 nU/cell/day to about 55 nU/cell/day, about 2.5 nU/cell/day to about 50 nU/cell/day, about 2.5 nU/cell/day to about 45 nU/cell/day, about 2.5 nU/cell/day to about 40 nU/cell/day, about 2.5 nU/cell/day to about 35 nU/cell/day, about 2.5 nU/cell/day to about 30 nU/cell/day, about 2.5 nU/cell/day to about 25 nU/cell/day, about 2.5 nU/cell/day to about 20 nU/cell/day, about 2.5 nU/cell/day to about 15 nU/cell/day, about 2.5 nU/cell/day to about 10 nU/cell/day, about 2.5 nU/cell/day to about 5 nU/cell/day, about 5 nU/cell/day to about 150 nU/cell/day, about 5 nU/cell/day to about 140 nU/cell/day, about 5 nU/cell/day to about 130 nU/cell/day, about 5 nU/cell/day to about 120 nU/cell/day, about 5 nU/cell/day to about 110 nU/cell/day, about 5 nU/cell/day to about 100 nU/cell/day, about 5 nU/cell/day to about 95 nU/cell/day, about 5 nU/cell/day to about 90 nU/cell/day, about 5 nU/cell/day to about 85 nU/cell/day, about 5 nU/cell/day to about 80 nU/cell/day, about 5 nU/cell/day to about 75 nU/cell/day, about 5 nU/cell/day to about 70 nU/cell/day, about 5 nU/cell/day to about 65 nU/cell/day, about 5 nU/cell/day to about 60 nU/cell/day, about 5 nU/cell/day to about 55 nU/cell/day, about 5 nU/cell/day to about 50 nU/cell/day, about 5 nU/cell/day to about 45 nU/cell/day, about 5 nU/cell/day to about 40 nU/cell/day, about 5 nU/cell/day to about 35 nU/cell/day, about 5 nU/cell/day to about 30 nU/cell/day, about 5 nU/cell/day to about 25 nU/cell/day, about 5 nU/cell/day to about 20 nU/cell/day, about 5 nU/cell/day to about 15 nU/cell/day, about 5 nU/cell/day to about 10 nU/cell/day, about 10 nU/cell/day to about 150 nU/cell/day, about 10 nU/cell/day to about 140 nU/cell/day, about 10 nU/cell/day to about 130 nU/cell/day, about 10 nU/cell/day to about 120 nU/cell/day, about 10 nU/cell/day to about 110 nU/cell/day, about 10 nU/cell/day to about 100 nU/cell/day, about 10 nU/cell/day to about 95 nU/cell/day, about 10 nU/cell/day to about 90 nU/cell/day, about 10 nU/cell/day to about 85 nU/cell/day, about 10 nU/cell/day to about 80 nU/cell/day, about 10 nU/cell/day to about 75 nU/cell/day, about 10 nU/cell/day to about 70 nU/cell/day, about 10 nU/cell/day to about 65 nU/cell/day, about 10 nU/cell/day to about 60 nU/cell/day, about 10 nU/cell/day to about 55 nU/cell/day, about 10 nU/cell/day to about 50 nU/cell/day, about 10 nU/cell/day to about 45 nU/cell/day, about 10 nU/cell/day to about 40 nU/cell/day, about 10 nU/cell/day to about 35 nU/cell/day, about 10 nU/cell/day to about 30 nU/cell/day, about 10 nU/cell/day to about 25 nU/cell/day, about 10 nU/cell/day to about 20 nU/cell/day, about 10 nU/cell/day to about 15 nU/cell/day, about 15 nU/cell/day to about 150 nU/cell/day, about 15 nU/cell/day to about 140 nU/cell/day, about 15 nU/cell/day to about 130 nU/cell/day, about 15 nU/cell/day to about 120 nU/cell/day, about 15 nU/cell/day to about 110 nU/cell/day, about 15 nU/cell/day to about 100 nU/cell/day, about 15 nU/cell/day to about 95 nU/cell/day, about 15 nU/cell/day to about 90 nU/cell/day, about 15 nU/cell/day to about 85 nU/cell/day, about 15 nU/cell/day to about 80 nU/cell/day, about 15 nU/cell/day to about 75 nU/cell/day, about 15 nU/cell/day to about 70 nU/cell/day, about 15 nU/cell/day to about 65 nU/cell/day, about 15 nU/cell/day to about 60 nU/cell/day, about 15 nU/cell/day to about 55 nU/cell/day, about 15 nU/cell/day to about 50 nU/cell/day, about 15 nU/cell/day to about 45 nU/cell/day, about 15 nU/cell/day to about 40 nU/cell/day, about 15 nU/cell/day to about 35 nU/cell/day, about 15 nU/cell/day to about 30 nU/cell/day, about 15 nU/cell/day to about 25 nU/cell/day, about 15 nU/cell/day to about 20 nU/cell/day, about 20 nU/cell/day to about 150 nU/cell/day, about 20 nU/cell/day to about 140 nU/cell/day, about 20 nU/cell/day to about 130 nU/cell/day, about 20 nU/cell/day to about 120 nU/cell/day, about 20 nU/cell/day to about 110 nU/cell/day, about 20 nU/cell/day to about 100 nU/cell/day, about 20 nU/cell/day to about 95 nU/cell/day, about 20 nU/cell/day to about 90 nU/cell/day, about 20 nU/cell/day to about 85 nU/cell/day, about 20 nU/cell/day to about 80 nU/cell/day, about 20 nU/cell/day to about 75 nU/cell/day, about 20 nU/cell/day to about 70 nU/cell/day, about 20 nU/cell/day to about 65 nU/cell/day, about 20 nU/cell/day to about 60 nU/cell/day, about 20 nU/cell/day to about 55 nU/cell/day, about 20 nU/cell/day to about 50 nU/cell/day, about 20 nU/cell/day to about 45 nU/cell/day, about 20 nU/cell/day to about 40 nU/cell/day, about 20 nU/cell/day to about 35 nU/cell/day, about 20 nU/cell/day to about 30 nU/cell/day, about 20 nU/cell/day to about 25 nU/cell/day, about 25 nU/cell/day to about 150 nU/cell/day, about 25 nU/cell/day to about 140 nU/cell/day, about 25 nU/cell/day to about 130 nU/cell/day, about 25 nU/cell/day to about 120 nU/cell/day, about 25 nU/cell/day to about 110 nU/cell/day, about 25 nU/cell/day to about 100 nU/cell/day, about 25 nU/cell/day to about 95 nU/cell/day, about 25 nU/cell/day to about 90 nU/cell/day, about 25 nU/cell/day to about 85 nU/cell/day, about 25 nU/cell/day to about 80 nU/cell/day, about 25 nU/cell/day to about 75 nU/cell/day, about 25 nU/cell/day to about 70 nU/cell/day, about 25 nU/cell/day to about 65 nU/cell/day, about 25 nU/cell/day to about 60 nU/cell/day, about 25 nU/cell/day to about 55 nU/cell/day, about 25 nU/cell/day to about 50 nU/cell/day, about 25 nU/cell/day to about 45 nU/cell/day, about 25 nU/cell/day to about 40 nU/cell/day, about 25 nU/cell/day to about 35 nU/cell/day, about 25 nU/cell/day to about 30 nU/cell/day, about 30 nU/cell/day to about 150 nU/cell/day, about 30 nU/cell/day to about 140 nU/cell/day, about 30 nU/cell/day to about 130 nU/cell/day, about 30 nU/cell/day to about 120 nU/cell/day, about 30 nU/cell/day to about 110 nU/cell/day, about 30 nU/cell/day to about 100 nU/cell/day, about 30 nU/cell/day to about 95 nU/cell/day, about 30 nU/cell/day to about 90 nU/cell/day, about 30 nU/cell/day to about 85 nU/cell/day, about 30 nU/cell/day to about 80 nU/cell/day, about 30 nU/cell/day to about 75 nU/cell/day, about 30 nU/cell/day to about 70 nU/cell/day, about 30 nU/cell/day to about 65 nU/cell/day, about 30 nU/cell/day to about 60 nU/cell/day, about 30 nU/cell/day to about 55 nU/cell/day, about 30 nU/cell/day to about 50 nU/cell/day, about 30 nU/cell/day to about 45 nU/cell/day, about 30 nU/cell/day to about 40 nU/cell/day, about 30 nU/cell/day to about 35 nU/cell/day, about 35 nU/cell/day to about 150 nU/cell/day, about 35 nU/cell/day to about 140 nU/cell/day, about 35 nU/cell/day to about 130 nU/cell/day, about 35 nU/cell/day to about 120 nU/cell/day, about 35 nU/cell/day to about 110 nU/cell/day, about 35 nU/cell/day to about 100 nU/cell/day, about 35 nU/cell/day to about 95 nU/cell/day, about 35 nU/cell/day to about 90 nU/cell/day, about 35 nU/cell/day to about 85 nU/cell/day, about 35 nU/cell/day to about 80 nU/cell/day, about 35 nU/cell/day to about 75 nU/cell/day, about 35 nU/cell/day to about 70 nU/cell/day, about 35 nU/cell/day to about 65 nU/cell/day, about 35 nU/cell/day to about 60 nU/cell/day, about 35 nU/cell/day to about 55 nU/cell/day, about 35 nU/cell/day to about 50 nU/cell/day, about 35 nU/cell/day to about 45 nU/cell/day, about 35 nU/cell/day to about 40 nU/cell/day, about 40 nU/cell/day to about 150 nU/cell/day, about 40 nU/cell/day to about 140 nU/cell/day, about 40 nU/cell/day to about 130 nU/cell/day, about 40 nU/cell/day to about 120 nU/cell/day, about 40 nU/cell/day to about 110 nU/cell/day, about 40 nU/cell/day to about 100 nU/cell/day, about 40 nU/cell/day to about 95 nU/cell/day, about 40 nU/cell/day to about 90 nU/cell/day, about 40 nU/cell/day to about 85 nU/cell/day, about 40 nU/cell/day to about 80 nU/cell/day, about 40 nU/cell/day to about 75 nU/cell/day, about 40 nU/cell/day to about 70 nU/cell/day, about 40 nU/cell/day to about 65 nU/cell/day, about 40 nU/cell/day to about 60 nU/cell/day, about 40 nU/cell/day to about 55 nU/cell/day, about 40 nU/cell/day to about 50 nU/cell/day, about 40 nU/cell/day to about 45 nU/cell/day, about 45 nU/cell/day to about 150 nU/cell/day, about 45 nU/cell/day to about 140 nU/cell/day, about 45 nU/cell/day to about 130 nU/cell/day, about 45 nU/cell/day to about 120 nU/cell/day, about 45 nU/cell/day to about 110 nU/cell/day, about 45 nU/cell/day to about 100 nU/cell/day, about 45 nU/cell/day to about 95 nU/cell/day, about 45 nU/cell/day to about 90 nU/cell/day, about 45 nU/cell/day to about 85 nU/cell/day, about 45 nU/cell/day to about 80 nU/cell/day, about 45 nU/cell/day to about 75 nU/cell/day, about 45 nU/cell/day to about 70 nU/cell/day, about 45 nU/cell/day to about 65 nU/cell/day, about 45 nU/cell/day to about 60 nU/cell/day, about 45 nU/cell/day to about 55 nU/cell/day, about 45 nU/cell/day to about 50 nU/cell/day, about 50 nU/cell/day to about 150 nU/cell/day, about 50 nU/cell/day to about 140 nU/cell/day, about 50 nU/cell/day to about 130 nU/cell/day, about 50 nU/cell/day to about 120 nU/cell/day, about 50 nU/cell/day to about 110 nU/cell/day, about 50 nU/cell/day to about 100 nU/cell/day, about 50 nU/cell/day to about 95 nU/cell/day, about 50 nU/cell/day to about 90 nU/cell/day, about 50 nU/cell/day to about 85 nU/cell/day, about 50 nU/cell/day to about 80 nU/cell/day, about 50 nU/cell/day to about 75 nU/cell/day, about 50 nU/cell/day to about 70 nU/cell/day, about 50 nU/cell/day to about 65 nU/cell/day, about 50 nU/cell/day to about 60 nU/cell/day, about 50 nU/cell/day to about 55 nU/cell/day, about 55 nU/cell/day to about 150 nU/cell/day, about 55 nU/cell/day to about 140 nU/cell/day, about 55 nU/cell/day to about 130 nU/cell/day, about 55 nU/cell/day to about 120 nU/cell/day, about 55 nU/cell/day to about 110 nU/cell/day, about 55 nU/cell/day to about 100 nU/cell/day, about 55 nU/cell/day to about 95 nU/cell/day, about 55 nU/cell/day to about 90 nU/cell/day, about 55 nU/cell/day to about 85 nU/cell/day, about 55 nU/cell/day to about 80 nU/cell/day, about 55 nU/cell/day to about 75 nU/cell/day, about 55 nU/cell/day to about 70 nU/cell/day, about 55 nU/cell/day to about 65 nU/cell/day, about 55 nU/cell/day to about 60 nU/cell/day, about 60 nU/cell/day to about 150 nU/cell/day, about 60 nU/cell/day to about 140 nU/cell/day, about 60 nU/cell/day to about 130 nU/cell/day, about 60 nU/cell/day to about 120 nU/cell/day, about 60 nU/cell/day to about 110 nU/cell/day, about 60 nU/cell/day to about 100 nU/cell/day, about 60 nU/cell/day to about 95 nU/cell/day, about 60 nU/cell/day to about 90 nU/cell/day, about 60 nU/cell/day to about 85 nU/cell/day, about 60 nU/cell/day to about 80 nU/cell/day, about 60 nU/cell/day to about 75 nU/cell/day, about 60 nU/cell/day to about 70 nU/cell/day, about 60 nU/cell/day to about 65 nU/cell/day, about 65 nU/cell/day to about 150 nU/cell/day, about 65 nU/cell/day to about 140 nU/cell/day, about 65 nU/cell/day to about 130 nU/cell/day, about 65 nU/cell/day to about 120 nU/cell/day, about 65 nU/cell/day to about 110 nU/cell/day, about 65 nU/cell/day to about 100 nU/cell/day, about 65 nU/cell/day to about 95 nU/cell/day, about 65 nU/cell/day to about 90 nU/cell/day, about 65 nU/cell/day to about 85 nU/cell/day, about 65 nU/cell/day to about 80 nU/cell/day, about 65 nU/cell/day to about 75 nU/cell/day, about 65 nU/cell/day to about 70 nU/cell/day, about 70 nU/cell/day to about 150 nU/cell/day, about 70 nU/cell/day to about 140 nU/cell/day, about 70 nU/cell/day to about 130 nU/cell/day, about 70 nU/cell/day to about 120 nU/cell/day, about 70 nU/cell/day to about 110 nU/cell/day, about 70 nU/cell/day to about 100 nU/cell/day, about 70 nU/cell/day to about 95 nU/cell/day, about 70 nU/cell/day to about 90 nU/cell/day, about 70 nU/cell/day to about 85 nU/cell/day, about 70 nU/cell/day to about 80 nU/cell/day, about 70 nU/cell/day to about 75 nU/cell/day, about 75 nU/cell/day to about 150 nU/cell/day, about 75 nU/cell/day to about 140 nU/cell/day, about 75 nU/cell/day to about 130 nU/cell/day, about 75 nU/cell/day to about 120 nU/cell/day, about 75 nU/cell/day to about 110 nU/cell/day, about 75 nU/cell/day to about 100 nU/cell/day, about 75 nU/cell/day to about 95 nU/cell/day, about 75 nU/cell/day to about 90 nU/cell/day, about 75 nU/cell/day to about 85 nU/cell/day, about 75 nU/cell/day to about 80 nU/cell/day, about 80 nU/cell/day to about 150 nU/cell/day, about 80 nU/cell/day to about 140 nU/cell/day, about 80 nU/cell/day to about 130 nU/cell/day, about 80 nU/cell/day to about 120 nU/cell/day, about 80 nU/cell/day to about 110 nU/cell/day, about 80 nU/cell/day to about 100 nU/cell/day, about 80 nU/cell/day to about 95 nU/cell/day, about 80 nU/cell/day to about 90 nU/cell/day, about 80 nU/cell/day to about 85 nU/cell/day, about 85 nU/cell/day to about 150 nU/cell/day, about 85 nU/cell/day to about 140 nU/cell/day, about 85 nU/cell/day to about 130 nU/cell/day, about 85 nU/cell/day to about 120 nU/cell/day, about 85 nU/cell/day to about 110 nU/cell/day, about 85 nU/cell/day to about 100 nU/cell/day, about 85 nU/cell/day to about 95 nU/cell/day, about 85 nU/cell/day to about 90 nU/cell/day, about 90 nU/cell/day to about 150 nU/cell/day, about 90 nU/cell/day to about 140 nU/cell/day, about 90 nU/cell/day to about 130 nU/cell/day, about 90 nU/cell/day to about 120 nU/cell/day, about 90 nU/cell/day to about 110 nU/cell/day, about 90 nU/cell/day to about 100 nU/cell/day, about 90 nU/cell/day to about 95 nU/cell/day, about 95 nU/cell/day to about 150 nU/cell/day, about 95 nU/cell/day to about 140 nU/cell/day, about 95 nU/cell/day to about 130 nU/cell/day, about 95 nU/cell/day to about 120 nU/cell/day, about 95 nU/cell/day to about 110 nU/cell/day, about 95 nU/cell/day to about 100 nU/cell/day, about 100 nU/cell/day to about 150 nU/cell/day, about 100 nU/cell/day to about 140 nU/cell/day, about 100 nU/cell/day to about 130 nU/cell/day, about 100 nU/cell/day to about 120 nU/cell/day, about 100 nU/cell/day to about 110 nU/cell/day, about 110 nU/cell/day to about 150 nU/cell/day, about 110 nU/cell/day to about 140 nU/cell/day, about 110 nU/cell/day to about 130 nU/cell/day, about 110 nU/cell/day to about 120 nU/cell/day, about 120 nU/cell/day to about 150 nU/cell/day, about 120 nU/cell/day to about 140 nU/cell/day, about 120 nU/cell/day to about 130 nU/cell/day, about 130 nU/cell/day to about 150 nU/cell/day, about 130 nU/cell/day to about 140 nU/cell/day, or about 140 nU/cell/day to about 150 nU/cell/day, during the culturing of the cell in the production bioreactor.

The growth rate is the compound growth calculation, which can be determined using the equation below.

Final cell density=Initial density$\times e^{kt}$, where k is the growth constant and t is the time in days.

The apparent growth rate is the sum of the calculated death rate added to the growth rate.

Some embodiments of any of the methods described herein further include culturing a cell (e.g., any of the cells described herein) in the production bioreactor (e.g., any of the production bioreactors described herein) using a concentration of the sensitizer predicted to result in an apparent growth rate of greater than 1% per day, greater than 1.5% per day, greater than 2% per day, greater than 2.5% per day, greater than 3% per day, greater than 3.5% per day, greater than 4.0% per day, greater than 4.5% per day, greater than 5.0% per day, greater than 5.5% per day, greater than 6.0% per day, greater than 6.5% per day, greater than 7.0% per day, greater than 7.5% per day, greater than 8.0% per day, greater than 8.5% per day, greater than 9.0% per day, greater than 9.5% per day, greater than 10.0% per day, greater than 10.5% per day, greater than 11.0% per day, greater than 11.5% per day, greater than 12.0% per day, greater than 12.5% per day, greater than 13.0% per day, greater than 13.5% per day, greater than 14.0% per day, greater than 14.5% per day, greater than 15.0% per day, greater than 16% per day, greater than 17% per day, greater than 18% per day, greater than 19% per day, greater than 20% per day, greater than 21% per day, greater than 22% per day, greater than 23% per day, greater than 24% per day, greater than 25% per day, greater than 30% per day, greater than 35% per day, greater than 40% per day, greater than 45% per day, greater than 50% per day, greater than 55% per day, greater than 60% per day, greater than 65% per day, greater than 70% per day, greater than 75% per day, greater than 80% per day, greater than 85% per day, greater than 90% per day, greater than 95% per day, greater than 100% per day, greater than 105% per day, greater than 110% per day, greater than 115% per day, greater than 120% per day, greater than 125% per day, greater than 130% per day, greater than 135% per day, greater than 140% per day, greater than 145% per day, or greater than 150% per day, during the culturing of the cell in the production bioreactor. Some embodiments of any of the methods described herein further include culturing a cell (e.g., any of the cells described herein) in the production bioreactor (e.g., any of the production bioreactors described herein) using a concentration of the sensitizer predicted to result in an apparent growth rate of about 0.1% per day to about 150% per day, about 0.1% per day to about 140% per day, about 0.1% per day to about 135% per day, about 0.1% per day to about 130% per day, about 0.1% per day to about 125% per day, about 0.1% per day to about 120% per day, about 0.1% per day to about 115% per day, about 0.1% per day to about 110% per day, about 0.1% per day to about 105% per day, about 0.1% per day to about 100% per day, about 0.1% per day to about 95% per day, about 0.1% per day to about 90% per day, about 0.1% per day to about 85% per day, about 0.1% per day to about 80% per day, about 0.1% per day to about 75% per day, about 0.1% to about 70% per day, about 0.1% per day to about 65% per day, about 0.1% per day to about 60% per day, about 0.1% per day to about 55% per day, about 0.1% per day to about 50% per day, about 0.1% per day to about 45% per day, about 0.1% per day to about 40% per day, about 0.1% per day to about 35% per day, about 0.1% per day to about 30% per day, about 0.1% to about 25% per day, about 0.1% per day to about 20% per day, about 0.1% per day to about 18% per day, about 0.1% per day to about 16% per day, about 0.1% to about 14% per day, about 0.1% per day to about 12% per day, about 0.1% per day to about 10% per day, about 0.1% per day to about 9.0% per day, about 0.1% per day to about 8.0% per day, about 0.1% per day to about 7.0% per day, about 0.1% per day to about 6.0% per day, about 0.1% per day to about 5.0% per day, about 0.1% per day to about 4.5% per day, about 0.1% per day to about 4.0% per day, about 0.1% per day to about 3.5% per day, about 0.1% per day to about 3.0% per day, about 0.1% per day to about 2.5% per day, about 0.1% per day to about 2.0% per day, about 0.1% per day to about 1.5% per day, about 0.1% per day to about 1.0% per day, about 0.1% per day to about 0.5% per day, about 0.5% per day to about 140% per day, about 0.5% per day to about 135% per day, about 0.5% per day to about 130% per day, about 0.5% per day to about 125% per day, about 0.5% per day to about 120% per day, about 0.5% per day to about 115% per day, about 0.5% per day to about 110% per day, about 0.5% per day to about 105% per day, about 0.5% per day to about 100% per day, about 0.5% per day to about 95% per day, about 0.5% per day to about 90% per day, about 0.5% per day to about 85% per day, about 0.5% per day to about 80% per day, about 0.5% per day to about 75% per day, about 0.5% to about 70% per day, about 0.5% per day to about 65% per day, about 0.5% per day to about 60% per day, about 0.5% per day to about 55% per day, about 0.5% per day to about 50% per day, about 0.5% per day to about 45% per day, about 0.5% per day to about 40% per day, about 0.5% per day to about 35% per day, about 0.5% per day to about 30% per day, about 0.5% to about 25% per day, about 0.5% per day to about 20% per day, about 0.5% per day to about 18% per day, about 0.5% per day to about 16% per day, about 0.5% to about 14% per day, about 0.5% per day to about 12% per day, about 0.5% per day to about 10% per day, about 0.5% per day to about 9.0% per day, about 0.5% per day to about 8.0% per day, about 0.5% per day to about 7.0% per day, about 0.5% per day to about 6.0% per day, about 0.5% per day to about 5.0% per day, about 0.5% per day to about 4.5% per day, about 0.5% per day to about 4.0% per day, about 0.5% per day to about 3.5% per day, about 0.5% per day to about 3.0% per day, about 0.5% per day to about 2.5% per day, about 0.5% per day to about 2.0% per day, about 0.5% per day to about 1.5% per day, about 0.5% per day to about 1.0% per day, about 1.0% per day to about 140% per day, about 1.0% per day to about 135% per day, about 1.0% per day to about 130% per day, about 1.0% per day to about 125% per day, about 1.0% per day to about 120% per day, about 1.0% per day to about 115% per day, about 1.0% per day to about 110% per day, about 1.0% per day to about 105% per day, about 1.0% per day to about 100% per day, about 1.0% per day to about 95% per day, about 1.0% per day to about 90% per day, about 1.0% per day to about 85% per day, about 1.0% per day to about 80% per day, about 1.0% per day to about 75% per day, about 1.0% to about 70% per day, about 1.0% per day to about 65% per day, about 1.0% per day to about 60% per day, about 1.0% per day to about 55% per day, about 1.0% per day to about 50% per day, about 1.0% per day to about 45% per day, about 1.0% per day to about 40% per day, about 1.0% per day to about 35% per day, about 1.0% per day to about 30% per day, about 1.0% to about 25% per day, about 1.0% per day to about 20% per day, about 1.0% per day to about 18% per day, about 1.0% per day to about 16% per day, about 1.0% to about 14% per day, about 1.0% per day to about 12% per day, about 1.0% per day to about 10% per day, about 1.0% per day to about 9.0% per day, about 1.0% per day to about 8.0% per day, about 1.0% per day to about 7.0% per day, about 1.0% per day to about 6.0% per day, about 1.0% per day to about 5.0% per day, about 1.0% per day to about 4.5% per day, about 1.0% per day to about 4.0% per day, about 1.0% per day to about 3.5% per day, about 1.0% per day to about 3.0% per day, about 1.0% per day to about 2.5% per day, about 1.0% per day to about 2.0% per day, about 1.0% per day to about 1.5% per day, about 1.5% per day to about 140% per day, about 1.5% per day to about 135% per day, about 1.5% per day to about 130% per day, about 1.5% per day to about 125% per day, about 1.5% per day to about 120% per day, about 1.5% per day to about 115% per day, about 1.5% per day to about 110% per day, about 1.5% per day to about 105% per day, about 1.5% per day to about 100% per day, about 1.5% per day to about 95% per day, about 1.5% per day to about 90% per day, about 1.5% per day to about 85% per day, about 1.5% per day to about 80% per day, about 1.5% per day to about 75% per day, about 1.5% to about 70% per day, about 1.5% per day to about 65% per day, about 1.5% per day to about 60% per day, about 1.5% per day to about 55% per day, about 1.5% per day to about 50% per day, about 1.5% per day to about 45% per day, about 1.5% per day to about 40% per day, about 1.5% per day to about 35% per day, about 1.5% per day to about 30% per day, about 1.5% to about 25% per day, about 1.5% per day to about 20% per day, about 1.5% per day to about 18% per day, about 1.5% per day to about 16% per day, about 1.5% to about 14% per day, about 1.5% per day to about 12% per day, about 1.5% per day to about 10% per day, about 1.5% per day to about 9.0% per day, about 1.5% per day to about 8.0% per day, about 1.5% per day to about 7.0% per day, about 1.5% per day to about 6.0% per day, about 1.5% per day to about 5.0% per day, about 1.5% per day to about 4.5% per day, about 1.5% per day to about 4.0% per day, about 1.5% per day to about 3.5% per day, about 1.5% per day to about 3.0% per day, about 1.5% per day to about 2.5% per day, about 1.5% per day to about 2.0% per day, about 2.0% per day to about 140% per day, about 2.0% per day to about 135% per day, about 2.0% per day to about 130% per day, about 2.0% per day to about 125% per day, about 2.0% per day to about 120% per day, about 2.0% per day to about 115% per day, about 2.0% per day to about 110% per day, about 2.0% per day to about 105% per day, about 2.0% per day to about 100% per day, about 2.0% per day to about 95% per day, about 2.0% per day to about 90% per day, about 2.0% per day to about 85% per day, about 2.0% per day to about 80% per day, about 2.0% per day to about 75% per day, about 2.0% to about 70% per day, about 2.0% per day to about 65% per day, about 2.0% per day to about 60% per day, about 2.0% per day to about 55% per day, about 2.0% per day to about 50% per day, about 2.0% per day to about 45% per day, about 2.0% per day to about 40% per day, about 2.0% per day to about 35% per day, about 2.0% per day to about 30% per day, about 2.0% to about 25% per day, about 2.0% per day to about 20% per day, about 2.0% per day to about 18% per day, about 2.0% per day to about 16% per day, about 2.0% to about 14% per day, about 2.0% per day to about 12% per day, about 2.0% per day to about 10% per day, about 2.0% per day to about 9.0% per day, about 2.0% per day to about 8.0% per day, about 2.0% per day to about 7.0% per day, about 2.0% per day to about 6.0% per day, about 2.0% per day to about 5.0% per day, about 2.0% per day to about 4.5% per day, about 2.0% per day to about 4.0% per day, about 2.0% per day to about 3.5% per day, about 2.0% per day to about 3.0% per day, about 2.0% per day to about 2.5% per day, about 2.5% per day to about 140% per day, about 2.5% per day to about 135% per day, about 2.5% per day to about 130% per day, about 2.5% per day to about 125% per day, about 2.5% per day to about 120% per day, about 2.5% per day to about 115% per day, about 2.5% per day to about 110% per day, about 2.5% per day to about 105% per day, about 2.5% per day to about 100% per day, about 2.5% per day to about 95% per day, about 2.5% per day to about 90% per day, about 2.5% per day to about 85% per day, about 2.5% per day to about 80% per day, about 2.5% per day to about 75% per day, about 2.5% to about 70% per day, about 2.5% per day to about 65% per day, about 2.5% per day to about 60% per day, about 2.5% per day to about 55% per day, about 2.5% per day to about 50% per day, about 2.5% per day to about 45% per day, about 2.5% per day to about 40% per day, about 2.5% per day to about 35% per day, about 2.5% per day to about 30% per day, about 2.5% to about 25% per day, about 2.5% per day to about 20% per day, about 2.5% per day to about 18% per day, about 2.5% per day to about 16% per day, about 2.5% to about 14% per day, about 2.5% per day to about 12% per day, about 2.5% per day to about 10% per day, about 2.5% per day to about 9.0% per day, about 2.5% per day to about 8.0% per day, about 2.5% per day to about 7.0% per day, about 2.5% per day to about 6.0% per day, about 2.5% per day to about 5.0% per day, about 2.5% per day to about 4.5% per day, about 2.5% per day to about 4.0% per day, about 2.5% per day to about 3.5% per day, about 2.5% per day to about 3.0% per day, about 3.0% per day to about 140% per day, about 3.0% per day to about 135% per day, about 3.0% per day to about 130% per day, about 3.0% per day to about 125% per day, about 3.0% per day to about 120% per day, about 3.0% per day to about 115% per day, about 3.0% per day to about 110% per day, about 3.0% per day to about 105% per day, about 3.0% per day to about 100% per day, about 3.0% per day to about 95% per day, about 3.0% per day to about 90% per day, about 3.0% per day to about 85% per day, about 3.0% per day to about 80% per day, about 3.0% per day to about 75% per day, about 3.0% to about 70% per day, about 3.0% per day to about 65% per day, about 3.0% per day to about 60% per day, about 3.0% per day to about 55% per day, about 3.0% per day to about 50% per day, about 3.0% per day to about 45% per day, about 3.0% per day to about 40% per day, about 3.0% per day to about 35% per day, about 3.0% per day to about 30% per day, about 3.0% to about 25% per day, about 3.0% per day to about 20% per day, about 3.0% per day to about 18% per day, about 3.0% per day to about 16% per day, about 3.0% to about 14% per day, about 3.0% per day to about 12% per day, about 3.0% per day to about 10% per day, about 3.0% per day to about 9.0% per day, about 3.0% per day to about 8.0% per day, about 3.0% per day to about 7.0% per day, about 3.0% per day to about 6.0% per day, about 3.0% per day to about 5.0% per day, about 3.0% per day to about 4.5% per day, about 3.0% per day to about 4.0% per day, about 3.0% per day to about 3.5% per day, about 3.5% per day to about 140% per day, about 3.5% per day to about 135% per day, about 3.5% per day to about 130% per day, about 3.5% per day to about 125% per day, about 3.5% per day to about 120% per day, about 3.5% per day to about 115% per day, about 3.5% per day to about 110% per day, about 3.5% per day to about 105% per day, about 3.5% per day to about 100% per day, about 3.5% per day to about 95% per day, about 3.5% per day to about 90% per day, about 3.5% per day to about 85% per day, about 3.5% per day to about 80% per day, about 3.5% per day to about 75% per day, about 3.5% to about 70% per day, about 3.5% per day to about 65% per day, about 3.5% per day to about 60% per day, about 3.5% per day to about 55% per day, about 3.5% per day to about 50% per day, about 3.5% per day to about 45% per day, about 3.5% per day to about 40% per day, about 3.5% per day to about 35% per day, about 3.5% per day to about 30% per day, about 3.5% to about 25% per day, about 3.5% per day to about 20% per day, about 3.5% per day to about 18% per day, about 3.5% per day to about 16% per day, about 3.5% to about 14% per day, about 3.5% per day to about 12% per day, about 3.5% per day to about 10% per day, about 3.5% per day to about 9.0% per day, about 3.5% per day to about 8.0% per day, about 3.5% per day to about 7.0% per day, about 3.5% per day to about 6.0% per day, about 3.5% per day to about 5.0% per day, about 3.5% per day to about 4.5% per day, about 3.5% per day to about 4.0% per day, about 4.0% per day to about 140% per day, about 4.0% per day to about 135% per day, about 4.0% per day to about 130% per day, about 4.0% per day to about 125% per day, about 4.0% per day to about 120% per day, about 4.0% per day to about 115% per day, about 4.0% per day to about 110% per day, about 4.0% per day to about 105% per day, about 4.0% per day to about 100% per day, about 4.0% per day to about 95% per day, about 4.0% per day to about 90% per day, about 4.0% per day to about 85% per day, about 4.0% per day to about 80% per day, about 4.0% per day to about 75% per day, about 4.0% to about 70% per day, about 4.0% per day to about 65% per day, about 4.0% per day to about 60% per day, about 4.0% per day to about 55% per day, about 4.0% per day to about 50% per day, about 4.0% per day to about 45% per day, about 4.0% per day to about 40% per day, about 4.0% per day to about 35% per day, about 4.0% per day to about 30% per day, about 4.0% to about 25% per day, about 4.0% per day to about 20% per day, about 4.0% per day to about 18% per day, about 4.0% per day to about 16% per day, about 4.0% to about 14% per day, about 4.0% per day to about 12% per day, about 4.0% per day to about 10% per day, about 4.0% per day to about 9.0% per day, about 4.0% per day to about 8.0% per day, about 4.0% per day to about 7.0% per day, about 4.0% per day to about 6.0% per day, about 4.0% per day to about 5.0% per day, about 4.0% per day to about 4.5% per day, about 4.5% per day to about 140% per day, about 4.5% per day to about 135% per day, about 4.5% per day to about 130% per day, about 4.5% per day to about 125% per day, about 4.5% per day to about 120% per day, about 4.5% per day to about 115% per day, about 4.5% per day to about 110% per day, about 4.5% per day to about 105% per day, about 4.5% per day to about 100% per day, about 4.5% per day to about 95% per day, about 4.5% per day to about 90% per day, about 4.5% per day to about 85% per day, about 4.5% per day to about 80% per day, about 4.5% per day to about 75% per day, about 4.5% to about 70% per day, about 4.5% per day to about 65% per day, about 4.5% per day to about 60% per day, about 4.5% per day to about 55% per day, about 4.5% per day to about 50% per day, about 4.5% per day to about 45% per day, about 4.5% per day to about 40% per day, about 4.5% per day to about 35% per day, about 4.5% per day to about 30% per day, about 4.5% to about 25% per day, about 4.5% per day to about 20% per day, about 4.5% per day to about 18% per day, about 4.5% per day to about 16% per day, about 4.5% to about 14% per day, about 4.5% per day to about 12% per day, about 4.5% per day to about 10% per day, about 4.5% per day to about 9.0% per day, about 4.5% per day to about 8.0% per day, about 4.5% per day to about 7.0% per day, about 4.5% per day to about 6.0% per day, about 4.5% per day to about 5.0% per day, about 5.0% per day to about 140% per day, about 5.0% per day to about 135% per day, about 5.0% per day to about 130% per day, about 5.0% per day to about 125% per day, about 5.0% per day to about 120% per day, about 5.0% per day to about 115% per day, about 5.0% per day to about 110% per day, about 5.0% per day to about 105% per day, about 5.0% per day to about 100% per day, about 5.0% per day to about 95% per day, about 5.0% per day to about 90% per day, about 5.0% per day to about 85% per day, about 5.0% per day to about 80% per day, about 5.0% per day to about 75% per day, about 5.0% to about 70% per day, about 5.0% per day to about 65% per day, about 5.0% per day to about 60% per day, about 5.0% per day to about 55% per day, about 5.0% per day to about 50% per day, about 5.0% per day to about 45% per day, about 5.0% per day to about 40% per day, about 5.0% per day to about 35% per day, about 5.0% per day to about 30% per day, about 5.0% to about 25% per day, about 5.0% per day to about 20% per day, about 5.0% per day to about 18% per day, about 5.0% per day to about 16% per day, about 5.0% to about 14% per day, about 5.0% per day to about 12% per day, about 5.0% per day to about 10% per day, about 5.0% per day to about 9.0% per day, about 5.0% per day to about 8.0% per day, about 5.0% per day to about 7.0% per day, about 5.0% per day to about 6.0% per day, about 6.0% per day to about 140% per day, about 6.0% per day to about 135% per day, about 6.0% per day to about 130% per day, about 6.0% per day to about 125% per day, about 6.0% per day to about 120% per day, about 6.0% per day to about 115% per day, about 6.0% per day to about 110% per day, about 6.0% per day to about 105% per day, about 6.0% per day to about 100% per day, about 6.0% per day to about 95% per day, about 6.0% per day to about 90% per day, about 6.0% per day to about 85% per day, about 6.0% per day to about 80% per day, about 6.0% per day to about 75% per day, about 6.0% to about 70% per day, about 6.0% per day to about 65% per day, about 6.0% per day to about 60% per day, about 6.0% per day to about 55% per day, about 6.0% per day to about 50% per day, about 6.0% per day to about 45% per day, about 6.0% per day to about 40% per day, about 6.0% per day to about 35% per day, about 6.0% per day to about 30% per day, about 6.0% to about 25% per day, about 6.0% per day to about 20% per day, about 6.0% per day to about 18% per day, about 6.0% per day to about 16% per day, about 6.0% to about 14% per day, about 6.0% per day to about 12% per day, about 6.0% per day to about 10% per day, about 6.0% per day to about 9.0% per day, about 6.0% per day to about 8.0% per day, about 6.0% per day to about 7.0% per day, about 7.0% per day to about 140% per day, about 7.0% per day to about 135% per day, about 7.0% per day to about 130% per day, about 7.0% per day to about 125% per day, about 7.0% per day to about 120% per day, about 7.0% per day to about 115% per day, about 7.0% per day to about 110% per day, about 7.0% per day to about 105% per day, about 7.0% per day to about 100% per day, about 7.0% per day to about 95% per day, about 7.0% per day to about 90% per day, about 7.0% per day to about 85% per day, about 7.0% per day to about 80% per day, about 7.0% per day to about 75% per day, about 7.0% to about 70% per day, about 7.0% per day to about 65% per day, about 7.0% per day to about 60% per day, about 7.0% per day to about 55% per day, about 7.0% per day to about 50% per day, about 7.0% per day to about 45% per day, about 7.0% per day to about 40% per day, about 7.0% per day to about 35% per day, about 7.0% per day to about 30% per day, about 7.0% to about 25% per day, about 7.0% per day to about 20% per day, about 7.0% per day to about 18% per day, about 7.0% per day to about 16% per day, about 7.0% to about 14% per day, about 7.0% per day to about 12% per day, about 7.0% per day to about 10% per day, about 7.0% per day to about 9.0% per day, about 7.0% per day to about 8.0% per day, about 8.0% per day to about 140% per day, about 8.0% per day to about 135% per day, about 8.0% per day to about 130% per day, about 8.0% per day to about 125% per day, about 8.0% per day to about 120% per day, about 8.0% per day to about 115% per day, about 8.0% per day to about 110% per day, about 8.0% per day to about 105% per day, about 8.0% per day to about 100% per day, about 8.0% per day to about 95% per day, about 8.0% per day to about 90% per day, about 8.0% per day to about 85% per day, about 8.0% per day to about 80% per day, about 8.0% per day to about 75% per day, about 8.0% to about 70% per day, about 8.0% per day to about 65% per day, about 8.0% per day to about 60% per day, about 8.0% per day to about 55% per day, about 8.0% per day to about 50% per day, about 8.0% per day to about 45% per day, about 8.0% per day to about 40% per day, about 8.0% per day to about 35% per day, about 8.0% per day to about 30% per day, about 8.0% to about 25% per day, about 8.0% per day to about 20% per day, about 8.0% per day to about 18% per day, about 8.0% per day to about 16% per day, about 8.0% to about 14% per day, about 8.0% per day to about 12% per day, about 8.0% per day to about 10% per day, about 8.0% per day to about 9.0% per day, about 9.0% per day to about 140% per day, about 9.0% per day to about 135% per day, about 9.0% per day to about 130% per day, about 9.0% per day to about 125% per day, about 9.0% per day to about 120% per day, about 9.0% per day to about 115% per day, about 9.0% per day to about 110% per day, about 9.0% per day to about 105% per day, about 9.0% per day to about 100% per day, about 9.0% per day to about 95% per day, about 9.0% per day to about 90% per day, about 9.0% per day to about 85% per day, about 9.0% per day to about 80% per day, about 9.0% per day to about 75% per day, about 9.0% to about 70% per day, about 9.0% per day to about 65% per day, about 9.0% per day to about 60% per day, about 9.0% per day to about 55% per day, about 9.0% per day to about 50% per day, about 9.0% per day to about 45% per day, about 9.0% per day to about 40% per day, about 9.0% per day to about 35% per day, about 9.0% per day to about 30% per day, about 9.0% to about 25% per day, about 9.0% per day to about 20% per day, about 9.0% per day to about 18% per day, about 9.0% per day to about 16% per day, about 9.0% to about 14% per day, about 9.0% per day to about 12% per day, about 9.0% per day to about 10% per day, about 10% per day to about 140% per day, about 10% per day to about 135% per day, about 10% per day to about 130% per day, about 10% per day to about 125% per day, about 10% per day to about 120% per day, about 10% per day to about 115% per day, about 10% per day to about 110% per day, about 10% per day to about 105% per day, about 10% per day to about 100% per day, about 10% per day to about 95% per day, about 10% per day to about 90% per day, about 10% per day to about 85% per day, about 10% per day to about 80% per day, about 10% per day to about 75% per day, about 10% to about 70% per day, about 10% per day to about 65% per day, about 10% per day to about 60% per day, about 10% per day to about 55% per day, about 10% per day to about 50% per day, about 10% per day to about 45% per day, about 10% per day to about 40% per day, about 10% per day to about 35% per day, about 10% per day to about 30% per day, about 10% to about 25% per day, about 10% per day to about 20% per day, about 10% per day to about 18% per day, about 10% per day to about 16% per day, about 10% to about 14% per day, about 10% per day to about 12% per day, about 12% per day to about 140% per day, about 12% per day to about 135% per day, about 12% per day to about 130% per day, about 12% per day to about 125% per day, about 12% per day to about 120% per day, about 12% per day to about 115% per day, about 12% per day to about 110% per day, about 12% per day to about 105% per day, about 12% per day to about 100% per day, about 12% per day to about 95% per day, about 12% per day to about 90% per day, about 12% per day to about 85% per day, about 12% per day to about 80% per day, about 12% per day to about 75% per day, about 12% to about 70% per day, about 12% per day to about 65% per day, about 12% per day to about 60% per day, about 12% per day to about 55% per day, about 12% per day to about 50% per day, about 12% per day to about 45% per day, about 12% per day to about 40% per day, about 12% per day to about 35% per day, about 12% per day to about 30% per day, about 12% to about 25% per day, about 12% per day to about 20% per day, about 12% per day to about 18% per day, about 12% per day to about 16% per day, about 12% to about 14% per day, about 14% per day to about 140% per day, about 14% per day to about 135% per day, about 14% per day to about 130% per day, about 14% per day to about 125% per day, about 14% per day to about 120% per day, about 14% per day to about 115% per day, about 14% per day to about 110% per day, about 14% per day to about 105% per day, about 14% per day to about 100% per day, about 14% per day to about 95% per day, about 14% per day to about 90% per day, about 14% per day to about 85% per day, about 14% per day to about 80% per day, about 14% per day to about 75% per day, about 14% to about 70% per day, about 14% per day to about 65% per day, about 14% per day to about 60% per day, about 14% per day to about 55% per day, about 14% per day to about 50% per day, about 14% per day to about 45% per day, about 14% per day to about 40% per day, about 14% per day to about 35% per day, about 14% per day to about 30% per day, about 14% to about 25% per day, about 14% per day to about 20% per day, about 14% per day to about 18% per day, about 14% per day to about 16% per day, about 16% per day to about 140% per day, about 16% per day to about 135% per day, about 16% per day to about 130% per day, about 16% per day to about 125% per day, about 16% per day to about 120% per day, about 16% per day to about 115% per day, about 16% per day to about 110% per day, about 16% per day to about 105% per day, about 16% per day to about 100% per day, about 16% per day to about 95% per day, about 16% per day to about 90% per day, about 16% per day to about 85% per day, about 16% per day to about 80% per day, about 16% per day to about 75% per day, about 16% to about 70% per day, about 16% per day to about 65% per day, about 16% per day to about 60% per day, about 16% per day to about 55% per day, about 16% per day to about 50% per day, about 16% per day to about 45% per day, about 16% per day to about 40% per day, about 16% per day to about 35% per day, about 16% per day to about 30% per day, about 16% to about 25% per day, about 16% per day to about 20% per day, about 16% per day to about 18% per day, about 18% per day to about 140% per day, about 18% per day to about 135% per day, about 18% per day to about 130% per day, about 18% per day to about 125% per day, about 18% per day to about 120% per day, about 18% per day to about 115% per day, about 18% per day to about 110% per day, about 18% per day to about 105% per day, about 18% per day to about 100% per day, about 18% per day to about 95% per day, about 18% per day to about 90% per day, about 18% per day to about 85% per day, about 18% per day to about 80% per day, about 18% per day to about 75% per day, about 18% to about 70% per day, about 18% per day to about 65% per day, about 18% per day to about 60% per day, about 18% per day to about 55% per day, about 18% per day to about 50% per day, about 18% per day to about 45% per day, about 18% per day to about 40% per day, about 18% per day to about 35% per day, about 18% per day to about 30% per day, about 18% to about 25% per day, about 18% per day to about 20% per day, about 20% per day to about 140% per day, about 20% per day to about 135% per day, about 20% per day to about 130% per day, about 20% per day to about 125% per day, about 20% per day to about 120% per day, about 20% per day to about 115% per day, about 20% per day to about 110% per day, about 20% per day to about 105% per day, about 20% per day to about 100% per day, about 20% per day to about 95% per day, about 20% per day to about 90% per day, about 20% per day to about 85% per day, about 20% per day to about 80% per day, about 20% per day to about 75% per day, about 20% to about 70% per day, about 20% per day to about 65% per day, about 20% per day to about 60% per day, about 20% per day to about 55% per day, about 20% per day to about 50% per day, about 20% per day to about 45% per day, about 20% per day to about 40% per day, about 20% per day to about 35% per day, about 20% per day to about 30% per day, about 20% to about 25% per day, about 25% per day to about 140% per day, about 25% per day to about 135% per day, about 25% per day to about 130% per day, about 25% per day to about 125% per day, about 25% per day to about 120% per day, about 25% per day to about 115% per day, about 25% per day to about 110% per day, about 25% per day to about 105% per day, about 25% per day to about 100% per day, about 25% per day to about 95% per day, about 25% per day to about 90% per day, about 25% per day to about 85% per day, about 25% per day to about 80% per day, about 25% per day to about 75% per day, about 25% to about 70% per day, about 25% per day to about 65% per day, about 25% per day to about 60% per day, about 25% per day to about 55% per day, about 25% per day to about 50% per day, about 25% per day to about 45% per day, about 25% per day to about 40% per day, about 25% per day to about 35% per day, about 25% per day to about 30% per day, about 30% per day to about 140% per day, about 30% per day to about 135% per day, about 30% per day to about 130% per day, about 30% per day to about 125% per day, about 30% per day to about 120% per day, about 30% per day to about 115% per day, about 30% per day to about 110% per day, about 30% per day to about 105% per day, about 30% per day to about 100% per day, about 30% per day to about 95% per day, about 30% per day to about 90% per day, about 30% per day to about 85% per day, about 30% per day to about 80% per day, about 30% per day to about 75% per day, about 30% to about 70% per day, about 30% per day to about 65% per day, about 30% per day to about 60% per day, about 30% per day to about 55% per day, about 30% per day to about 50% per day, about 30% per day to about 45% per day, about 30% per day to about 40% per day, about 30% per day to about 35% per day, about 35% per day to about 140% per day, about 35% per day to about 135% per day, about 35% per day to about 130% per day, about 35% per day to about 125% per day, about 35% per day to about 120% per day, about 35% per day to about 115% per day, about 35% per day to about 110% per day, about 35% per day to about 105% per day, about 35% per day to about 100% per day, about 35% per day to about 95% per day, about 35% per day to about 90% per day, about 35% per day to about 85% per day, about 35% per day to about 80% per day, about 35% per day to about 75% per day, about 35% to about 70% per day, about 35% per day to about 65% per day, about 35% per day to about 60% per day, about 35% per day to about 55% per day, about 35% per day to about 50% per day, about 35% per day to about 45% per day, about 35% per day to about 40% per day, about 40% per day to about 140% per day, about 40% per day to about 135% per day, about 40% per day to about 130% per day, about 40% per day to about 125% per day, about 40% per day to about 120% per day, about 40% per day to about 115% per day, about 40% per day to about 110% per day, about 40% per day to about 105% per day, about 40% per day to about 100% per day, about 40% per day to about 95% per day, about 40% per day to about 90% per day, about 40% per day to about 85% per day, about 40% per day to about 80% per day, about 40% per day to about 75% per day, about 40% to about 70% per day, about 40% per day to about 65% per day, about 40% per day to about 60% per day, about 40% per day to about 55% per day, about 40% per day to about 50% per day, about 40% per day to about 45% per day, about 45% per day to about 140% per day, about 45% per day to about 135% per day, about 45% per day to about 130% per day, about 45% per day to about 125% per day, about 45% per day to about 120% per day, about 45% per day to about 115% per day, about 45% per day to about 110% per day, about 45% per day to about 105% per day, about 45% per day to about 100% per day, about 45% per day to about 95% per day, about 45% per day to about 90% per day, about 45% per day to about 85% per day, about 45% per day to about 80% per day, about 45% per day to about 75% per day, about 45% to about 70% per day, about 45% per day to about 65% per day, about 45% per day to about 60% per day, about 45% per day to about 55% per day, about 45% per day to about 50% per day, about 50% per day to about 140% per day, about 50% per day to about 135% per day, about 50% per day to about 130% per day, about 50% per day to about 125% per day, about 50% per day to about 120% per day, about 50% per day to about 115% per day, about 50% per day to about 110% per day, about 50% per day to about 105% per day, about 50% per day to about 100% per day, about 50% per day to about 95% per day, about 50% per day to about 90% per day, about 50% per day to about 85% per day, about 50% per day to about 80% per day, about 50% per day to about 75% per day, about 50% to about 70% per day, about 50% per day to about 65% per day, about 50% per day to about 60% per day, about 50% per day to about 55% per day, about 55% per day to about 140% per day, about 55% per day to about 135% per day, about 55% per day to about 130% per day, about 55% per day to about 125% per day, about 55% per day to about 120% per day, about 55% per day to about 115% per day, about 55% per day to about 110% per day, about 55% per day to about 105% per day, about 55% per day to about 100% per day, about 55% per day to about 95% per day, about 55% per day to about 90% per day, about 55% per day to about 85% per day, about 55% per day to about 80% per day, about 55% per day to about 75% per day, about 55% to about 70% per day, about 55% per day to about 65% per day, about 55% per day to about 60% per day, about 60% per day to about 140% per day, about 60% per day to about 135% per day, about 60% per day to about 130% per day, about 60% per day to about 125% per day, about 60% per day to about 120% per day, about 60% per day to about 115% per day, about 650% per day to about 110% per day, about 60% per day to about 105% per day, about 60% per day to about 100% per day, about 60% per day to about 95% per day, about 60% per day to about 90% per day, about 60% per day to about 85% per day, about 60% per day to about 80% per day, about 60% per day to about 75% per day, about 60% to about 70% per day, about 60% per day to about 65% per day, about 65% per day to about 140% per day, about 65% per day to about 135% per day, about 65% per day to about 130% per day, about 65% per day to about 125% per day, about 65% per day to about 120% per day, about 65% per day to about 115% per day, about 65% per day to about 110% per day, about 65% per day to about 105% per day, about 65% per day to about 100% per day, about 65% per day to about 95% per day, about 65% per day to about 90% per day, about 65% per day to about 85% per day, about 65% per day to about 80% per day, about 65% per day to about 75% per day, about 65% to about 70% per day, about 70% per day to about 140% per day, about 70% per day to about 135% per day, about 70% per day to about 130% per day, about 70% per day to about 125% per day, about 70% per day to about 120% per day, about 70% per day to about 115% per day, about 70% per day to about 110% per day, about 70% per day to about 105% per day, about 70% per day to about 100% per day, about 70% per day to about 95% per day, about 70% per day to about 90% per day, about 70% per day to about 85% per day, about 70% per day to about 80% per day, about 70% per day to about 75% per day, about 75% per day to about 140% per day, about 75% per day to about 135% per day, about 75% per day to about 130% per day, about 75% per day to about 125% per day, about 75% per day to about 120% per day, about 75% per day to about 115% per day, about 75% per day to about 110% per day, about 75% per day to about 105% per day, about 75% per day to about 100% per day, about 75% per day to about 95% per day, about 75% per day to about 90% per day, about 75% per day to about 85% per day, about 75% per day to about 80% per day, about 80% per day to about 140% per day, about 80% per day to about 135% per day, about 80% per day to about 130% per day, about 80% per day to about 125% per day, about 80% per day to about 120% per day, about 80% per day to about 115% per day, about 80% per day to about 110% per day, about 80% per day to about 105% per day, about 80% per day to about 100% per day, about 80% per day to about 95% per day, about 80% per day to about 90% per day, about 80% per day to about 85% per day, about 85% per day to about 140% per day, about 85% per day to about 135% per day, about 85% per day to about 130% per day, about 85% per day to about 125% per day, about 85% per day to about 120% per day, about 85% per day to about 115% per day, about 85% per day to about 110% per day, about 85% per day to about 105% per day, about 85% per day to about 100% per day, about 85% per day to about 95% per day, about 85% per day to about 90% per day, about 90% per day to about 140% per day, about 90% per day to about 135% per day, about 90% per day to about 130% per day, about 90% per day to about 125% per day, about 90% per day to about 120% per day, about 90% per day to about 115% per day, about 90% per day to about 110% per day, about 90% per day to about 105% per day, about 90% per day to about 100% per day, about 90% per day to about 95% per day, about 95% per day to about 140% per day, about 95% per day to about 135% per day, about 95% per day to about 130% per day, about 95% per day to about 125% per day, about 95% per day to about 120% per day, about 95% per day to about 115% per day, about 95% per day to about 110% per day, about 95% per day to about 105% per day, about 95% per day to about 100% per day, about 100% per day to about 140% per day, about 100% per day to about 135% per day, about 100% per day to about 130% per day, about 100% per day to about 125% per day, about 100% per day to about 120% per day, about 100% per day to about 115% per day, about 100% per day to about 110% per day, about 100% per day to about 105% per day, about 105% per day to about 140% per day, about 105% per day to about 135% per day, about 105% per day to about 130% per day, about 105% per day to about 125% per day, about 105% per day to about 120% per day, about 105% per day to about 115% per day, about 105% per day to about 110% per day, about 110% per day to about 140% per day, about 110% per day to about 135% per day, about 110% per day to about 130% per day, about 110% per day to about 125% per day, about 110% per day to about 120% per day, about 110% per day to about 115% per day, about 115% per day to about 140% per day, about 115% per day to about 135% per day, about 115% per day to about 130% per day, about 115% per day to about 125% per day, about 115% per day to about 120% per day, about 120% per day to about 140% per day, about 120% per day to about 135% per day, about 120% per day to about 130% per day, about 120% per day to about 125% per day, about 125% per day to about 140% per day, about 125% per day to about 135% per day, about 125% per day to about 130% per day, about 130% per day to about 140% per day, about 130% per day to about 135% per day, or about 135% per day to about 140% per day, during the culturing of the cell in the production bioreactor.

In some embodiments of these methods, the cell contains a nucleic acid encoding a recombinant therapeutic protein. Some embodiments of these methods further include collecting or recovering the recombinant therapeutic protein. Some embodiments of these methods further include purifying the recombinant therapeutic protein. Some embodiments of these methods further include formulating the purified recombinant therapeutic protein.

In some embodiments of these methods, the cell is a bacterium (e.g., any of the exemplary bacteria described herein or known in the art), a yeast (e.g., any of the exemplary yeast cells described herein or known in the art), or a mammalian cell (e.g., any of the exemplary mammalian cells described herein or known in the art).

In some embodiments of these methods, the cell viability is determined by measuring a concentration of lactic acid dehydrogenase (LDH) in the test culture vessel.

In some embodiments, the test culture vessel is a baffled shake flask (e.g., any of the baffled shake flasks described herein or known in the art) and the plurality of test conditions include one or more of: (a) a rotary agitation of about 125 RPM to about 400 RPM (or any of the subranges of this range described herein); (b) a concentration of the sensitizer (e.g., any of the sensitizers described herein or known in the art) of about 0 ppm to about 120 ppm (or any of the subranges of this range described herein); and (c) a concentration of a protectant (e.g., any of the protectants described herein or known in the art) that is about 1 g/L to about 10 g/L (or any of the subranges of this range described herein). In some embodiments, the protectant is a poloxamer (e.g., poloxamer-188, poloxamer-401, poloxamer-402, or poloxamer-407), a poloxamine (e.g., poloxamine-904 or poloxamine-908), or a non-ionic surfactant Pluronic®.

Methods of Improving Cell Viability in a Production Bioreactor

Also provided herein are methods of improving cell viability in a production bioreactor (e.g., any of the production bioreactors described herein) that include: (a) determining cell viability under a plurality of test conditions in a test culture vessel, where the plurality of conditions are defined by a set of parameters; (b) based on the cell viability in the test culture vessel under the plurality of conditions, selecting a condition that is optimal for cell viability in a production bioreactor; and (c) culturing a cell in the production bioreactor under the selected condition.

In some embodiments of these methods, the set of parameter comprises, consists essentially of, or consists of shear stress, concentration of a sensitizer (e.g., any of the sensitizers described herein or known in the art), and concentration of a protectant (e.g., any of the protectants described herein or known in the art). In some embodiments of these methods, the plurality of testing conditions are selected based on full factorial screening and/or inscribed center composite design. In some embodiments of these methods, the sensitizer is an antifoam (e.g., a polydimethylsiloxane-based antifoam, simethicone, or any other antifoam described herein or known in the art).

In some embodiments of these methods, the test culture vessel (e.g., any of the test culture vessels described herein or known in the art) has a volume of about 5 mL to about 5 L (or any of the subranges of this range described herein). In some embodiments of these methods, the test culture vessel is a shake flask, e.g., a baffled shake flask (e.g., any of the baffled shake flasks described herein or known in the art).

In some embodiments of these methods, the production bioreactor (e.g., any of the production bioreactors described herein) has a volume of about 5 L to about 20,000 L (or any of the subranges of this range described herein). In some examples, the production bioreactor is a perfusion bioreactor. In other examples, the production bioreactor is a fed batch bioreactor.

In some embodiments, step (c) results in a specific cell death rate of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% per day, during the culturing of the cells in the production bioreactor. In some embodiments, step (c) results in a specific cell death rate of about 0.1% to about 40% per day (or any of the subranges of this range described herein) during the culturing of the cells in the production bioreactor.

In some embodiments, step (c) results in a cell specific LDH production of less than 150 nU/cell/day, less than 145 nU/cell/day, less than 140 nU/cell/day, less than 135 nU/cell/day, less than 130 nU/cell/day, less than 125 nU/cell/day, less than 120 nU/cell/day, less than 115 nU/cell/day, less than 150 nU/cell/day, less than 110 nU/cell/day, less than 105 nU/cell/day, less than 100 nU/cell/day, less than 95 nU/cell/day, less than 90 nU/cell/day, less than 85 nU/cell/day, less than 80 nU/cell/day, less than 75 nU/cell/day, less than 70 nU/cell/day, less than 65 nU/cell/day, less than 60 nU/cell/day, less than 55 nU/cell/day, less than 50 nU/cell/day, less than 45 nU/cell/day, less than 45 nU/cell/day, less than 40 nU/cell/day, less than 35 nU/cell/day, less than 30 nU/cell/day, less than 25 nU/cell/day, less than 20 nU/cell/day, less than 15 nU/cell/day, less than 10 nU/cell/day, less than 5 nU/cell/day, or less than less than 1 nU/cell/day, during the culturing of the cell in the production bioreactor. In some embodiments of these methods, step (c) results in a cell specific LDH production of about 0.1 nU/cell/day to about 150 nU/cell/day (or any of the subranges of this range described herein) during the culturing of the cell in the production bioreactor.

In some embodiments, step (c) results in an apparent growth rate of greater than 1% per day, greater than 1.5% per day, greater than 2% per day, greater than 2.5% per day, greater than 3% per day, greater than 3.5% per day, greater than 4.0% per day, greater than 4.5% per day, greater than 5.0% per day, greater than 5.5% per day, greater than 6.0% per day, greater than 6.5% per day, greater than 7.0% per day, greater than 7.5% per day, greater than 8.0% per day, greater than 8.5% per day, greater than 9.0% per day, greater than 9.5% per day, greater than 10.0% per day, greater than 10.5% per day, greater than 11.0% per day, greater than 11.5% per day, greater than 12.0% per day, greater than 12.5% per day, greater than 13.0% per day, greater than 13.5% per day, greater than 14.0% per day, greater than 14.5% per day, greater than 15.0% per day, greater than 16% per day, greater than 17% per day, greater than 18% per day, greater than 19% per day, greater than 20% per day, greater than 21% per day, greater than 22% per day, greater than 23% per day, greater than 24% per day, greater than 25% per day, greater than 30% per day, greater than 35% per day, greater than 40% per day, greater than 45% per day, greater than 50% per day, greater than 55% per day, greater than 60% per day, greater than 65% per day, greater than 70% per day, greater than 75% per day, greater than 80% per day, greater than 85% per day, greater than 90% per day, greater than 95% per day, greater than 100% per day, greater than 105% per day, greater than 110% per day, greater than 115% per day, greater than 120% per day, greater than 125% per day, greater than 130% per day, greater than 135% per day, greater than 140% per day, greater than 145% per day, or greater than 150% per day, during the culturing of the cell in the production bioreactor. In some embodiments of these methods, step (c) results in an apparent growth rate of about 0.1% per day to about 150% per day (or any of the subranges of this range described herein) during the culturing of the cell in the production bioreactor.

In some embodiments of these methods, the cell (e.g., any of the cells described herein) contains a nucleic acid encoding a recombinant therapeutic protein (e.g., any of the recombinant therapeutic proteins described herein). Some embodiments of these methods further include collecting or recovering the recombinant therapeutic protein. Some embodiments of these methods further include purifying the recombinant therapeutic protein. Some embodiments of these methods further include formulating the purified recombinant therapeutic protein. In some embodiments of these methods, the cell is a bacterium (e.g., any of the exemplary bacteria described herein or known in the art), a yeast cell (e.g., any of the exemplary yeast cells described herein or known in the art), or a mammalian cell (e.g., any of the exemplary mammalian cells described herein or known in the art).

In some embodiments of these methods, the cell viability is determined by measuring a concentration of lactic acid dehydrogenase (LDH) in the test culture vessel. In some embodiments of these methods, the test culture vessel is a baffled shake flask and the plurality of test conditions include (or consist) of one or more (e.g., two or three) of: (a) a rotary agitation of about 125 RPM to about 400 RPM (or any of the subranges of this range described herein); (b) a concentration of a sensitizer (e.g., any of the sensitizers described herein or known in the art) of about 0 ppm to about 120 ppm (or any of the subranges of this range described herein); and (c) a concentration of a protectant (e.g., any of the protectants described herein or known in the art) that is about 1 g/L to about 10 g/L (or any of the subranges of this range described herein). In some embodiments of these methods, the protectant is a poloxamer (e.g., poloxamer-188, poloxamer-401, poloxamer-402, or poloxamer-407), a poloxamine (e.g., poloxamine-904 or poloxamine-908), or a non-ionic surfactant Pluronic®.

Methods for Predicting Cell Viability in a Production Bioreactor

Also provided herein are methods of predicting cell viability in a production bioreactor (e.g., any of the production bioreactors described herein) that include: (a) selecting a set of parameters comprising at least two parameters (e.g., 2, 3, 4, 5, or 6); (b) determining cell viability under a plurality of test conditions as defined by the set of parameters in a test culture vessel (e.g., any of the text culture vessels described herein); and (c) based on the cell viability in the test culture vessel under the plurality of conditions, predicting cell viability in the production bioreactor.

In some embodiments of these methods, the set of parameters comprises, consists essentially of, or consists of shear stress, concentration of a sensitizer (e.g., any of the exemplary sensitizers described herein or known in the art), and concentration of a protectant (e.g., any of the protectants described herein or known in the art). In some embodiments of these methods, the plurality of test conditions are selected based on full factorial screening and/or inscribed center composite design.

In some embodiments of these methods, the sensitizer is an antifoam (e.g., a polydimethylsiloxane-based antifoam, simethicone, or any other antifoam described herein or known in the art).

In some embodiments of these methods, the test culture vessel (e.g., any of the test culture vessels described herein or known in the art) has a volume of about 5 mL to about 5 L (or any of the subranges of this range described herein). In some embodiments of these methods, the test culture vessel is a shake flask, e.g., a baffled shake flask (e.g., any of the baffled shake flasks described herein or known in the art).

In some embodiments of these methods, the production bioreactor (e.g., any of the production bioreactors described herein) has a volume of about 5 L to about 20,000 L (or any of the subranges of this range described herein). In some examples, the production bioreactor is a perfusion bioreactor. In other examples, the production bioreactor is a fed batch bioreactor.

Some embodiments of these methods further include culturing a cell in the production bioreactor using a condition predicted to result in a specific cell death rate of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% per day, during the culturing of the cells in the production bioreactor. Some embodiments of these methods further include culturing a cell in the production bioreactor using a condition predicted to result in a specific cell death rate of about 0.1% to about 40% per day (or any of the subranges of this range described herein) during the culturing of the cells in the production bioreactor.

Some embodiments of these methods further include culturing a cell in the production bioreactor using a condition predicted to result in a cell specific LDH production of less than 150 nU/cell/day, less than 145 nU/cell/day, less than 140 nU/cell/day, less than 135 nU/cell/day, less than 130 nU/cell/day, less than 125 nU/cell/day, less than 120 nU/cell/day, less than 115 nU/cell/day, less than 150 nU/cell/day, less than 110 nU/cell/day, less than 105 nU/cell/day, less than 100 nU/cell/day, less than 95 nU/cell/day, less than 90 nU/cell/day, less than 85 nU/cell/day, less than 80 nU/cell/day, less than 75 nU/cell/day, less than 70 nU/cell/day, less than 65 nU/cell/day, less than 60 nU/cell/day, less than 55 nU/cell/day, less than 50 nU/cell/day, less than 45 nU/cell/day, less than 45 nU/cell/day, less than 40 nU/cell/day, less than 35 nU/cell/day, less than 30 nU/cell/day, less than 25 nU/cell/day, less than 20 nU/cell/day, less than 15 nU/cell/day, less than 10 nU/cell/day, less than 5 nU/cell/day, or less than less than 1 nU/cell/day, during the culturing of the cell in the production bioreactor. Some embodiments of these methods further include culturing a cell in the production bioreactor using a condition predicted to result in a cell specific LDH production of about 0.1 nU/cell/day to about 150 nU/cell/day (or any of the subranges of this range described herein) during the culturing of the cell in the production bioreactor.

Some embodiments of these methods further include culturing a cell in the production bioreactor using a condition predicted to result in an apparent growth rate of greater than 1% per day, greater than 1.5% per day, greater than 2% per day, greater than 2.5% per day, greater than 3% per day, greater than 3.5% per day, greater than 4.0% per day, greater than 4.5% per day, greater than 5.0% per day, greater than 5.5% per day, greater than 6.0% per day, greater than 6.5% per day, greater than 7.0% per day, greater than 7.5% per day, greater than 8.0% per day, greater than 8.5% per day, greater than 9.0% per day, greater than 9.5% per day, greater than 10.0% per day, greater than 10.5% per day, greater than 11.0% per day, greater than 11.5% per day, greater than 12.0% per day, greater than 12.5% per day, greater than 13.0% per day, greater than 13.5% per day, greater than 14.0% per day, greater than 14.5% per day, greater than 15.0% per day, greater than 16% per day, greater than 17% per day, greater than 18% per day, greater than 19% per day, greater than 20% per day, greater than 21% per day, greater than 22% per day, greater than 23% per day, greater than 24% per day, greater than 25% per day, greater than 30% per day, greater than 35% per day, greater than 40% per day, greater than 45% per day, greater than 50% per day, greater than 55% per day, greater than 60% per day, greater than 65% per day, greater than 70% per day, greater than 75% per day, greater than 80% per day, greater than 85% per day, greater than 90% per day, greater than 95% per day, greater than 100% per day, greater than 105% per day, greater than 110% per day, greater than 115% per day, greater than 120% per day, greater than 125% per day, greater than 130% per day, greater than 135% per day, greater than 140% per day, greater than 145% per day, or greater than 150% per day, during the culturing of the cell in the production bioreactor. Some embodiments of these methods further include culturing a cell in the production bioreactor using a condition predicted to result in an apparent growth rate of about 0.1% per day to about 150% per day (or any of the subranges of this range described herein) during the culturing of the cell in the production bioreactor.

In some embodiments of these methods, the cell (e.g., any of the cells described herein) contains a nucleic acid encoding a recombinant therapeutic protein (e.g., any of the recombinant therapeutic proteins described herein). Some embodiments of these methods further include collecting or recovering the recombinant therapeutic protein. Some embodiments of these methods further include purifying the recombinant therapeutic protein. Some embodiments of these methods further include formulating the purified recombinant therapeutic protein. In some embodiments of these methods, the cell is a bacterium (e.g., any of the exemplary bacteria described herein or known in the art), a yeast cell (e.g., any of the exemplary yeast cells described herein or known in the art), or a mammalian cell (e.g., any of the exemplary mammalian cells described herein or known in the art).

In some embodiments of these methods, the cell viability is determined by measuring a concentration of lactic acid dehydrogenase (LDH) in the test culture vessel. In some embodiments of these methods, the test culture vessel is a baffled shake flask and the plurality of test conditions include (or consist) of one or more (e.g., two or three) of: (a) a rotary agitation of about 125 RPM to about 400 RPM (or any of the subranges of this range described herein); (b) a concentration of a sensitizer (e.g., any of the sensitizers described herein or known in the art) of about 0 ppm to about 120 ppm (or any of the subranges of this range described herein); and (c) a concentration of a protectant (e.g., any of the protectants described herein or known in the art) that is about 1 g/L to about 10 g/L (or any of the subranges of this range described herein). In some embodiments of these methods, the protectant is a poloxamer (e.g., poloxamer-188, poloxamer-401, poloxamer-402, or poloxamer-407), a poloxamine (e.g., poloxamine-904 or poloxamine-908), or a non-ionic surfactant Pluronic®.

Methods for Culturing a Cell in a Production Bioreactor

Also provided herein are methods of culturing a cell (e.g., any of the cells described herein) in a production bioreactor that include culturing the cell in a liquid culture medium under one or more (e.g., two, three, or four) of the following conditions:

(a) the production bioreactor has a P/V (W/m$^3$) from about 1.0 to about 110 (e.g., from about 3.0 to about 7.0, from about 4.0 to about 6.0, from about 5.0 to about 6.0, or about 6.0) (e.g., about 1.0 to about 110, about 1.0 to about 95, about 1.0 to about 90, about 1.0 to about 85, about 1.0 to about 80, about 1.0 to about 75, about 1.0 to about 70, about 1.0 to about 65, about 1.0 to about 60, about 1.0 to about 55, about 1.0 to about 50, about 1.0 to about 45, about 1.0 to about 40, about 1.0 to about 35, about 1.0 to about 30, about 1.0 to about 25, about 1.0 to about 20, about 1.0 to about 18, about 1.0 to about 16, about 1.0 to about 14, about 1.0 to about 12, about 1.0 to about 10, about 1.0 to about 9.0, about 1.0 to about 8.0, about 1.0 to about 7.0, about 1.0 to about 6.0, about 1.0 to about 5.0, about 1.0 to about 4.0, about 1.0 to about 3.0, to about 1.0 to about 2.0, about 2.0 to about 110, about 2.0 to about 95, about 2.0 to about 90, about 2.0 to about 85, about 2.0 to about 80, about 2.0 to about 75, about 2.0 to about 70, about 2.0 to about 65, about 2.0 to about 60, about 2.0 to about 55, about 2.0 to about 50, about 2.0 to about 45, about 2.0 to about 40, about 2.0 to about 35, about 2.0 to about 30, about 2.0 to about 25, about 2.0 to about 20, about 2.0 to about 18, about 2.0 to about 16, about 2.0 to about 14, about 2.0 to about 12, about 2.0 to about 10, about 2.0 to about 9.0, about 2.0 to about 8.0, about 2.0 to about 7.0, about 2.0 to about 6.0, about 2.0 to about 5.0, about 2.0 to about 4.0, about 2.0 to about 3.0, about 3.0 to about 110, about 3.0 to about 95, about 3.0 to about 90, about 3.0 to about 85, about 3.0 to about 80, about 3.0 to about 75, about 3.0 to about 70, about 3.0 to about 65, about 3.0 to about 60, about 3.0 to about 55, about 3.0 to about 50, about 3.0 to about 45, about 3.0 to about 40, about 3.0 to about 35, about 3.0 to about 30, about 3.0 to about 25, about 3.0 to about 20, about 3.0 to about 18, about 3.0 to about 16, about 3.0 to about 14, about 3.0 to about 12, about 3.0 to about 10, about 3.0 to about 9.0, about 3.0 to about 8.0, about 3.0 to about 7.0, about 3.0 to about 6.0, about 3.0 to about 5.0, about 3.0 to about 4.0, about 4.0 to about 110, about 4.0 to about 95, about 4.0 to about 90, about 4.0 to about 85, about 4.0 to about 80, about 4.0 to about 75, about 4.0 to about 70, about 4.0 to about 65, about 4.0 to about 60, about 4.0 to about 55, about 4.0 to about 50, about 4.0 to about 45, about 4.0 to about 40, about 4.0 to about 35, about 4.0 to about 30, about 4.0 to about 25, about 4.0 to about 20, about 4.0 to about 18, about 4.0 to about 16, about 4.0 to about 14, about 4.0 to about 12, about 4.0 to about 10, about 4.0 to about 9.0, about 4.0 to about 8.0, about 4.0 to about 7.0, about 4.0 to about 6.0, about 4.0 to about 5.0, about 5.0 to about 110, about 5.0 to about 95, about 5.0 to about 90, about 5.0 to about 85, about 5.0 to about 80, about 5.0 to about 75, about 5.0 to about 70, about 5.0 to about 65, about 5.0 to about 60, about 5.0 to about 55, about 5.0 to about 50, about 5.0 to about 45, about 5.0 to about 40, about 5.0 to about 35, about 5.0 to about 30, about 5.0 to about 25, about 5.0 to about 20, about 5.0 to about 18, about 5.0 to about 16, about 5.0 to about 14, about 5.0 to about 12, about 5.0 to about 10, about 5.0 to about 9.0, about 5.0 to about 8.0, about 5.0 to about 7.0, about 5.0 to about 6.0, about 6.0 to about 110, about 6.0 to about 95, about 6.0 to about 90, about 6.0 to about 85, about 6.0 to about 80, about 6.0 to about 75, about 6.0 to about 70, about 6.0 to about 65, about 6.0 to about 60, about 6.0 to about 55, about 6.0 to about 50, about 6.0 to about 45, about 6.0 to about 40, about 6.0 to about 35, about 6.0 to about 30, about 6.0 to about 25, about 6.0 to about 20, about 6.0 to about 18, about 6.0 to about 16, about 6.0 to about 14, about 6.0 to about 12, about 6.0 to about 10, about 6.0 to about 9.0, about 6.0 to about 8.0, about 6.0 to about 7.0, about 7.0 to about 110, about 7.0 to about 95, about 7.0 to about 90, about 7.0 to about 85, about 7.0 to about 80, about 7.0 to about 75, about 7.0 to about 70, about 7.0 to about 65, about 7.0 to about 60, about 7.0 to about 55, about 7.0 to about 50, about 7.0 to about 45, about 7.0 to about 40, about 7.0 to about 35, about 7.0 to about 30, about 7.0 to about 25, about 7.0 to about 20, about 7.0 to about 18, about 7.0 to about 16, about 7.0 to about 14, about 7.0 to about 12, about 7.0 to about 10, about 7.0 to about 9.0, about 7.0 to about 8.0, about 8.0 to about 110, about 8.0 to about 95, about 8.0 to about 90, about 8.0 to about 85, about 8.0 to about 80, about 8.0 to about 75, about 8.0 to about 70, about 8.0 to about 65, about 8.0 to about 60, about 8.0 to about 55, about 8.0 to about 50, about 8.0 to about 45, about 8.0 to about 40, about 8.0 to about 35, about 8.0 to about 30, about 8.0 to about 25, about 8.0 to about 20, about 8.0 to about 18, about 8.0 to about 16, about 8.0 to about 14, about 8.0 to about 12, about 8.0 to about 10, about 8.0 to about 9.0, about 9.0 to about 110, about 9.0 to about 95, about 9.0 to about 90, about 9.0 to about 85, about 9.0 to about 80, about 9.0 to about 75, about 9.0 to about 70, about 9.0 to about 65, about 9.0 to about 60, about 9.0 to about 55, about 9.0 to about 50, about 9.0 to about 45, about 9.0 to about 40, about 9.0 to about 35, about 9.0 to about 30, about 9.0 to about 25, about 9.0 to about 20, about 9.0 to about 18, about 9.0 to about 16, about 9.0 to about 14, about 9.0 to about 12, about 9.0 to about 10, about 10 to about 110, about 10 to about 95, about 10 to about 90, about 10 to about 85, about 10 to about 80, about 10 to about 75, about 10 to about 70, about 10 to about 65, about 10 to about 60, about 10 to about 55, about 10 to about 50, about 10 to about 45, about 10 to about 40, about 10 to about 35, about 10 to about 30, about 10 to about 25, about 10 to about 20, about 10 to about 18, about 10 to about 16, about 10 to about 14, about 10 to about 12, about 12 to about 110, about 12 to about 95, about 12 to about 90, about 12 to about 85, about 12 to about 80, about 12 to about 75, about 12 to about 70, about 12 to about 65, about 12 to about 60, about 12 to about 55, about 12 to about 50, about 12 to about 45, about 12 to about 40, about 12 to about 35, about 12 to about 30, about 12 to about 25, about 12 to about 20, about 12 to about 18, about 12 to about 16, about 12 to about 14, about 14 to about 110, about 14 to about 95, about 14 to about 90, about 14 to about 85, about 14 to about 80, about 14 to about 75, about 14 to about 70, about 14 to about 65, about 14 to about 60, about 14 to about 55, about 14 to about 50, about 14 to about 45, about 14 to about 40, about 14 to about 35, about 14 to about 30, about 14 to about 25, about 14 to about 20, about 14 to about 18, about 14 to about 16, about 16 to about 110, about 16 to about 95, about 16 to about 90, about 16 to about 85, about 16 to about 80, about 16 to about 75, about 16 to about 70, about 16 to about 65, about 16 to about 60, about 16 to about 55, about 16 to about 50, about 16 to about 45, about 16 to about 40, about 16 to about 35, about 16 to about 30, about 16 to about 25, about 16 to about 20, about 16 to about 18, about 18 to about 110, about 18 to about 95, about 18 to about 90, about 18 to about 85, about 18 to about 80, about 18 to about 75, about 18 to about 70, about 18 to about 65, about 18 to about 60, about 18 to about 55, about 18 to about 50, about 18 to about 45, about 18 to about 40, about 18 to about 35, about 18 to about 30, about 18 to about 25, about 18 to about 20, about 20 to about 110, about 20 to about 95, about 20 to about 90, about 20 to about 85, about 20 to about 80, about 20 to about 75, about 20 to about 70, about 20 to about 65, about 20 to about 60, about 20 to about 55, about 20 to about 50, about 20 to about 45, about 20 to about 40, about 20 to about 35, about 20 to about 30, about 20 to about 25, about 25 to about 110, about 25 to about 95, about 25 to about 90, about 25 to about 85, about 25 to about 80, about 25 to about 75, about 25 to about 70, about 25 to about 65, about 25 to about 60, about 25 to about 55, about 25 to about 50, about 25 to about 45, about 25 to about 40, about 25 to about 35, about 25 to about 30, about 30 to about 110, about 30 to about 95, about 30 to about 90, about 30 to about 85, about 30 to about 80, about 30 to about 75, about 30 to about 70, about 30 to about 65, about 30 to about 60, about 30 to about 55, about 30 to about 50, about 30 to about 45, about 30 to about 40, about 30 to about 35, about 35 to about 110, about 35 to about 95, about 35 to about 90, about 35 to about 85, about 35 to about 80, about 35 to about 75, about 35 to about 70, about 35 to about 65, about 35 to about 60, about 35 to about 55, about 35 to about 50, about 35 to about 45, about 35 to about 40, about 40 to about 110, about 40 to about 95, about 40 to about 90, about 40 to about 85, about 40 to about 80, about 40 to about 75, about 40 to about 70, about 40 to about 65, about 40 to about 60, about 40 to about 55, about 40 to about 50, about 40 to about 45, about 45 to about 110, about 45 to about 95, about 45 to about 90, about 45 to about 85, about 45 to about 80, about 45 to about 75, about 45 to about 70, about 45 to about 65, about 45 to about 60, about 45 to about 55, about 45 to about 50, about 50 to about 110, about 50 to about 95, about 50 to about 90, about 50 to about 85, about 50 to about 80, about 50 to about 75, about 50 to about 70, about 50 to about 65, about 50 to about 60, about 50 to about 55, about 55 to about 110, about 55 to about 95, about 55 to about 90, about 55 to about 85, about 55 to about 80, about 55 to about 75, about 55 to about 70, about 55 to about 65, about 55 to about 60, about 60 to about 110, about 60 to about 95, about 60 to about 90, about 60 to about 85, about 60 to about 80, about 60 to about 75, about 60 to about 70, about 60 to about 65, about 65 to about 110, about 65 to about 95, about 65 to about 90, about 65 to about 85, about 65 to about 80, about 65 to about 75, about 65 to about 70, about 70 to about 110, about 70 to about 95, about 70 to about 90, about 70 to about 85, about 70 to about 80, about 70 to about 75, about 75 to about 110, about 75 to about 95, about 75 to about 90, about 75 to about 85, about 75 to about 80, about 80 to about 110, about 80 to about 95, about 80 to about 90, about 80 to about 85, about 85 to about 110, about 85 to about 95, about 85 to about 90, about 90 to about 110, about 90 to about 95, about 95 to about 110, about 95 to about 105, about 95 to about 100, about 100 to about 110, about 100 to about 105, or about 105 to about 110);

(b) the production bioreactor has a volume of air per volume of liquid per minute (VVM) (min$^{-1}$) from about 0.01 to about 0.10 (e.g., from about 0.02 to about 0.08, from about 0.04 to about 0.06, or about 0.06) (e.g., about 0.01 to about 0.10, about 0.01 to about 0.09, about 0.01 to about 0.08, about 0.01 to about 0.07, about 0.01 to about 0.06, about 0.01 to about 0.05, about 0.01 to about 0.04, about 0.01 to about 0.03, about 0.01 to about 0.02, about 0.02 to about 0.10, about 0.02 to about 0.09, about 0.02 to about 0.08, about 0.02 to about 0.07, about 0.02 to about 0.06, about 0.02 to about 0.05, about 0.02 to about 0.04, about 0.02 to about 0.03, about 0.03 to about 0.10, about 0.03 to about 0.09, about 0.03 to about 0.08, about 0.03 to about 0.07, about 0.03 to about 0.06, about 0.03 to about 0.05, about 0.03 to about 0.04, about 0.04 to about 0.10, about 0.04 to about 0.09, about 0.04 to about 0.08, about 0.04 to about 0.07, about 0.04 to about 0.06, about 0.04 to about 0.05, about 0.05 to about 0.10, about 0.05 to about 0.09, about 0.05 to about 0.08, about 0.05 to about 0.07, about 0.05 to about 0.06, about 0.06 to about 0.10, about 0.06 to about 0.09, about 0.06 to about 0.08, about 0.06 to about 0.07, about 0.07 to about 0.10, about 0.07 to about 0.09, about 0.07 to about 0.08, about 0.08 to about 0.10, about 0.08 to about 0.09, or about 0.09 to about 0.10);

(c) the medium comprises a sensitizer (e.g., any of the sensitizers described herein or known in the art) that has a concentration of about 0 ppm to about 5,000 ppm (or any of the subranges of this range described herein); and (d) the liquid culture medium comprises a protectant (e.g., any of the protectants described herein or known in the art) that has a concentration that is from about 1 g/L to about 15 g/L (e.g., any of the subranges of this range described herein, e.g., about 1 g/L to about 15 g/L, about 1 g/L to about 14 g/L, about 1 g/L to about 13 g/L, about 1 g/L to about 12 g/L, about 1 g/L to about 11 g/L, about 2 g/L to about 15 g/L, about 2 g/L to about 14 g/L, about 2 g/L to about 13 g/L, about 2 g/L to about 12 g/L, about 2 g/L to about 11 g/L, about 3 g/L to about 15 g/L, about 3 g/L to about 14 g/L, about 3 g/L to about 13 g/L, about 3 g/L to about 12 g/L, about 3 g/L to about 11 g/L, about 4 g/L to about 15 g/L, about 4 g/L to about 14 g/L, about 4 g/L to about 13 g/L, about 4 g/L to about 12 g/L, about 4 g/L to about 11 g/L, about 5 g/L to about 15 g/L, about 5 g/L to about 14 g/L, about 5 g/L to about 13 g/L, about 5 g/L to about 12 g/L, about 5 g/L to about 11 g/L, about 6 g/L to about 15 g/L, about 6 g/L to about 14 g/L, about 6 g/L to about 13 g/L, about 6 g/L to about 12 g/L, about 6 g/L to about 11 g/L, about 7 g/L to about 15 g/L, about 7 g/L to about 14 g/L, about 7 g/L to about 13 g/L, about 7 g/L to about 12 g/L, about 7 g/L to about 11 g/L, about 8 g/L to about 15 g/L, about 8 g/L to about 14 g/L, about 8 g/L to about 13 g/L, about 8 g/L to about 12 g/L, about 8 g/L to about 11 g/L, about 9 g/L to about 15 g/L, about 9 g/L to about 14 g/L, about 9 g/L to about 13 g/L, about 9 g/L to about 12 g/L, about 9 g/L to about 11 g/L, about 10 g/L to about 15 g/L, about 10 g/L to about 14 g/L, about 10 g/L to about 13 g/L, about 10 g/L to about 12 g/L, about 10 g/L to about 11 g/L, about 11 g/L to about 15 g/L, about 11 g/L to about 14 g/L, about 11 g/L to about 13 g/L, about 11 g/L to about 12 g/L, about 12 g/L to about 15 g/L, about 12 g/L to about 14 g/L, about 12 g/L to about 13 g/L, about 13 g/L to about 15 g/L, about 13 g/L to about 14 g/L, or about 14 g/L to about 15 g/L).

Under the optimized conditions, the specific cell death rate can be less than or predicted to be less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% per day. Under optimized conditions, the specific cell death rate can be about 0.1% to about 40% (or any of the subranges of this range described herein).

In some embodiments, the cell viability can be determined by measuring the concentration of lactic acid dehydrogenase (LDH). The cell specific LDH production (nU/cell/day) can be less than or predicted to be less than 1, 2, 3, 4, 5, 6, 7, 8, 9, 10, 20, 30, 40, 50, 60, 70, 80, 90, 100, 110, 120, 130, 140, 150, 160, 170, 180, 190, or 200 (e.g., 150). In some embodiments, the LDH production (nU/cell/day) can be about 0.1 to about 200 (e.g., any of the subranges of this range described herein, e.g., about 0.1 to about 200, about 0.1 to about 190, about 0.1 to about 180, about 0.1 to about 170, about 0.1 to about 160, about 0.5 to about 200, about 0.5 to about 190, about 0.5 to about 180, about 0.5 to about 170, about 0.5 to about 160, about 1.0 to about 200, about 1.0 to about 190, about 1.0 to about 180, about 1.0 to about 170, about 1.0 to about 160, about 2.5 to about 200, about 2.5 to about 190, about 2.5 to about 180, about 2.5 to about 170, about 2.5 to about 160, about 5.0 to about 200, about 5.0 to about 190, about 5.0 to about 180, about 5.0 to about 170, about 5.0 to about 160, about 10 to about 200, about 10 to about 190, about 10 to about 180, about 10 to about 170, about 10 to about 160, about 20 to about 200, about 20 to about 190, about 20 to about 180, about 20 to about 170, about 20 to about 160, about 30 to about 200, about 30 to about 190, about 30 to about 180, about 30 to about 170, about 30 to about 160, about 40 to about 200, about 40 to about 190, about 40 to about 180, about 40 to about 170, about 40 to about 160, about 50 to about 200, about 50 to about 190, about 50 to about 180, about 50 to about 170, about 50 to about 160, about 60 to about 200, about 60 to about 190, about 60 to about 180, about 60 to about 170, about 60 to about 160, about 70 to about 200, about 70 to about 190, about 70 to about 180, about 70 to about 170, about 70 to about 160, about 80 to about 200, about 80 to about 190, about 80 to about 180, about 80 to about 170, about 80 to about 160, about 90 to about 200, about 90 to about 190, about 90 to about 180, about 90 to about 170, about 90 to about 160, about 100 to about 200, about 100 to about 190, about 100 to about 180, about 100 to about 170, about 100 to about 160, about 110 to about 200, about 110 to about 190, about 110 to about 180, about 110 to about 170, about 110 to about 160, about 120 to about 200, about 120 to about 190, about 120 to about 180, about 120 to about 170, about 120 to about 160, about 130 to about 200, about 130 to about 190, about 130 to about 180, about 130 to about 170, about 130 to about 160, about 140 to about 200, about 140 to about 190, about 140 to about 180, about 140 to about 170, about 140 to about 160, about 150 to about 200, about 150 to about 190, about 150 to about 180, about 150 to about 170, about 150 to about 160, about 160 to about 200, about 160 to about 190, about 160 to about 180, about 160 to about 170, about 170 to about 200, about 170 to about 190, about 170 to about 180, about 180 to about 200, about 180 to about 190, or about 190 to about 200).

In some embodiments, the apparent growth rate can be more than or predicted to be greater than 1% per day, greater than 1.5% per day, greater than 2% per day, greater than 2.5% per day, greater than 3% per day, greater than 3.5% per day, greater than 4.0% per day, greater than 4.5% per day, greater than 5.0% per day, greater than 5.5% per day, greater than 6.0% per day, greater than 6.5% per day, greater than 7.0% per day, greater than 7.5% per day, greater than 8.0% per day, greater than 8.5% per day, greater than 9.0% per day, greater than 9.5% per day, greater than 10.0% per day, greater than 10.5% per day, greater than 11.0% per day, greater than 11.5% per day, greater than 12.0% per day, greater than 12.5% per day, greater than 13.0% per day, greater than 13.5% per day, greater than 14.0% per day, greater than 14.5% per day, greater than 15.0% per day, greater than 16% per day, greater than 17% per day, greater than 18% per day, greater than 19% per day, greater than 20% per day, greater than 21% per day, greater than 22% per day, greater than 23% per day, greater than 24% per day, greater than 25% per day, greater than 30% per day, greater than 35% per day, greater than 40% per day, greater than 45% per day, greater than 50% per day, greater than 55% per day, greater than 60% per day, greater than 65% per day, greater than 70% per day, greater than 75% per day, greater than 80% per day, greater than 85% per day, greater than 90% per day, greater than 95% per day, greater than 100% per day, greater than 105% per day, greater than 110% per day, greater than 115% per day, greater than 120% per day, greater than 125% per day, greater than 130% per day, greater than 135% per day, greater than 140% per day, greater than 145% per day, or greater than 150% per day. In some embodiments, the apparent growth rate can be about 0.1% per day to about 150% per day (e.g., any of the subranges of this range described herein, e.g., about 0.1% to about 48%, about 0.1% to about 46%, about 0.1% to about 44%, about 0.1% to about 42%, about 0.5% to about 50%, about 0.5% to about 48%, about 0.5% to about 46%, about 0.5% to about 44%, about 0.5% to about 42%, about 1.0% to about 50%, about 1.0% to about 48%, about 1.0% to about 46%, about 1.0% to about 44%, about 1.0% to about 42%, about 2.0% to about 50%, about 2.0% to about 48%, about 2.0% to about 46%, about 2.0% to about 44%, about 2.0% to about 42%, about 4.0% to about 50%, about 4.0% to about 48%, about 4.0% to about 46%, about 4.0% to about 44%, about 4.0% to about 42%, about 6.0% to about 50%, about 6.0% to about 48%, about 6.0% to about 46%, about 6.0% to about 44%, about 6.0% to about 42%, about 8.0% to about 50%, about 8.0% to about 48%, about 8.0% to about 46%, about 8.0% to about 44%, about 8.0% to about 42%, about 10% to about 50%, about 10% to about 48%, about 10% to about 46%, about 10% to about 44%, about 10% to about 42%, about 12% to about 50%, about 12% to about 48%, about 12% to about 46%, about 12% to about 44%, about 12% to about 42%, about 14% to about 50%, about 14% to about 48%, about 14% to about 46%, about 14% to about 44%, about 14% to about 42%, about 16% to about 50%, about 16% to about 48%, about 16% to about 46%, about 16% to about 44%, about 16% to about 42%, about 18% to about 50%, about 18% to about 48%, about 18% to about 46%, about 18% to about 44%, about 18% to about 42%, about 20% to about 50%, about 20% to about 48%, about 20% to about 46%, about 20% to about 44%, about 20% to about 42%, about 22% to about 50%, about 22% to about 48%, about 22% to about 46%, about 22% to about 44%, about 22% to about 42%, about 24% to about 50%, about 24% to about 48%, about 24% to about 46%, about 24% to about 44%, about 24% to about 42%, about 26% to about 50%, about 26% to about 48%, about 26% to about 46%, about 26% to about 44%, about 26% to about 42%, about 28% to about 50%, about 28% to about 48%, about 28% to about 46%, about 28% to about 44%, about 28% to about 42%, about 30% to about 50%, about 30% to about 48%, about 30% to about 46%, about 30% to about 44%, about 30% to about 42%, about 32% to about 50%, about 32% to about 48%, about 32% to about 46%, about 32% to about 44%, about 32% to about 42%, about 34% to about 50%, about 34% to about 48%, about 34% to about 46%, about 34% to about 44%, about 34% to about 42%, about 36% to about 50%, about 36% to about 48%, about 36% to about 46%, about 36% to about 44%, about 36% to about 42%, about 38% to about 50%, about 38% to about 48%, about 38% to about 46%, about 38% to about 44%, about 38% to about 42%, about 40% to about 50%, about 40% to about 48%, about 40% to about 46%, about 40% to about 44%, about 40% to about 42%, about 42% to about 50%, about 42% to about 48%, about 42% to about 46%, about 42% to about 44%, about 44% to about 50%, about 44% to about 48%, about 44% to about 46%, about 46% to about 50%, about 46% to about 48%, or about 48% to about 50%).

In some embodiments of these methods, the sensitizer is an antifoam agent (e.g., a polydimethylsiloxane-based antifoam, simethicone, or any of the other antifoams described herein or known in the art). In some embodiments, the protectant is a poloxamer (e.g., poloxamer-188, poloxamer-401, poloxamer-402, or poloxamer-407), a poloxamine (e.g., poloxamine-904 or poloxamine-908), or a non-ionic surfactant Pluronic®.

In some embodiments of these methods, the production bioreactor (e.g., any of the exemplary production bioreactors described herein or known in the art) has a volume of about 5 L to about 20,000 L (or any of the subranges of this range described herein). In some embodiments of these methods, the production bioreactor is a perfusion bioreactor. In some embodiments of these methods, the production bioreactor is a fed batch bioreactor.

In some embodiments, the method results in a specific cell death rate of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% per day, during the culturing of the cell in the production bioreactor. In some embodiments, the method results in a specific cell death rate of about 0.1% to about 40% per day (or any of the subranges of this range described herein) during the culturing of the cell in the production bioreactor.

In some embodiments, the method results in a cell specific LDH production of less than 150 nU/cell/day, less than 145 nU/cell/day, less than 140 nU/cell/day, less than 135 nU/cell/day, less than 130 nU/cell/day, less than 125 nU/cell/day, less than 120 nU/cell/day, less than 115 nU/cell/day, less than 150 nU/cell/day, less than 110 nU/cell/day, less than 105 nU/cell/day, less than 100 nU/cell/day, less than 95 nU/cell/day, less than 90 nU/cell/day, less than 85 nU/cell/day, less than 80 nU/cell/day, less than 75 nU/cell/day, less than 70 nU/cell/day, less than 65 nU/cell/day, less than 60 nU/cell/day, less than 55 nU/cell/day, less than 50 nU/cell/day, less than 45 nU/cell/day, less than 45 nU/cell/day, less than 40 nU/cell/day, less than 35 nU/cell/day, less than 30 nU/cell/day, less than 25 nU/cell/day, less than 20 nU/cell/day, less than 15 nU/cell/day, less than 10 nU/cell/day, less than 5 nU/cell/day, or less than less than 1 nU/cell/day, during the culturing of the cell in the production bioreactor. In some embodiments of these methods, the method results in a cell specific LDH production of about 0.1 nU/cell/day to about 150 nU/cell/day (or any of the subranges of this range described herein) during the culturing of the cell in the production bioreactor.

In some embodiments, the method results in an apparent growth rate of greater than 1% per day, greater than 1.5% per day, greater than 2% per day, greater than 2.5% per day, greater than 3% per day, greater than 3.5% per day, greater than 4.0% per day, greater than 4.5% per day, greater than 5.0% per day, greater than 5.5% per day, greater than 6.0% per day, greater than 6.5% per day, greater than 7.0% per day, greater than 7.5% per day, greater than 8.0% per day, greater than 8.5% per day, greater than 9.0% per day, greater than 9.5% per day, greater than 10.0% per day, greater than 10.5% per day, greater than 11.0% per day, greater than 11.5% per day, greater than 12.0% per day, greater than 12.5% per day, greater than 13.0% per day, greater than 13.5% per day, greater than 14.0% per day, greater than 14.5% per day, greater than 15.0% per day, greater than 16% per day, greater than 17% per day, greater than 18% per day, greater than 19% per day, greater than 20% per day, greater than 21% per day, greater than 22% per day, greater than 23% per day, greater than 24% per day, greater than 25% per day, greater than 30% per day, greater than 35% per day, greater than 40% per day, greater than 45% per day, greater than 50% per day, greater than 55% per day, greater than 60% per day, greater than 65% per day, greater than 70% per day, greater than 75% per day, greater than 80% per day, greater than 85% per day, greater than 90% per day, greater than 95% per day, greater than 100% per day, greater than 105% per day, greater than 110% per day, greater than 115% per day, greater than 120% per day, greater than 125% per day, greater than 130% per day, greater than 135% per day, greater than 140% per day, greater than 145% per day, or greater than 150% per day, during the culturing of the cell in the production bioreactor. In some embodiments of these methods, the method results in an apparent growth rate of about 0.1% per day to about 150% per day (or any of the subranges of this range described herein) during the culturing of the cell in the production bioreactor.

In some embodiments of these methods, the cell (e.g., any of the cells described herein) contains a nucleic acid encoding a recombinant therapeutic protein (e.g., any of the recombinant therapeutic proteins described herein). Some embodiments of these methods further include collecting or recovering the recombinant therapeutic protein. Some embodiments of these methods further include purifying the recombinant therapeutic protein. Some embodiments of these methods further include formulating the purified recombinant therapeutic protein.

In some embodiments of these methods, the cell is a bacterium (e.g., any of the exemplary bacteria described herein or known in the art), a yeast cell (e.g., any of the yeast cells described herein or known in the art), or a mammalian cell (e.g., any of the mammalian cells described herein or known in the art).

In some embodiments of these methods, the cell viability is determined by measuring a concentration of lactic acid dehydrogenase (LDH) in the test culture vessel.

EXAMPLES

The invention is further described in the following examples, which do not limit the scope of the invention described in the claims.

Example 1: Full Factorial Screening Combined with Inscribed Center Composite Design for Test Culture Vessels The rotary agitation ($RPM^3$), the concentration of the sensitizer, and the concentration of a protectant were selected as parameters. Full factorial design combined with inscribed center composite design were used to determine a set of test conditions (FIG. 7). The specific LDH production values were measured at each test condition. The results were used to provide an estimated contour of the selected parameters. Regions of poor performance and regions of operation failure were identified (FIG. 9).

Example 2: Predicting Specific LDH Production Values at Benchtop Scale

Proof-of-concept experiments were performed at the benchtop scale to determine the accuracy of the prediction methods as described herein.

The concentration of protectants in the benchtop scale were set to three different levels. For each level, two benchtop culturing bioreactors were tested. The peak specific LDH production values were measured due to perfusion process, and were compared against the predicted values.

Figure 13A:
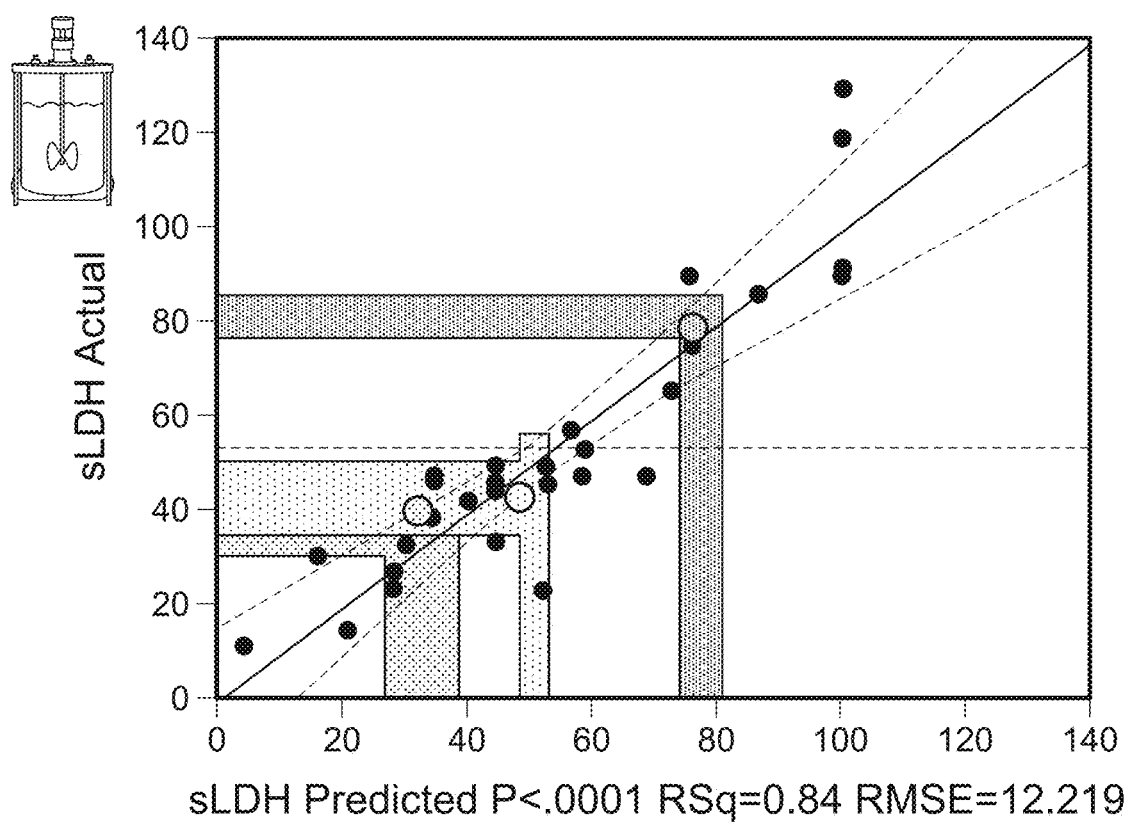
FIG. 13A is a graph that compares the observed specific LDH production values in the tested benchtop vessels against the predicted specific LDH production values.
Figures 13B, 13C:
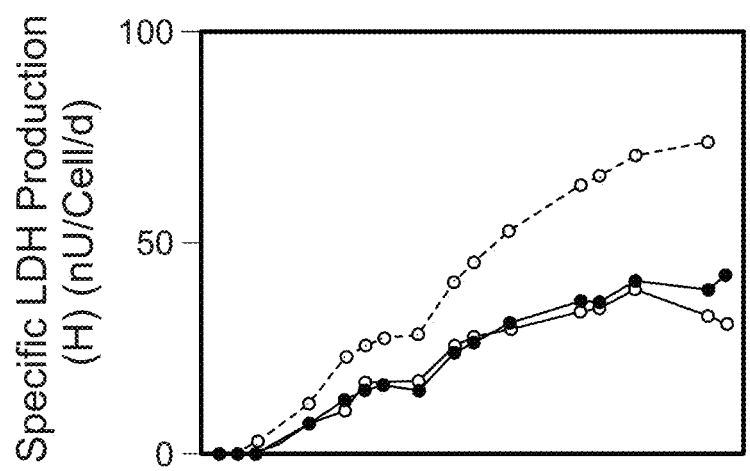
FIG. 13B depicts data from the experiment described in Example 2.
FIG. 13C lists the observed specific LDH production values with the predicted values.

The actual observed values from the benchtop scale experiments matched very well with those predicted values ($P<0.0001$, $R^2=0.84$) (FIG. 13A and FIG. 13C). The results demonstrated the methods as described herein can be successfully used to predict the effects of various parameter at a higher scale.

Experiments were performed maintaining an antifoam concentration range of 30-40 ppm antifoam addition per day. Pluronic® concentrations were adjusted from 1.8 g/L (dashed line), 2.8 g/L (solid line, closed circles), 3.8 g/L (solid line, open circles). Experiment was performed in replicate. This demonstrates the models capability of predicting specific LDH production when changing Pluronic® concentrations.

Figure 14:
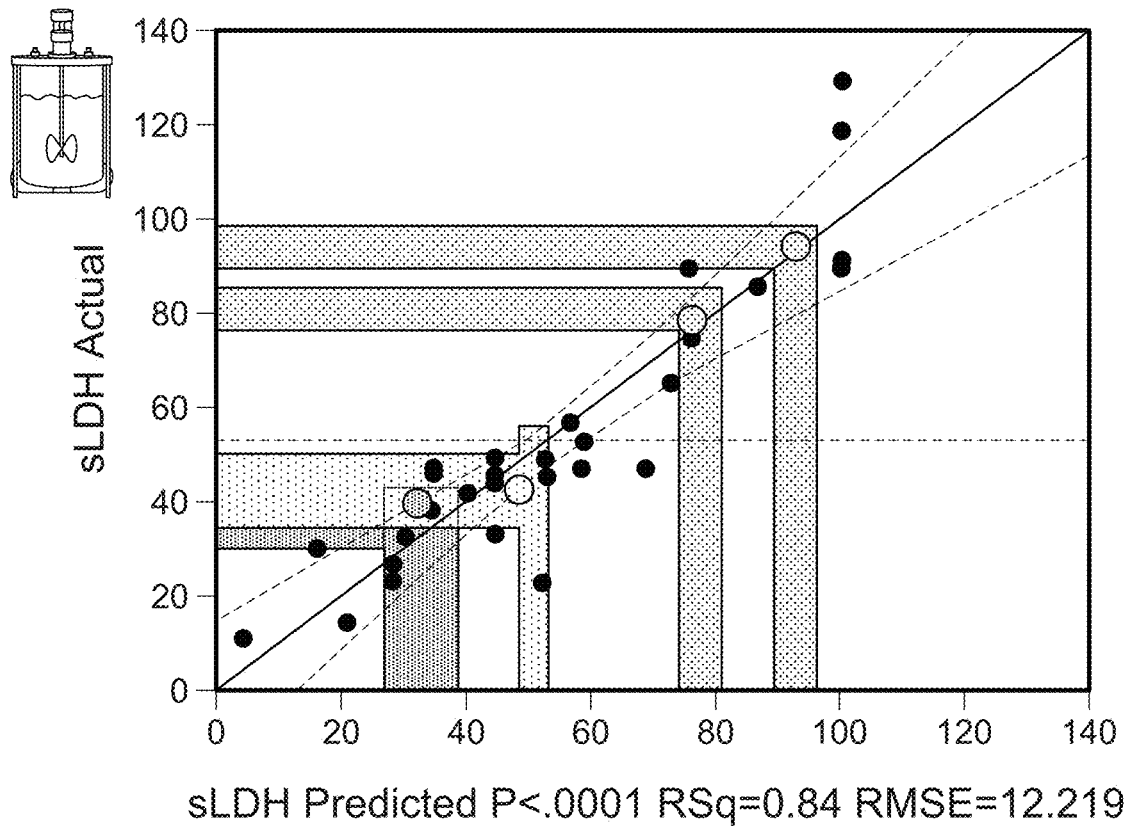
FIG. 14 compares the observed effects of antifoam agents on specific LDH production and the predicted effects of antifoam agents on specific LDH production.

Experiments were also performed to increase the concentration of the antifoam agent from 30 ppm to 80 ppm per day. The predicted LDH range was 90.19~96.38, which matched very well with the actual observed LDH range 94.74~99.36 (FIG. 14). The results showed the methods as described herein can be successfully used to predict the effects of antifoam agents.

Example 3: Predicting Specific LDH Production Values at Production Scale

Experiments were performed at the production scale to determine the accuracy of the model as described herein.

Three, 50-L production bioreactors and two 100-L production bioreactors were tested. The experiments tested poloxamer-188 (Pluronic® F68) concentrations that ranged from 1.8 g/L to 5.8 g/L.

Figures 15A, 15B:
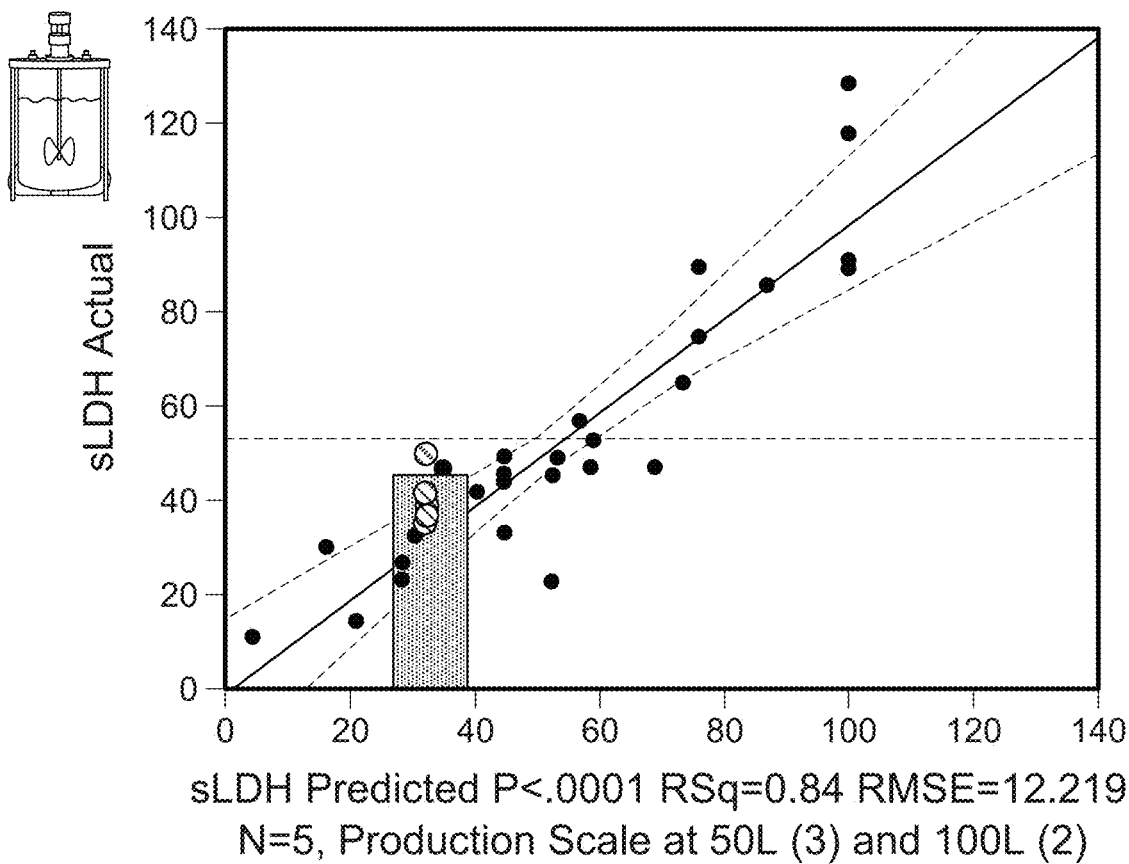
FIG. 15A is a graph that compares the observed specific LDH production values in the tested production bioreactors with the predicted values.
FIG. 15B lists the observed specific LDH production values in the tested production bioreactors with the predicted values.

The actual observed values for specific LDH production matched well with these predicted values ($P<0.0001$, $R^2=0.84$) (FIG. 15A and FIG. 15B). The results demonstrated that the methods as described herein can be successfully used to predict the effects of selected parameters at the production scale (production bioreactor scale).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of predicting the effect of a concentration of a sensitizer on cell viability in a production bioreactor, the method comprising:
 (a) determining cell viability under a plurality of test conditions in a test culture vessel, wherein the plurality of test conditions are defined by a set of parameters, wherein the plurality of testing conditions are selected based on full factorial screening and/or inscribed center composite design;
 (b) based on the cell viability in the test culture vessel under the plurality of conditions, predicting the effect of a concentration of a sensitizer on cell viability in a production bioreactor; and
 (c) culturing a cell in the production bioreactor using a concentration of the sensitizer predicted to result in:
 a specific cell death rate of less than 40% per day during the culturing of the cell in the production bioreactor;
 a cell specific LDH production of less than 150 nU/cell during the culturing of the cell in the production bioreactor; or an apparent growth rate of greater than 1% per day during the culturing of the cell in the production bioreactor.

2. The method of claim 1, wherein the set of parameters comprises shear stress, concentration of the sensitizer, and concentration of a protectant.

3. The method of claim 1, wherein the sensitizer is an antifoam agent.

4. The method of claim 1, wherein the test culture vessel is a baffled shake flask and the plurality of test conditions comprise one or more of:
   (a) a rotary agitation of about 125 RPM to about 400 RPM;
   (b) a concentration of the sensitizer of about 0 ppm to about 120 ppm; and
   (c) a concentration of a protectant that is about 1 g/L to about 10 g/L.

5. The method of claim 2, wherein the protectant is a poloxamer, a poloxamine, or a non-ionic surfactant.

6. A method for predicting cell viability in a production bioreactor, the method comprising:
   (a) selecting a set of parameters comprising at least two parameters;
   (b) determining cell viability under a plurality of test conditions as defined by the set of parameters in a test culture vessel, wherein the plurality of test conditions are selected based on full factorial screening and/or inscribed center composite design;
   (c) based on the cell viability in the test culture vessel under the plurality of conditions, predicting cell viability in the production bioreactor; and
   (d) culturing a cell in the production bioreactor using a condition predicted to result in:
   a specific cell death rate of less than 40% per day during the culturing of the cell in the production bioreactor;
   a cell specific LDH production of less than 150 nU/cell during the culturing of the cell in the production bioreactor; or
   an apparent growth rate of greater than 1% per day during the culturing of the cell in the production bioreactor.

7. The method of claim 6, wherein the set of parameters comprises shear stress, concentration of a sensitizer, and concentration of a protectant.

8. The method of claim 7, wherein the sensitizer is an antifoam agent.

9. The method of claim 6, wherein the test culture vessel is a baffled shake flask and the plurality of test conditions comprise one or more of:
   (a) a rotary agitation of about 125 RPM to about 400 RPM;
   (b) a concentration of the sensitizer of about 0 ppm to about 120 ppm; and
   (c) a concentration of a protectant that is about 1 g/L to about 10 g/L.

10. The method of claim 7, wherein the protectant is a poloxamer, a poloxamine, or a non-ionic surfactant.

\* \* \* \* \*